US007977474B2

(12) United States Patent
Love et al.

(10) Patent No.: US 7,977,474 B2
(45) Date of Patent: Jul. 12, 2011

(54) USES OF PORPHYRIN COMPOUNDS

(75) Inventors: William G. Love, Horsham (GB);
William Rhys-Williams, Burgess Hill
(GB); Derek Brundish, Horsham (GB)

(73) Assignee: Destiny Pharma Ltd., Falmer, Brighton
(GB)

( * ) Notice: Subject to any disclaimer, the term of this
patent is extended or adjusted under 35
U.S.C. 154(b) by 876 days.

(21) Appl. No.: 11/571,130

(22) PCT Filed: Jun. 22, 2005

(86) PCT No.: PCT/GB2005/002457
§ 371 (c)(1),
(2), (4) Date: Feb. 16, 2007

(87) PCT Pub. No.: WO2006/000765
PCT Pub. Date: Jan. 5, 2006

(65) Prior Publication Data
US 2007/0167619 A1    Jul. 19, 2007

(30) Foreign Application Priority Data

Jun. 23, 2004 (GB) .................................. 0414025.7

(51) Int. Cl.
C07D 487/22    (2006.01)
A61K 31/40     (2006.01)
A61K 31/44     (2006.01)
A61B 5/055     (2006.01)
(52) U.S. Cl. ........ 540/145; 514/183; 514/185; 514/410;
424/9.362; 424/9.61
(58) Field of Classification Search .................. 540/145;
514/183, 185, 410; 424/9–362
See application file for complete search history.

(56) References Cited

U.S. PATENT DOCUMENTS

| 4,318,883 A | 3/1982 | Polony et al. |
| 4,775,625 A | 10/1988 | Sieber |
| 4,851,403 A | 7/1989 | Picker |
| 4,878,891 A | 11/1989 | Judy et al. |
| 4,892,941 A | 1/1990 | Dolphin |
| 4,917,784 A | 4/1990 | Shelnutt |
| 4,962,197 A | 10/1990 | Foley et al. |

(Continued)

FOREIGN PATENT DOCUMENTS

EP    0 196 515    10/1986

(Continued)

OTHER PUBLICATIONS

Adler, et al., "On the preparation of Metahhoporphyrins" *J. Inorg. Nucl. Chem.* 32:2443-2445 (1970).

(Continued)

*Primary Examiner* — Ardin Marschel
*Assistant Examiner* — Savitha Rao
(74) *Attorney, Agent, or Firm* — Pabst Patent Group LLP

(57) ABSTRACT

The invention provides the use of a compound of Formula (I), or metallated derivative thereof, in the preparation of a medicament for killing or attenuating the growth of microorganisms by a method which does not comprise exposing the compound to a photodynamic therapy light source or a sonodynamic therapy ultrasound source Formula (I) wherein $X_1$, $X_2$, $X_3$, $X_4$, $Y_i$, $Y_2$, $Y_3$, $Y_4$ and Z have meanings given in the description. Preferably, the microorganisms are selected from the group consisting off bacteria, mycoplasmas, yeasts, fungi and viruses.

60 Claims, 13 Drawing Sheets

U.S. PATENT DOCUMENTS

| | | |
|---|---|---|
| 4,986,256 A | 1/1991 | Cohen |
| 4,987,226 A | 1/1991 | Buchler |
| 5,041,209 A | 8/1991 | Cha |
| 5,043,101 A | 8/1991 | Gordon |
| 5,077,394 A | 12/1991 | Dolphin |
| 5,109,016 A | 4/1992 | Dixon |
| 5,141,911 A | 8/1992 | Meunier |
| 5,149,697 A | 9/1992 | Johnson |
| 5,179,120 A | 1/1993 | Vogel et al. |
| 5,192,788 A | 3/1993 | Dixon |
| 5,192,797 A | 3/1993 | Raizon |
| 5,212,300 A | 5/1993 | Ellis, Jr. et al. |
| 5,223,494 A | 6/1993 | Kappas |
| 5,236,914 A | 8/1993 | Meunier |
| 5,262,532 A | 11/1993 | Tweedle |
| 5,268,371 A | 12/1993 | Mauclaire |
| 5,280,115 A | 1/1994 | Ellis, Jr. et al. |
| 5,281,616 A | 1/1994 | Dixon |
| 5,284,647 A | 2/1994 | Niedballa |
| 5,312,896 A | 5/1994 | Bhardwaj |
| 5,345,008 A | 9/1994 | Lyons et al. |
| 5,382,662 A | 1/1995 | Ellis |
| 5,397,777 A | 3/1995 | Fiel |
| 5,409,900 A | 4/1995 | Vogel et al. |
| 5,479,120 A | 12/1995 | McEwan |
| 5,489,716 A | 2/1996 | Ellis, Jr. et al. |
| 5,493,017 A | 2/1996 | Therien et al. |
| 5,545,516 A | 8/1996 | Wagner |
| 5,563,132 A | 10/1996 | Bodaness |
| 5,571,908 A | 11/1996 | Wijesekera |
| 5,599,924 A | 2/1997 | Therien et al. |
| 5,603,820 A | 2/1997 | Malinski |
| 5,629,198 A | 5/1997 | Mizumoto |
| 5,637,608 A | 6/1997 | Vogel et al. |
| 5,663,328 A | 9/1997 | Ellis, Jr. et al. |
| 5,674,467 A | 10/1997 | Maier |
| 5,703,230 A | 12/1997 | Boyle et al. |
| 5,756,723 A | 5/1998 | Therien et al. |
| 5,760,217 A | 6/1998 | Wijesekera |
| 5,767,272 A | 6/1998 | Wijesekera |
| 5,994,339 A | 11/1999 | Crapo |
| 5,998,128 A | 12/1999 | Roelant |
| 6,002,026 A | 12/1999 | Groves |
| 6,004,530 A | 12/1999 | Sagner |
| 6,013,241 A | 1/2000 | Marchal |
| 6,028,025 A | 2/2000 | Ying |
| 6,060,467 A | 5/2000 | Buelow |
| 6,066,628 A | 5/2000 | Stojiljkovic |
| 6,087,493 A | 7/2000 | Wheelhouse |
| 6,103,892 A | 8/2000 | Breslow |
| 6,104,714 A | 8/2000 | Baudelot |
| 6,107,326 A | 8/2000 | Jori |
| 6,107,480 A | 8/2000 | Funken |
| 6,124,452 A | 9/2000 | DiMagno |
| 6,127,356 A | 10/2000 | Crapo |
| 6,136,841 A | 10/2000 | Platzek |
| 6,147,070 A | 11/2000 | Facchini |
| 6,187,572 B1 | 2/2001 | Platz |
| 6,194,566 B1 | 2/2001 | Platzek |
| 6,208,553 B1 | 3/2001 | Gryko et al. |
| 6,245,707 B1 | 6/2001 | Chu |
| 6,251,367 B1 | 6/2001 | Platzek |
| 6,272,038 B1 | 8/2001 | Clausen et al. |
| 6,324,091 B1 | 11/2001 | Gryko et al. |
| 6,362,175 B1 | 3/2002 | Vinogradov |
| 6,368,396 B1 | 4/2002 | Nohr |
| 6,368,558 B1 | 4/2002 | Suslick |
| 6,372,727 B1 | 4/2002 | Crow |
| 6,399,769 B1 | 6/2002 | Nohr |
| 6,403,788 B1 | 6/2002 | Meunier |
| 6,407,330 B1 | 6/2002 | Lindsey et al. |
| 6,420,553 B1 | 7/2002 | Inoue |
| 6,420,648 B1 | 7/2002 | Lindsey |
| 6,433,162 B1 | 8/2002 | Nickel et al. |
| 6,436,171 B1 | 8/2002 | Wang |
| 6,444,194 B1 | 9/2002 | Robinson |
| 6,448,239 B1 | 9/2002 | Groves |
| 6,451,942 B1 | 9/2002 | Li |
| 6,479,477 B1 | 11/2002 | Crapo |
| 6,495,102 B1 | 12/2002 | Suslick |
| 6,524,379 B2 | 2/2003 | Nohr |
| 6,544,975 B1 | 4/2003 | Crapo |
| 6,566,517 B2 | 5/2003 | Miura |
| 6,573,258 B2 | 6/2003 | Bommer et al. |
| 6,582,930 B1 | 6/2003 | Ponomarev |
| 6,583,132 B1 | 6/2003 | Crapo |
| 6,596,935 B2 | 7/2003 | Lindsey et al. |
| 6,620,805 B1 | 9/2003 | Takle |
| 6,630,128 B1 | 10/2003 | Love et al. |
| 6,642,376 B2 | 11/2003 | Lindsey et al. |
| 6,727,240 B1 | 4/2004 | Neurath |
| 6,759,403 B2 | 7/2004 | Miura |
| 6,812,343 B2 | 11/2004 | Osuka |
| 6,818,763 B2 | 11/2004 | Vukovich |
| 6,827,926 B2 | 12/2004 | Robinson |
| 6,833,227 B2 | 12/2004 | Tanaka |
| 6,857,926 B1 | 2/2005 | Sulcs et al. |
| 6,900,197 B2 | 5/2005 | Szabo |
| 6,916,799 B2 | 7/2005 | Fridovich |
| 6,951,935 B2 | 10/2005 | Zhang et al. |
| 6,969,707 B2 | 11/2005 | Groves |
| 6,995,260 B2 | 2/2006 | Wu |
| 7,008,937 B2 | 3/2006 | Bommer |
| 7,025,734 B1 | 4/2006 | Ellis |
| 2002/0042407 A1 | 4/2002 | Fridovich et al. |
| 2002/0177704 A1 | 11/2002 | Sakata |
| 2002/0183245 A1 | 12/2002 | Hasan et al. |
| 2003/0032634 A1 | 2/2003 | Piganelli |
| 2003/0032799 A1 | 2/2003 | Miura |
| 2003/0050297 A1 | 3/2003 | Crapo |
| 2003/0055032 A1 | 3/2003 | Groves |
| 2003/0096721 A1 | 5/2003 | Hage |
| 2003/0100752 A1 | 5/2003 | Robinson |
| 2003/0105069 A1 | 6/2003 | Robinson |
| 2003/0166298 A1 | 9/2003 | Suslick |
| 2003/0176326 A1 | 9/2003 | Nifantiev |
| 2003/0225364 A1 | 12/2003 | Kraft |
| 2004/0014738 A1 | 1/2004 | Dubbelman et al. |
| 2004/0019031 A1 | 1/2004 | Crapo |
| 2004/0019204 A1 | 1/2004 | Che |
| 2004/0023941 A1 | 2/2004 | Crapo |
| 2004/0058902 A1 | 3/2004 | Batinic-Haberle |
| 2004/0063681 A1 | 4/2004 | Che |
| 2004/0116403 A1 | 6/2004 | Klimko |
| 2004/0127479 A1 | 7/2004 | Depke |
| 2004/0137281 A1 | 7/2004 | Ishikawa |
| 2004/0143001 A1* | 7/2004 | Love et al. .................. 514/410 |
| 2004/0169463 A1 | 9/2004 | Burn |
| 2004/0208855 A1 | 10/2004 | Allison |
| 2004/0210048 A1 | 10/2004 | Vukovich |
| 2004/0234495 A1 | 11/2004 | Maeda |
| 2004/0236157 A1 | 11/2004 | Heilgendorff |
| 2004/0254155 A1 | 12/2004 | Bommer |
| 2005/0008687 A1 | 1/2005 | Yuasa |
| 2005/0029470 A1 | 2/2005 | Muehlig |
| 2005/0090428 A1 | 4/2005 | Compans |
| 2005/0112058 A1 | 5/2005 | Laster |
| 2005/0124596 A1 | 6/2005 | Zhang |
| 2005/0137180 A1 | 6/2005 | Robinson |
| 2006/0003982 A1 | 1/2006 | Williams |
| 2006/0007889 A1 | 1/2006 | Khan |
| 2006/0013774 A1 | 1/2006 | Port |
| 2006/0030718 A1 | 2/2006 | Zhang |
| 2006/0041121 A1 | 2/2006 | Che |
| 2006/0074062 A1 | 4/2006 | Fridovich |
| 2006/0089344 A1 | 4/2006 | Abouabdellah |
| 2006/0129041 A1 | 6/2006 | Ellis |

FOREIGN PATENT DOCUMENTS

| | | |
|---|---|---|
| EP | 0350395 | 1/1990 |
| EP | 0350948 | 1/1990 |
| EP | 0 906 758 | 4/1999 |
| EP | 1 197 147 | 4/2002 |
| EP | 1 197 229 | 4/2002 |
| EP | 1 558 616 | 8/2005 |
| FI | 2002 A 000200 | 4/2004 |
| FR | 2 566 766 | 1/1986 |

| | | |
|---|---|---|
| GB | 2 397 067 | 7/2004 |
| JP | 5 800 0981 | 1/1983 |
| JP | 6 118 9284 | 8/1986 |
| PT | 102572 | 9/2002 |
| PT | 102581 | 12/2002 |
| RU | 2 238 950 | 10/2004 |
| SU | 721 442 | 3/1980 |
| WO | WO 91/16053 | 10/1991 |
| WO | WO 93/08455 | 4/1993 |
| WO | WO 95/33463 | 12/1995 |
| WO | WO 96/05862 | 2/1996 |
| WO | WO 96/31452 | 10/1996 |
| WO | WO 98/30102 | 7/1998 |
| WO | WO 98/31219 | 7/1998 |
| WO | WO 98/33503 | 8/1998 |
| WO | WO 98/39011 | 9/1998 |
| WO | WO 98/52610 | 11/1998 |
| WO | WO 99/66962 | 12/1999 |
| WO | WO 00/09111 | 2/2000 |
| WO | WO 00/12512 | 3/2000 |
| WO | WO 00/52012 | 9/2000 |
| WO | WO 00/74674 | 12/2000 |
| WO | WO 01/26655 | 4/2001 |
| WO | WO 01/96343 | 12/2001 |
| WO | WO 02/10173 | 2/2002 |
| WO | WO 02/13820 | 2/2002 |
| WO | WO 02/30190 | 4/2002 |
| WO | WO 02/30475 | 4/2002 |
| WO | WO 03/008430 | 1/2003 |
| WO | WO 03/057176 | 7/2003 |
| WO | WO 03/086389 | 10/2003 |
| WO | WO 2004/035590 | 4/2004 |
| WO | WO 2004/046151 | 6/2004 |
| WO | WO 2004/056828 | 7/2004 |
| WO | WO 2004/069273 | 8/2004 |
| WO | WO 2005/058909 | 6/2005 |
| WO | WO 2005/077269 | 8/2005 |
| WO | WO 2006/000765 | 1/2006 |

OTHER PUBLICATIONS

Ali and Van Lier, "Metal complexes as photo- and radiosensitizers", *Chem. Rev.*, 99(9):2379-450 (1999).

Baker and Cotten, "Delivery of bacterial artificial chromosomes into mammalian cells with psoralen-inactivated adenovirus carrier", *Nucleic Acids Res.*, 25(10):1950-6 (1997).

Bellin, et al., "Effects of photodynamic action on *E. coli*," *Arch. Biochem. Biophys.*, 132(1):157-64 (1969).

Berg, "Remote Guidance, Robotic Devices Stir Interest of Surgeons," *BBI Newsletter* (2000).

Bernadou, et al., "Potassium monopersulfate and a water-soluble manganese porphyrin complex, [Mn(TMPyP)](OAc)5, as an efficient reagent for the oxidative cleavage of DNA", *Biochemistry*, 28(18):7268-75 (1989).

Bertoloni, et al., "Photosensitizing activity of water- and lipid-soluble phthalocyanines on *Escherichia coli*", *FEMS Microbiol Lett.*, 59(1-2):149-55 (1990).

Bertoloni, et al., "Photosensitizing activity of water- and lipid-soluble phthalocyanines on prokaryotic and eukaryotic microbial cells", *Microbios.*, 71(286):33-46 (1992).

Bigey, et al.,"Preparation and Characterization by electrospray mass spectrometry of cationic metalloporphyrin DNA cleavers," *Bull. Soc. Chim. Fr.*, 133:679-689 (1996).

Borocci, et al.,"Characterization of mixed monolayers of phosphatidylcholine and a dicationic gemini surfactant SS-1 with a langmuir balance: effects of DNA," *Biophys J.* 81(4):2135-43 (2001).

Borocci, et al., *Chemical Abstracts* 136: 69974 (2001) (abstract only).

Branland, et al. "Nitroglycosylated meso-arylporphyrins as photoinhibitors of gram positive bacteria." *Bioorg Med Chem Lett.* 8(21):3007-10(1998).

Breuer, et al., "*Staphylococcus aureus*: colonizing features and influence of an antibacterial treatment in adults with atopic dermatitis", *Br. J. Dermatol.*, 147(1):55-61 (2002).

Brückner, et al., "Novel and improved syntheses of 5,15-diphenylporphyrin and its dipyrrolic precursors", *J. Porphyrins Phthalocyanines*, 2: 455-465 (1998).

Caminos, et al., "Photodynamic inactivation of *Escherichia coli* by novel meso-substituted porphyrins by 4-(3-N,N,N-trimethylammoniumpropoxy)phenyl and 4-(trifluoromethyl)phenyl groups", *Photochem. Photobiol. Sci.*, 5(1):56-65 (2006).

Casas, et al.,"Synthesis of Cationic Metalloporphyrin Precursors related to the Design of DNA Cleavers," *J. Org. Chem.* 58:2913-2917(1993).

Ceburkov and Gollnick, "Photodynamic therapy in dermatology", *Eur. J. Dermatol.*, 10(7):568-75 (2000).

Chan and Lau, "Syntheses of Acyl Rhodium Porphyrins by Aldehydic Carbon-Hydrogen Bond Activation with Rh(III) Porphyrin Chloride and Methyl," *organometallics* 25:260-265 (2006).

Chang, et al., "Fluoresecence Intensity Changes for Anthrylazacrown Ethers by Paramagnetic Metal Cations," *Bull. Korean Chem. Soc.* 20(7) 796-800 (1999).

Che, et al., "Gold(III) porphyrins as a new class of anticancer drugs: cytotoxicity, DNA binding and induction of apoptosis in human cervix epitheloid cancer cells", *Chem. Commun. (Camb)*, (14):1718-9 (2003).

Chen and Zhang, "Facile and efficient synthesis of meso-arylamino- and alkylamino-substituted porphyrins via palladium-catalyzed amination", *J. Org. Chem.*, 68(11):4432-8 (2003).

Chitta, et al., "Electrochemical, spectral, and computational studies of metalloporphyrin dimers formed by cation complexation of crown ether cavities", *Inorg. Chem.*, 43(22):6969-78 (2004).

Collman, et al., "Systematic variation of metal-metal bond order in metalloporphyrin dimmers", *Proc. Natl. Acad. Sci. U.S.A.*, 80(24):7684-7688 (1983).

Collman, et al., "Spectroscopic comparisons of MoW(porphyrin)$_2$ Heterodimers with Homologous Mo$_2$ and W$_2$ Quadruple Bonds: A dynamic NMR and Resonance Raman Study" *JACS* 120:1456-65 (1998).

Collman and Woo, "Rotational barrier of a molybdenum-molybdenum quadruple bond", *Proc. Natl. Acad. Sci. U.S.A.*, 81(8):2592-2596 (1984).

Cui and Wayland. "Activation of C—H / H—H bonds by rhodium(II) porphyrin bimetalloradicals", *J. Am. Chem. Soc.*, 126(26):8266-74 (2004).

Desandre, et al., "The effectiveness of oral tin mesoporphyrin prophylaxis in reducing bilirubin production after an oral heme load in a transgenic mouse model", *Biol. Neonate*, 89(3):139-46 (2006).

Dick, et al., "Molecular Encapsulation: Cyclodextrin-Based Analogues of Heme-Containing Proteins" *J. Am. Chem. Soc.* 114: 2664-2669 (1992).

Ding, et al., "Syntheses and in vitro evaluation of water-soluble "cationic metalloporphyrin-ellipticine" molecules having a high affinity for DNA", *J. Med. Chem.*, 34(3):900-6 (1991).

Diwu and Lown, "Phototherapeutic potential of alternative photosensitizers to porphyrins", *Pharmacol. Ther.*, 63(1):1-35 (1994).

Dougherty, "An update on photodynamic therapy applications", *J. Clin. Laser Med. Surg.*, 20(1):3-7 (2002).

Drexler, et al., *Chemical Abstracts*, Database Accession No. 1998:433421.

Drexler, et al., "Design, synthesis and cleaving activity of an abiotic nuclease based on a Mn(III) porphyrin complex bearing two acridine moieties" *Chem. Comm.*, 1343-1344 (1998).

Ehrenberg, et al., "Fluorescence spectral changes of hematoporphyrin derivative upon binding to lipid vesicles, *Staphylococcus aureus* and *Escherichia coli* cells", *Photochem. Photobiol.*, 41(4):429-35 (1985).

Feng and Senge, "An efficient synthesis of highly functionalized asymmetric porphyrins with organolithium reagents" *Journal of the Chemical Society, Perkin Transactions* 1:1030-1038 (2001).

Fu and Wayland, "Equilibrium thermodynamic studies in water: reactions of dihydrogen with rhodium(III) porphyrins relevant to Rh—Rh, Rh—H, and Rh—Oh bond energetics", *J. Am. Chem. Soc.*, 126(8):2623-31 (2004).

Fukushima, et al., "Synthesis and properties of rhodium(III) porphyrin cyclic tetramer and cofacial dimmer", *Inorg. Chem.*, 42(10):3187-93 (2003).

Gao, et al., "Versatile synthesis of meso-aryloxy- and alkoxy-substituted porphyrins via palladium-catalyzed C—O cross-coupling reactions", *Org. Lett.*, 5(18):3261-4 (2003).

Gebauer, et al., "Nuetral π-Radicals of lithium porphyrins: synthesis and characterization," *J. Chem. Soc.Dalton Trans.* 111-112 (2000).

Geyer, et al., "Subophthalocyanines: Preparation, reactivity and physical properties", *Synthesis* 1139-1151 (1996).

Godbey, et al., "Size matters: molecular weight affects the efficiency of poly(ethylenimine) as a gene delivery vehicle", *J. Biomed. Mater. Res.*, 45(3):268-75 (1999).

Hamblin, et al., "Rapid control of wound infections by targeted photodynamic therapy monitored by in vivo bioluminescence imaging", *Photochem. Photobiol.*, 75(1):51-7 (2002).

Hamblin and Hassan, "Photodynamic therapy: a new antimicrobial approach to infectious disease?", *Photochem. Photobiol. Sci.*, 3(5):436-50 (2004).

Hamstra, et al., "Molybdenum(V) on an Oxide String. Synthesis and Structure of the Novel Linear Trinuclear Complex {[MoO(TPP)][O-Mo(TPP)-O][MoO(TPP)]}ClO(4)", *Inorg. Chem.*, 38(15):3554-3561 (1999).

Harroti, et al.,"Anion-Selective Electrods Based on Porphrin Complexes of Tetravalent Metal Ions," *Anal Sci.* 17:1353-1356 (2001).

Helander, et al., "Polyethyleneimine is an effective permeabilizer of gram-negative bacteria", *Microbiology*, 143 (Pt 10):3193-9 (1997).

Hermann, et al, "Heterogeneous metal-insertion: a novel reaction with porphyrins," *Can. J. Chem.* 56:184-1087 (1978).

Hopper, "Photodynamic therapy: a clinical reality in the treatment of cancer", *Lancet Oncol.*, 1:212-9 (2000).

Ito, "Cellular and subcellular mechanisms of photodynamic action: the 1O2 hypothesis as a driving force in recent research", *Photochem. Photobiol.*, 28(4-5):493-508 (1978).

Jin, et al., "Combined effects of photodynamic and sonodynamic treatment on experimental skin cancer on C3H mice" *Photomedicine and Photobiology* 19:65-68 (1997).

Jorgensen and Ferraro, "Antimicrobial susceptibility testing: special needs for fastidious organisms and difficult-to-detect resistance mechanisms", *Clin. Infect. Dis.*, 30(5):799-808 (2000).

Jori and Brown, "Photosensitized inactivation of microorganisms" *Photochem. Photobiol. Sci.*, 3(5):403-5 (2004).

Kassab, et al., "Phthalocyanine-photosensitized inactivation of a pathogenic protozoan, *Acanthamoeba palestinensis*", *Photochem. Photobiol. Sci.*, 2(6):668-72 (2003).

Kim, et al., Synthesis and Crystal Structure of an Organoimido Molybdenum (V) Porphyrin Salt, [Mo(Nme)(TPP)(H₂O)][(I₃](TPP=Tetraphenylporphyrin) *Inorg. Chem.* 34:2483-2486 (1995).

Kim, et al.,"Synthesis and Rotational Barrier of Tungsten(II)Porphyrin Dimer" *Polyherdron* 15(1)57-62 (1996).

Kubát, et al., Interaction of novel cationic meso-tetraphenylporphyrins in the ground and excited states with DNA and nucleotides, *J. Chem. Soc. Perkin Trans.* 1:933-941 (2000).

Kudrevich, et al., "Syntheses of trisulfonated phthalocyanines and their derivatives using boron(III) subphthalocyanines as intermediates", *J. Org. Chem.* 61: 5706-5707 (1996).

Kuroyanagi, et al., "Extremely sensitive detection of photoresponses in ultrathin films containing porphyrins by the optical waveguide", *Chemical Abstracts* 124: 131104 (1995) (abstract only).

Ladan, et al., "The antibacterial activity of haemin compared with cobalt, zinc and magnesium protoporphyrin and its effect on potassium loss and ultrastructure of *Staphylococcus aureus*", *FEMS Microbiol. Lett.*, 112(2):173-7 (1993).

Lambrechts, et al., "Effect of monovalent and divalent cations on the photoinactivation of bacteria with meso-substituted cationic porphyrins", *Photochem. Photobiol.*, 79(3):297-302 (2004).

Leanord and Smith,"Model Systems for cytochrome P450 Dependent Mono-oxygenases. Part 7. Alkene Epoxidation by Iodosylbensene Cataysed by Ionic Iron(III) Tetraarylporphyrins Supported on Ion-exchnage Resins," *J. Chem. Soc. Perkin Trans.* 2 2::1917-1923 (1990).

Lewis, Hawley's Condensed Chemical Dictionary, pp. 718, 803, and 990.

Li, et al., "A series of meso-tris (N-methyl-pyridiniumyl)-(4-alkylamidophenyl) porphyrins: synthesis, interaction with DNA and antibacterial activity", *Biochim. Biophys. Acta.*, 1354(3):252-60 (1997).

Lin, et al., "Photosensitization, uptake, and retention of phenoxazine Nile blue derivatives in human bladder carcinoma cells", *Cancer Res.*, 51(4):1109-16 (1991).

Liu, et al., "Synthesis of tail-type pyridinium(triethylammonium)-porphyrin quaternary ammonium salt", *Chemical Abstracts* 133: 104912 (2000) (abstract only).

Lou, et al., "Modulation of PDT-induced apoptosis by protein kinases and phosphatases" *Proc. SPIE* 2675:132-137 (1996).

Maisch, et al., "Antibacterial photodynamic therapy in dermatology", *Photochem. Photobiol. Sci.*, 3(10):907-17 (2004).

Malik, et al., "Effects of photoactivtaed haematoporphyrin derivative on bacteria and antibiotic resistance," *Microbios. Lett.*, 21(83-84):103-112 (1982).

Malik, et al., "Bactericidal effects of photoactivated porphyrins—an alternative approach to antimicrobial drugs", *J. Photochem. Photobiol. B.*, 5(3-4):281-93 (1990).

Malik, et al., "Photodynamic inactivation of Gram-negative bacteria: problems and possible solutions", *J. Photochem. Photobiol. B.*, 14(3):262-6 (1992).

Maliyackel, et al., "Photoinduced oxidation of a water-soluble manganese(III) porphyrin", *Proc. Natl. Acad. Sci. U.S.A.*, 83(11):3572-3574 (1986).

Manka and Lawrence,"High Yeild Synthesis of 5,15-Diarylporphyrins," *Tet. Lett.* 30(50):6989-6992 (1989).

Mehta, et al., "Cholate-interspersed porphyrin-anthraquinone conjugates: Photonuclease activity of large sized, 'tweezer-like' molecules", *J. Chem. Soc. Perkin. Trans* 1, 2177-2181 (1999).

Merchat, et al., "Meso-substituted cationic porphyrins as efficient photosensitizers of gram-positive and gram-negative bacteria", *J. Photochem. Photobiol. B.*, 32(3):153-7 (1996).

Merchat, et al., "Studies on the mechanism of bacteria photosensitization by meso-substituted cationic porphyrins", *J. Photochem. Photobiol. B.*, 35(3):149-57 (1996).

Mestre, et al., "Influence of the nature of the porphyrin ligand on the nuclease activity of metalloporphyrin-oligonucleotide conjugates designed with cationic, hydrophobic or anionic metalloporphyrins", *Nucleic Acids Res.*, 25(5):1022-7 (1997).

Milanesio, et al., "Photodynamic studies of metallo 5,10,15,20-tetrakis(4-methoxyphenyl) porphyrin: photochemical characterization and biological consequences in a human carcinoma cell line", *Photochem. Photobiol.*, 74(1):14-21 (2001).

Minnock, et al., "Photoinactivation of bacteria. Use of a cationic water-soluble zinc phthalocyanine to photoinactivate both gram-negative and gram-positive bacteria", *J. Photochem. Photobiol. B.*, 32(3):159-64 (1996).

Moan, et al., "The mechanism of photodynamic inactivation of human cells in vitro in the presence of haematoporphyrin", *Br. J. Cancer*, 39(4):398-407 (1979).

Monti, et al., "Micelle-bound metalloporphyrins as highly selective catalysts for the epoxidation of alkenes", *Chemical Abstracts* 129: 81626 (1998) (abstract only).

Mosman, et al., "Rapid colorimetric assay for cellular growth and survival: application to proliferation and cytotoxicity assays", *J. Immunol. Methods*, 65(1-2):55-63 (1983).

Munakata, et al., "Synthesis and nucleic acid-binding properties of water-soluble porphyrins appending platinum(II) complexes", *Chem. Pharm. Bull.* (Tokyo), 49(12):1573-80 (2001).

Nasim and Brychy, "Genetic effects of acridine compounds", *Mutat. Res.*, 65(4):261-88 (1979).

Neely and Bottomley, "Inter-Metal Nitrogen Atom Transfer Reactions between Nitridochromium(V) and Chromium(III) Porphyrins," *Inorg. Chem.* 36:5432-5434 (1997).

Nistri, et al., "A novel synthesis of 5,15-trimethylammonium substituted porphyrins and their evaluation as potential antimicrobial photosensitizers," *J. Porphyrins and Phthalocyaninies* 9:290-7 (2005).

Nitzan, et al. "Characterization of hemin antibacterial action on *Staphylococcus aureus*," *FEMS Micorbiol. Lett.* 48:401-406 (1987).

Nitzan, et al., "Inactivation of gram-negative bacteria by photosensitized porphyrins", *Photochem. Photobiol.*, 55(1):89-96 (1992).

Nitzan, et al., "Eradication of *Acinetobacter baumannii* by photosensitized agents in vitro", *J. Photochem. Photobiol. B.*, 42(3):211-8 (1998).

Nitzan & Ashkenazi, "Photoinactivation of *Acinetobacter baumannii* and *Echerichia coli* B by a cationic hydrophilic porphyrin at various light wavelengths", *Curr. Microbiol.* 42: 408-414 (2001).

Okuno, et al., "An improved synthesis of surfactant porphyrins", *Synthesis* 537-539 (1980).

Orenstein, et al. "The use of porphyrins fo reradication of *Staphylococcus aureus* in burn wound victims" *FEMS Immunol. Med. Microbiol.* 19:307-14 (1998).

Parker; McGraw-Hill Encyclopeddia of Chemistry (2nd Edition) pp. 637.

Pitie, et al. "Preferential hydroxylation by the chemical nuclease meso-tetrakis-(4-N-methylpyridiniumyl)porphyrinatioangaaneseIII pentaacetate/KHSO5 at the 5' carbon of deoxyriboses on both 3' sides of three contiguous A. T base pairs in short double-stranded oligonucleotides," *PNAS* 89:3967-3971 (1992).

Petho, "The porphyrins in cancer and virus research" *Acta Physiol. Hungarica* 83(2) 113-119 (1995).

Pratviel, et al. "Mechanism of DNA cleavage by cationic manganese porphyrins: hydroxylations at the 1'-carbon and 5'-carbon atoms of deoxyriboses as initial damages," *Nucleic Acids Res.* 25;19(22):6283-8(1991).

Reddi, et al., "Photophysical properties and antibacterial activity of meso-substitiuted cationic porphyrins," *Photochem. Photobiol.* 75:(5) 462-470 (2002).

*Remington: The Science and Practice of Pharmacy,* 19th edition (Gennaro, ed.) Mack Publishing Company: Pennsylvania, pp. 1585-1597 (1995).

Renner and Fadjer "Oxidative chemistry of Nickel Porphyrins" *J. Biol. Inorg. Chem.* 6:823-830 (2001).

Ribeiro "Synthesis of New Cationic Metalloporphyrins and Heterodimer formation with anionic metallophthalocyanines," *J. Barz. Chem. Soc.* 14(6):914-21 (2003).

Sadick, "Current aspects of bacterial infections of the skin," *Dermatol. Clin* 15(2): 341-349 (1997).

Sakurai, et al. "A new candidate for insulinomimetic vanadium complex: synergism of oxovanadium(IV)porphyrin and sodium ascorbate," *Bioorg Med Chem Lett.* 14(5):1093-6(2004).

Salmon-Divon, et al. "Mechanistic aspects of *Escherichia coli* photodynamic inactivation by cationic tetra-meso(N-methylpyridyl)porphine," *Photochem Photobiol Sci.* 3(5):423-9(2004).

Schneider & Wang, "DNA interactions with porphyrins bearing ammonium side chains", *J. Org. Chem.* 59: 7473-7478 (1994).

Segalla, et al., "Photophysical, photochemical and antibacterial photosensitizing properties of a novel octactaionic Zn(II)-phthalocyanine", *Photochem. Photobiol. Sci.* 1: 641-648 (2002).

Sisemore, et al "Metalloporphyrin Peroxo Complexes of Iron(III), Manganese(III), and Titanium(IV). Comparative Studies Demonstrating That the Iron(III) Complex Is Extremely Nucleophilic," *Inorg. Chem.* 36:979-984 (1997).

Smith, "Photodynamic therapy," *Curr. Probl. Cancer* 26(2): 67-108 (2002).

Smith and Lower "The mechanism of the reaction between t-butyl hydroperoxide and 5,10,15,20-Tetra(N-methyl-4-pyridyl) porphyrinatoiron (III) pentachloride in aqueous solution," *J. Chem. Soc. Perkin. Trans.* 2:31-39 (1991).

Sol, et al., "Nitroglycosylated meso-arylporphyrins as photoinhibitors of gram positive bacteria", *Bioorg. Med. Chem. Lett.*, 8(21):3007-10 (1998).

Soncin, et al., "Approaches to selectivity in the Zn(II)-phthalocyanine-photosensitized inactivation of wild-type and antibiotic-resistant *Staphylococcus aureus*", Photochem Photobiol Sci 1, 815-819 (2002).

Soukos, et al., "Targeted antimicrobial photochemotherapy", *Antimicrob. Agents Chemother.* 42: 2595-2601 (1998).

Stojilijkovic, "Antimicrobial properties of porphyrins", *Exp. Opin. Invest. Drugs* 10(2): 309-320 (2001).

Stojilijkovic,et al. "Non-iron metalloporphyrins: potent antibacterial compounds that exploit haem/Hb uptake systems of pathogenic bacteria," *Mol Microbiol.* 31(2):429-42(1999).

Sun,et al. "Reversible Electrochemical generation of a rhodium(II) porphyrin: Thwarting disproportionation with weakly coordinating anions," *Inorg. Chem.* 42:4507-4509 (2003).

Takehara,et al. "Tumour enhancement with newly developed Mn-metalloporphyrin (HOP-9P) in magnetic resonance imaging of mice," *Br J Cancer* 84(12):1681-5(2001).

Szpakowska, et al., "Susceptibility of *Pseudomonas aeruginosa* to a photodynamic effect of the arginine hematoporphyrin derivative", *Internet J Antimicrob Agents* 8, 23-27 (1997).

Toffoli,et al., "In K562 leukemia cells treated with doxorubicin and hemin, a decrease in c-myc mRNA expression correlates with loss of self-renewal capability but not with erythroid differentiation," *Leuk Res.* 13(4):279-87 (1989).

Tsutsui, "The usefulness of the porphyrin-viologen linked compounds as a photosensitizer for the photodynamic therapy (PDT)", *Chemical Abstracts* 119: 66705 (1992) (abstract only).

Tunger, et al., "Evaluation of rational antibiotic use," *Int. J. Microb. Agents* 15(2): 131-135 (2000).

Uehata, et al., "Magnetic field effects on the decay rates of photogenerated geminate racidal pairs in reversed micelles", *Chemical Abstracts* 111: 243931 (1989) (abstract only).

Usui, et al., "Effects of external magnetic fields on laser-induced electron-transfer reactions in porphyrin-viologen pairs at the surface of molecular bilayers", *Chemical Abstracts* 108: 204085 (abstract only).

Valduga, et al., "Effect of extracellularly generated singlet oxygen on gram-positive and gram-negative bacteria," *J. Photochem. Photobiol. B.* 21: 81-86 (1993).

Valduga, et al., "Photosensitization of wild and mutant strains of *Escherichia coli* by meso-tetra (N-methy1-4-pyridyl)porphine," *Biochem. Biophys. Res. Commun.* 256: 84-88 (1999).

Venezio,et al. "Bactericidal effects of photoradiation therapy with hematoporphyrin derivative," *J. Infect. Dis.* 151(1):166-9(1985).

Vzorov,et al. "Inactivation of human immunodeficiency virus type 1 by Porphyrins," *Antimicrob Agents Chemother.* 46(12):3917-25(2002).

Wainwright, "Non-porphyrin photosensitizers in biomedicine", *Chemical Society Reviews* 351-359 (1996).

Wainwright, "Photodynamic antimicrobial chemotherapy (PACT)", *J. Antimicrob. Chemother.* 42: 13-28 (1998).

Walshe, "Management of penicillamine nephropathy in Wilson's disease: a new chelating agent," *Lancet* 2(7635):1401-2(1969).

Wang, et al."Facile Syntheses of Titanium(II), Tin(II), and Vanadium(II) Porphyrin Complexes through Homogeneous Reduction. Reactivity of trans-(TTP)TiL(2) (L=THF, t-BuNC)," *Inorg Chem.* 37(1):5-9(1998).

Wang and Woo, "Facile Syntheses of Titanium(II), Tin(II), and Vanadium(II) Porphyrin Complexes through Homogeneous Reduction. Reactivity of trans-(TTP)TiL(2) (L=THF, t-BuNC)," *Inorg. Chem.* 37(1):5-9(1998).

Wiehe, et al., "Hydrophilicity vs. hydrophobicity—varying the amphiphilic structure of porphyrins related to the photosensitizer m-THPC", *J. Porphyrins Phthalocyanines* 5: 758-761 (2001).

Wilson, "Lethal photosensitisation of oral bacteria and its potential application in the photodynamic therapy of oral infections," *Photochem Photobiol Sci.* 3(5):412-8(2004).

Wong, et al. "Physiologically stable vanadium(IV) porphyrins as a new class of anti-HIV agents,"*Chem Commun (Camb)*.(28):3544-6(2005).

Iritani, "The combinatorial enumeration of structural isomers of alkanes", *J. Chem. Software,* 5(2):65-80 (1999) (with English Abstract).

Maisch, et al., "Photodynamic effects of novel XF porphyrin derivatives on prokaryotic and eukaryotic cell", *Antimicrobial Agents and Chemotherapy,* 49(4):1542-1562 (2005).

Treibs & Haberle, "Concerning the synthesis and the electron spectrum of ms-substituted porphine", *Justus Liebigs Ann Chem,* 178:183-207 (1968) (with English Abstract).

Declaration of Professor David Dolphin, submitted in prosecution of European Patent No. 1 578 750, submitted Jun. 6, 2009.

Wu, et al, "Iron porphyrin treatment extends survival in a transgenic animal model of amyotrophic lateral sclerosis," *J. Neurochem.* 85(1):142-50(2003).

Yashunsky, et al., "Chemisthry of dimeththylaminoporphyrins. 2. Porphyrin dimers linked by pyrrolylinethylene units" *Tetrahedron Lett.*, 380)105-108 (1997).

Yashunsky, et al., "Chemistry of *meso*-dimethytaminopropenyl-porphyrins and -bisporphyrins: the synthesis of australochlorin, a benzothlorin isomer", *Aust. J. Chem.*, 50:487-93 (1997).

Yeung, et al., "Facile synthesis and nonlinear optical properties of push-pull 5,15-diphenylporphyrine", *J. Org. Chem.*, 63:7143-50 (1998).

Zhang, et al. "Synthesis and antibacterial study of 10, 15, 20-triphenyl-5-(4-hydroxy-3-(trimethylammonium) methyl)phenylporphyrin as models for combination of porphyrin and alkylating agent," *Bioorg Med. Chem. Lett*, 13(6):1097-100(2003).

Zhou, et al. "Synthesis of rhodium porphyrin aryls via intermolecular arene carbon-hydrogen bond activation," *Inorg. Chim. Acta* 270:551-554 (1998).

* cited by examiner

USES OF PORPHYRIN COMPOUNDS

CROSS-REFERENCE TO RELATED APPLICATIONS

This application is a filing under 35 U.S.C. §371 of PCT/GB2005/002457 filed with the Great Britain Receiving Office of the Patent Cooperation Treaty on Jun. 22, 2005, which claims the benefit of British Patent Application No. GB 0414025.7, which was filed with the British Patent Office on Jun. 23, 2004.

FIELD

The present invention relates to new uses of porphyrin compounds and, in particular, the use of such compounds in the curative or prophylactic treatment of microbial colonisation and infection.

BACKGROUND

The resistance to antibiotics developed by an increasing number of microorganisms is recognised to be a worldwide health problem (Tunger et al., 2000, *Int. J. Microb. Agents* 15: 131-135; Jorgensen et al., 2000, *Clin. Infect. Dis.* 30: 799-808). As a consequence, the development of new approaches for killing microorganisms is urgently required.

The treatment of microbial infections by photodynamic therapy (PDT) represents a valuable recent method for eradicating bacteria since it involves a mechanism which is markedly different from that typical of most antibiotics. Thus, PDT is based on the use of a photosensitising molecule that, once activated by light, generates oxygen reactive species that are toxic for a large variety of prokaryotic and eukaryotic cells including bacteria, mycoplasmas and yeasts (Malik et al., 1990, *J. Photochem. Photobiol. B Biol.* 5: 281-293; Bertoloni et al., 1992, *Microbios* 71: 33-46). Importantly, the photosensitising activity of many photodynamic agents against bacteria is not impaired by the resistance to antibiotics but, instead, depends mainly on their chemical structure (Malik et al., 1992, *J. Photochem. Photobiol. B Biol.* 14: 262-266).

Various types of neutral and anionic photosensitising agents exhibit a pronounced phototoxic activity against Gram positive bacteria. However, such photosensitising agents exert no appreciable cytotoxic activity against Gram negative bacteria unless the permeability of the outer membrane is altered by treatment with ethylene diamine tetra-acetic acid (EDTA) or polycations (Bertoloni et al., 1990, *FEMS Microbiol. Lett.* 71: 149-156; Nitzan et al., 1992, *Photochem. Photobiol.* 55: 89-97). It is believed that the cellular envelope of Gram negative bacteria, which is more complex and thicker than that of Gram positive bacteria, prevents an efficient binding of the photosensitising agent or intercepts and deactivates the cytotoxic reactive species photogenerated by the photosensitising agent (Ehrenberg et al., 1985, *Photochem. Photobiol.* 41: 429-435; Valduga et al., 1993, *J. Photochem. Photobiol. B. Biol.* 21: 81-86).

In contrast, positively charged (cationic) photosensitising agents, including porphyrins and phthalocyanines, promote efficient inactivation of Gram negative bacteria without the need for modifying the natural structure of the cellular envelope (Merchat et al., 1996, *J. Photochem. Photobiol. B. Biol.* 32: 153-157; Minnock et al., 1996, *J. Photochem. Photobiol. B. Biol.* 32: 159-164). It appears that the positive charge favours the binding of the photosensitising agent at critical cellular sites that, once damaged by exposure to light, cause the loss of cell viability (Merchat et al., 1996, *J. Photochem. Photobiol. B. Biol.* 35: 149-157). Thus, it has been reported that *Escherichia coli* is efficiently inactivated by visible light after incubation with the cationic 5,10,15,20-tetrakis-(4-N-methylpyridyl)-porphine ($T_4MPyP$) (Valduga et al., 1999, *Biochem. Biophys. Res. Commun.* 256: 84-88). The phototoxic activity of this porphyrin is mainly mediated by the impairment of the enzymic and transport functions of both the outer and cytoplasmic membranes, rather than by binding to DNA.

However, the utility of known porphyrin-based antimicrobial agents is limited due to their toxicity against mammalian host tissue cells, i.e. the compounds are unable to differentiate between target microbial cells and host cells. In addition, the utility of known porphyrin-based antimicrobial agents is further limited by their relatively low potency for target microbial cells.

Furthermore, not all microbial infections are suitable for treatment using photodynamic therapy, e.g. the site of infection may not be accessible to light.

Hence, there is a need for new methods of killing and attenuating the growth of microbial agents.

SUMMARY

According to a first aspect of the invention, there is provided use of a compound of fonnula I in the preparation of a medicament for killing or attenuating the growth of microorganisms by a method which does not comprise exposing the compound to a photodynamic therapy light source or a sonodynamic therapy ultrasound source

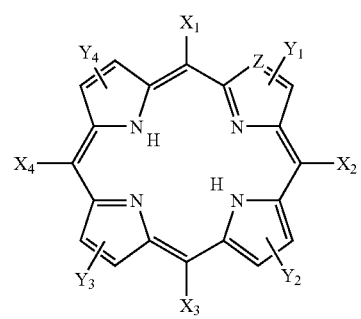

I wherein:

$X_1$, $X_2$, $X_3$, and $X_4$ independently represent (i.e. are the same or different) a hydrogen atom, a lipophilic moiety, a phenyl group, a lower alkyl, alkaryl or aralkyl group, or a cationic group of the following formula;

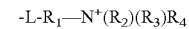

wherein:

L is a linking moiety or is absent;

$R_1$ represents lower alkylene, lower alkenylene or lower alkynylene, which is optionally substituted by one or more substituents selected from lower alkyl, lower alkylene (optionally interrupted with oxygen), fluoro, $OR_5$, $C(O)R_6$, $C(O)OR_7$, $C(O)NR_8R_9$, $NR_{10}R_{11}$ and $N^+R_{12}R_{13}R_{14}$; and $R_2$, $R_3$ and $R_4$ independently represent (i.e. are the same or different) H, aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)NR_8R_9$, $NR_{10}R_{11}$ and $N^+R_{12}R_{13}R_{14}$ Z is —CH or N;

$Y_1$, $Y_2$, $Y_3$ and $Y_4$ are absent or independently represent aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)NR_8R_9$, $NR_{10}R_{11}$, $N^+R_{12}R_{13}R_{14}$, or, taken in conjunction with the pyrrole ring to which they attach, may form a cyclic group; and $R_5$, $R_6$, $R_7$, $R_8$, $R_9$, $R_{10}$, $R_{11}$, $R_{12}$, $R_{13}$ and $R_{14}$ independently represent H or lower alkyl provided that at least one of $X_1$, $X_2$, $X_3$ and $X_4$ is a cationic group as defined above and at least one of $X_1$, $X_2$, $X_3$ and $X_4$ is a hydrogen atom, a phenyl group, a lipophilic moiety, or a lower alkyl, alkaryl or aralkyl group.

The term "lower alkyl" is intended to include linear or branched, cyclic or acyclic, $C_1$-$C_{20}$ alkal which may be interrupted by oxygen (preferably no more than five oxygen atoms are present in each alkyl chain). Lower alkyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_1$-$C_{18}$ alkyl, $C_1$-$C_{16}$ alkyl, $C_1$-$C_{14}$ alkyl, $C_1$-$C_{12}$ allyl, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkgl, $C_1$-$C_3$ alkyl and $C_1$-$C_2$ alkyl. Preferred lower alkyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$ and $C_{16}$ alkyl.

Thus, any one or more of $N^+R_2R_3R_4$ and/or $N^+R_{12}R_{13}R_{14}$ may represent cyclic amine/ammonium groups, for example:

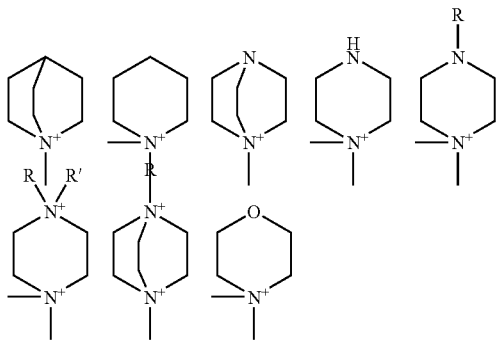

It will be appreciated that the cyclic amine/ammonium groups may also comprise fewer or greater than six members, for example such groups may comprise 4-, 5-, 7-, 8-, 9- or 10-membered rings.

The term "lower alkylene" is to be construed accordingly.

The terms "lower alkenyl" and "lower alkynyl" are intended to include linear or branched, cyclic or acyclic, $C_2$-$C_{20}$ alkenyl and alkynyl, respectively, each of which may be interrupted by oxygen (preferably no more than five oxygen atoms are present in each alkenyl or alkynyl chain).

The term "lower alkenyl" also includes both the cis and trans geometric isomers. Lower alkenyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_2$-$C_{18}$ alkenyl, $C_2$-$C_{17}$ alkenyl, $C_2$-$C_{16}$ alkenyl, $C_2$-$C_{14}$ alkenyl, $C_2$-$C_{12}$ alkenyl, $C_2$-$C_{10}$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl and $C_3$-$C_4$ alkenyl. Preferred lower alkenyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_2$, $C_3$, $C_4$, $C_5$, $C_6$, $C_7$, $C_8$, $C_9$, $C_{10}$, $C_{11}$, $C_{12}$, $C_{13}$ and $C_{14}$ alkenyl.

The term "lower alkenylene" is to be construed accordingly.

"Lower alkynyl" groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_2$-$C_{18}$ alkynyl, $C_2$-$C_{16}$ alkynyl, $C_2$-$C_{14}$ alkynyl, $C_2$-$C_{12}$ alkynyl, $C_2$-$C_{10}$ alkynyl, $C_2$-$C_9$ alkynyl, $C_2$-$C_8$ alkynyl, $C_2$-$C_7$ alkynyl, $C_2$-$C_6$ alknyl, $C_2$-$C_5$ alkynyl, $C_2$-$C_4$ alkynyl, $C_2$-$C_3$ alkynyl and $C_3$-$C_4$ alkynyl. Preferred lower alkynyl groups which $R_1$, $R_2$, $R_3$, $R_4$, $R_5$, $R_6$, $R_7$, $R_8$, $R_9$ g $R_{10}$, $R_{11}$, $R_{12}$, $R_{13}$ and $R_{14}$ may represent include $C_2$, $C_3$, $C_4$, $C_5$, $C_6$, $C_7$, $C_8$, $C_9$, $C_{10}$, $C_{11}$, $C_{12}$, $C_{13}$ and $C_{14}$ alkynyl.

The term "lower alkynylene" is to be construed accordingly.

The term "aryl" includes six to ten-membered carbocyclic aromatic groups, such as phenyl and naphthyl, which groups are optionally substituted by one or more substituents selected from fluoro, cyano, nitro, lower alkyl (i.e. alkaryl), $OR_5$, $C(O)R_6$, $C(O)OR_7$, $C(O)NR_8R_9$ and $NR_{10}R_{11}$.

The term "aralkyl" includes aryl groups joined to the porphyrin ring via a lower alkyl group.

A second aspect of the invention provides use of a compound of formula II in the preparation of a medicament for killing or attenuating the growth of microorganisms by a method which does not comprise exposing the compound to a photodynamic therapy light source or a sonodynamic therapy ultrasound source:

II

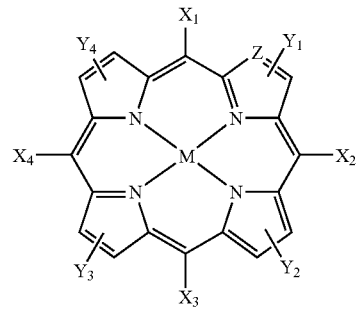

wherein M is a metallic element or a metalloid element and $X_1$, $X_2$, $X_3$, $X_4$, $Y_1$, $Y_2$, $Y_3$, $Y_4$ and Z are as defined above.

Preferably, in the first and second aspects of the invention the medicament is for killing or attenuating the growth of microorganisms by a method which does not comprise exposing the compound to a stimulus which activates antimicrobial activity.

By "a stimulus which activates antimicrobial activity" we mean a stimulus which increases the ability of the compound to kill or attenuate the growth of microbial agents, such as irradiation with a photodynainic therapy light source or an ultrasound source. In other words, the medicament exhibits innate antimicrobial activity, i.e. the medicament (and specifically the active compound therein) is intrinsically active Such activity may be determined by methods well knowarn in the art; for example, see Example B.

Hence, the medicament is for killing or attenuating the growth of microorganisms by a method other than photodynamic or sonodynamic therapy. However, it will be appreciated that methods for killing or attenuating the growth of microorganisms wherein the medicament is exposed to normal ambient light (i.e. sunlight or artificial ambient light) are not excluded.

Preferably, the medicament is exposed to light/radiation of intensity less than 10 mW/cm$^2$, for example less than 20 mW/cm$^2$, less than 25 mW/cm$^2$, less than 30 mW/cm$^2$ (i.e. less than 300 W/m$^2$) less than 40 mW/cm$^2$, less than 50 mW/cm$^2$, less than 60 mW/cm$^2$, less than 70 mW/cm$^2$, less than 80 mW/cm$^2$, less than 90 mW/cm$^2$ or less than 100 mW/cm$^2$.

Advantageously, the medicament is exposed to light/radiation dose of less than 100 J/cm$^2$, for example less than 90 J/cm$^2$, less than 80 J/cm$^2$, less than 70 J/cm$^2$, less than 60 J/cm$^2$, less than 50 J/cm$^2$, less than 40 j/cm$^2$, less than 30 J/cm$^2$, less than 20 J/cm$^2$ or less than 10 J/cm$^2$.

It will be further appreciated by persons skilled in the art that the medicament may be for use in a treatment regime that exploits both its innate activity and its photodynamic and/or sonodynamic activity. For example, the medicament may first be used in the absence of an activating stimulus, such that its innate antimicrobial activity is exploited, and subsequently exposed to an activating stimulus such that its photodynamic and/or sonodynamic activity is exploited.

The term "metallic element" is intended to include a divalent or trivalent metallic element. Preferably the metallic element is diamagnetic. More preferably, the metallic element is selected from Zn (II), Cu (II), La (III), Lu (III), Y (III), In (III) Cd (II), Mg (II), Al(III), Ru, Ni(II), Mn(III), Fe(III) and Pd(II). Most preferably, the metallic element is Ni(II), Mn(III), Fe(III) or Pd(II).

The term "metalloid" is intended to include an element having physical and chemical properties, such as the ability to conduct electricity, that are intermediate to those of both metals and non-metals. The term "metalloid element" includes silicon (Si) and germanium (Ge) atoms which are optionally substituted with one or more ligands.

It will be appreciated that the terms metallic element and metalloid element include a metal element or a metalloid element having a positive oxidation state, all of which may be substituted by one or more ligands selected from fluoro, OH, $OR_{15}$ wherein $R_{15}$ is lower alkyll, lower alkenyl, lower alkynyl, aralkyl, aryl or alkaryl as defined above (wherein aryl and alkaryl are mono-substituted).

The compounds of formulae I and II comprise at least one cationic group. Thus, the compounds of the invention may carry a net positive charge, for example a charge of +1, +2, +3, +4, +5, +6 or more. In a preferred embodiment, the compounds carry a net charge of less than +4, for example +1, +2 or +3. In a particularly preferred embodiment, the compounds carry a net charge of +2.

It will be appreciated by persons skilled in the art that compounds of formulae I and II may be counterbalanced by counter-anions. Exemplary counter-anions include, but are not limited to, halides (e.g. fluoride, chloride and bromide), sulfates (e.g. decylsulfate). nitrates, perchlorates, sulfonates (e.g. methane sulfonate) and trifluoroacetate. Other suitable counter-anions will be well known to persons skilled in the art. Thus, pharmaceutically, and/or veterinarily, acceptable derivatives of the compounds of formulae I and II, such as salts and solvates, are also included within the scope of the invention. Salts which may be mentioned include: acid addition salts, for example, salts formed with inorganic acids such as hydrochloric, hydrobromic, sulfuric and phosphoric acid, with carboxylic acids or with organo-sulfonic acids; base addition salts; metal salts formed with bases, for example, the sodium and potassium salts.

It will be further appreciated by skilled persons that the compounds of formula I may exhibit tautomerism. All tautomeric forms and mixtures thereof are included within the scope of the invention.

Compounds of formulae I and II may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively, the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

In a preferred embodiment of the first and second aspects of the invention, Z is —CH.

A characterising feature of the first and second aspects of the invention is that at least one of substituent groups $X_1$, $X_2$, $X_3$ and $X_4$ is a quaternary ammonium cationic group of the formula $-L-R_1-N^+(R_2)(R_3)R_4$, as defined above. Preferably, none of $X_1$, $X_2$, $X_3$ and $X_4$ is an anilinium or a pyridinium cationic group.

In a preferred embodiment, $R_1$ is an unsubstituted lower alkylene, lower alkenylene or lower alkynylene group.

Advantageously, $R_1$ is a straight-chain lower alkylene group of formula:

$$-(CH_2)_m-.$$

Preferably, 'm' is an integer between 1 and 20. More preferably, 'm' is an integer between 1 and 10, for example between 1 and 6, between 1 and 5, between 1 and 4 or between 1 and 3. Preferred straight-chain lower alkylene groups which $R_1$ may represent include groups of the above formula wherein m is 2, 3, 4, 5, 6, 7, 8, 9 or 10. Most preferably, 'm' is 2 or 3.

The remaining three substituent groups of the quaternary ammonium moiety, i.e. $R_2$, $R_3$ and $R_4$, may be the same or different and are selected from H, lower alkyl, lower alkenyl or lower alkynyl, the latter three of which are optionally substituted by one or more substituents selected from lower alkyl, $OR_5$, $C(O)R_6$, $C(O)OR_7$, $C(O)NR_8R_9$, $NR_{10}R_{11}$, and $N^+R_{12}R_{13}R_{14}$.

In a preferred embodiment, $R_2$, $R_3$ and/or $R_4$ are lower alklyl, lower alkenyl or lower alkynyl group.

Preferably, $R_2$, $R_3$ and/or $R_4$ are unsubstituted lower alkyl groups.

Optionally, at least one of $R_2$, $R_3$ and $R_4$ is an alkyl group which is substituted with a primary, secondary or tertiary amine group or a quaternary ammonium group.

In a preferred embodiment of the first and second aspects of the invention, $R_1$ is $-(CH_2)_3-$, $R_2$ and $R_3$ are $CH_3$ and $R_4$ is $-(CH_2)_3-N(CH_3)_2$.

In an alternative preferred embodiment of the first and second aspects of the invention, $R_1$ is $-(CH_2)_3-$, and $R_2$, $R_3$ and $R_4$ are each $CH_3$.

In a further alternative preferred embodiment of the first and second aspects of the invention, $R_1$ is $-(CH_2)_3-$, and $R_2$, $R_3$ and $R_4$ are each $C_2H_5$.

Advantageously, at least one of $X_1$, $X_2$, $X_3$ and $X_4$ is a cationic group as defined above and at least one of $X_1$, $X_2$, $X_3$ and $X_4$ is a hydrogen atom.

Preferably, each of $X_1$, $X_2$, $X_3$ and $X_4$ is a hydrogen atom or a cationic group as defined above.

Conveniently, the pK values of any primary, secondary or tertiary amine groups, if present in the compounds of the invention, is greater than 8 to ensure that the group is protonated when in a physiological environment.

The quaternary ammonium cationic group is optionally joined to the porphyrin ring via a linking moiety, L.

Preferred linking moieties, L, include phenoxy, phenylene, sulfonyl amido, aminosulfonyl, sulfonylimino, phenylsulfonylamido, phenyl-aminosulfonyl, urea, urethane and carbamate linking moieties.

In a preferred embodiment, the quaternary ammonium cationic group is joined to the porphyrin ring via a phenoxy linker.

Thus, $X_1$, $X_2$, $X_3$ and/or $X_4$ may have the following formula:

$$\text{Ar}-(OR)_n$$

wherein R is $R_1-N+(R_2)(R_3)R_4$, as defined above, and 'n' is an integer between 1 and 3.

In an alternative preferred embodiment, the quaternary ammonium cationic group is joined to the porphyrin ring via a phenylene linker.

Thus, $X_1$, $X_2$, $X_3$ and/or $X_4$ may have the following formula:

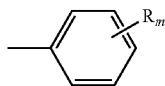

wherein R is $R_1$—$N^+(R_2)(R_3)R_4$, as defined above, and 'm' is an integer between 1 and 3.

Preferably, 'm' is 2, and most preferably 1.

In an alternative preferred embodiment, $X_1$, $X_2$, $X_3$ and/or $X_4$ may have the following formula:

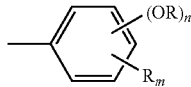

wherein R is $R_1$—$N^+(R_2)(R_3)R_4$, 'n' and 'm' are as defined above, and 'n+m' is between 1 and 3.

Advantageously, L comprises a benzene ring (e.g. phenoxy, phenylene, phenylsulfonylamido or phenylamino-sulfonyl) mono-substituted at the para-position. Alternatively, L may be mono- or di-substituted at meta- or ortho-positions. L may also be bothpara- and ortho-substituted.

In an alternative preferred embodiment, the quaternary ammonium cationic group is joined directly to the porphyrin ring, i.e. L is absent.

In a preferred embodiment of the first and second aspects of the invention, the compound comprises two cationic groups, as defined above, on opposite sides of the porphyrin ring, i.e. at ring positions 5 and 15 or ring positions 10 and 20. For example, $X_1$ and $X_3$ may be a hydrogen atom, a lipophilic moiety, a phenyl group, a lower alkyl, alkaryl or aralkyl group, and $X_2$ and $X_4$ may be cationic groups, or vice versa. Preferably, $X_1$ and $X_3$ are both a hydrogen atom and $X_2$ and $X_4$ are both a cationic group, or vice versa.

Alternatively, the compound may comprise two cationic groups, as defined above, on neighbouring positions of the porphyrin ring, i.e. at ring positions 5 and 10. or ring positions 10 and 15. or ring positions 15 and 20 or ring positions 20 and 5. For example, $X_1$ and $X_2$ may be hydrogen and $X_3$ and $X_4$ may be cationic groups, or $X_2$ and $X_3$ may be hydrogen and $X_4$ and $X_1$ may be cationic groups, etc.

It will be appreciated by persons skilled in the art that additional isomeric structural possibilities arise when Z represents nitrogen. Such possibilities are included within the scope of the present invention.

In a further preferred embodiment of the first and second aspects of the invention, the compound is substituted on one or more of its constituent pyrrole rings. Thus, $Y_1$, $Y_2$, $Y_3$ and $Y_4$ may be absent or independently represent aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)NR_8R_9$, $NR_{10}R_{11}$ and $N^+R_{12}R_{13}R_{14}$. It will be appreciated by skilled persons that $Y_1$, $Y_2$, $Y_3$ and/or $Y_4$ may comprise cyclic groups, which may be saturated or aromatic. For example, one or more of the pyrrole rings may be substituted to form an iso-indole group, i.e. $Y_1$, $Y_2$, Y3 and/or $Y_4$ together with the pyrrole ring to which they are attached may be cyclic.

In an alternative preferred embodiment of the first and second aspects of the invention, $Y_1$, $Y_2$, $Y_3$ and $Y_4$ are absent. Thus, the porphyrin ring is preferably substituted only at one or more of positions 5, 10, 15 or 20.

In a further preferred embodiment of the first and second aspects of the invention, at least one of $X_1$, $X_2$, $X_3$ and X4 is or comprises a lipophilic moiety.

By 'lipophilic moiety' we include moieties having a partition coefficient between 1-n-octanol and water expressed as log P of greater than 1.0 at physiological pH and 25° C.

Conveniently, the lipophilic moiety is a saturated, straight-chain alkyl group of formula —$(CH_2)_pCH_3$, or an equivalent alkylene group of formula —$(CH_2)_p$—, wherein 'p' is an integer between 1 and 22, for example between 1 and 18. Preferably, 'p' is between 1 and 18, more preferably between 2 and 16, between 4 and 16, between 6 and 18, between 8 and 16 or between 4 and 12. Most preferably, 'p' is between 10 and 12.

It will be appreciated that $X_1$, $X_2$, $X_3$ and/or $X_4$ may be a cationic group, as defined above, which also comprises a lipophilic moiety.

In an alternative preferred embodiment of the first and second aspects of the invention, none of $X_1$, $X_2$, $X_3$ and $X_4$ is a lipophilic moiety.

Advantageously, the compounds used in the first and second aspects of the invention are soluble in water. Preferably, the compounds may be dissolved in water to a concentration of at least 5 µg/l, for example at least 10 µg/l, 15 µg/l or 20 µg/l. More preferably, the compounds may be dissolved in water to a concentration of at least 100 µg/l, for example 200 µg/l, 300 µg/l, 400 µg/l, 500 µg/l, 1 mg/ml, 5 mg/ml, 10 mg/ml, 20 mg/ml, 50 mg/ml or 100 mg/ml.

Conveniently, the compounds used in the first and second aspects of the invention exhibit selective toxicity to microbial agents. By 'selective' we mean the compound is preferentially toxic to one or more microorganisms (such as bacteria, mycoplasmas, yeasts, fungi and/or viruses) compared to mammalian, e.g. human, host cells. Preferably, the toxicity of the compound to a target microorganism is at least two-fold greater than the toxicity of that compound to mammalian cells, more preferably at least three-fold, at least four-fold, at least five-fold, at least six-fold, at least eight-fold, at least ten-fold, at least fifteen-fold or at least twenty fold. Most preferably, the compound of the invention is substantially non-toxic to mammalian cells.

In this way, when the compounds are used to treat bacterial infections, for example, dosing regimes can be selected such that bacterial cells are destroyed with minimal damage to healthy host tissue. Thus, the compounds for use in the first and second aspects of the invention preferably exhibit a 'therapeutic window'.

In a preferred embodiment, the compound is toxic to the target microorganism (e.g. bacterial cells) at low doses. Preferably, the compound is toxic to the target microorganism at a concentration of less than 10 µM, for example less than 1 µM, less than 0.1 µM, less than 0.01 µM, less than 0.005 µM or less than 0.001 µM (see Example B).

Preferred compounds for use in the first and second aspects of the invention include the following:

(a) 5,15-bis-(4-{3-[(3-Dimethylamino-propyl)-dimethyl-ammonio]-propyloxy}-phenyl)-porphyrin dichloride ("Compound 8")

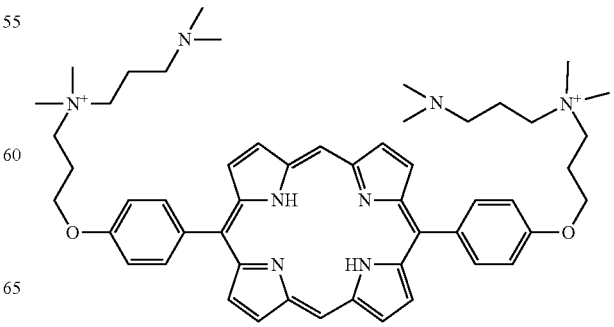

Preferably, this compound is provided as a dichloride or tetrachloride salt.

(b) 5,15-bis-[4-(3-Triethylammonio-propyloxy)-phenyl]-porphyrin dichloride ("Compound 9")

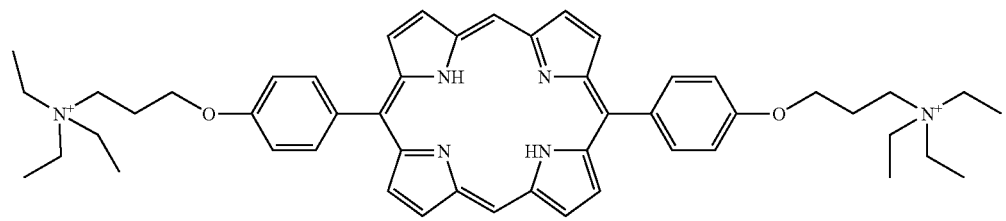

Preferably, this compound is provided as da dichloride salt.

(c) 5.15-bis-[3-(3-Trimethylammonio-propyloxy)-phenyl]-porphyrin dichloride ("Compound 12");

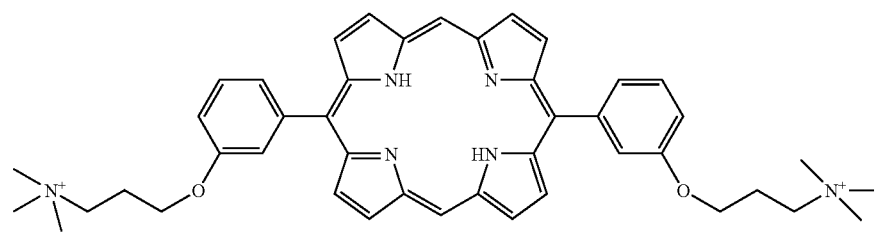

Preferably, this compound is provided as a dichloride salt.

(d) 5,15-bis-[4-(3-Trimethylammonio-propyloxy)-phenyl]-porphyrin dichloride ("Compound 10");

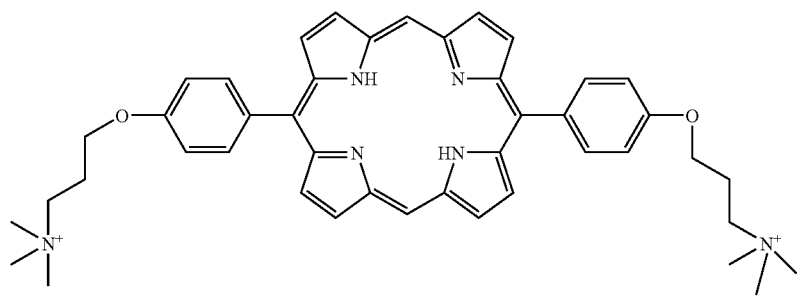

Preferably, this compound is provided as a dichloride salt.

(e) 5-[3,5-bis-(3-Trimethylammonio-propyloxy)-phenyl]-15-undecyl-porphyrin dichloride ("Compound 6");

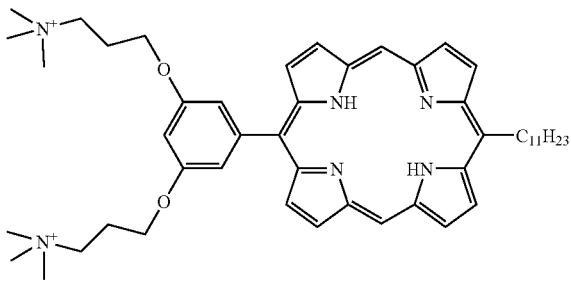

Preferably, this compound is provided as a dichloride salt.

(f) 5-{4-[3-Dimethyl-(3-dimethylaminopropyl)-ammonio-propyloxy]phenyl}-15-(4-dodecyloxy-phenyl)-porphyrin chloride ("Compound 23");

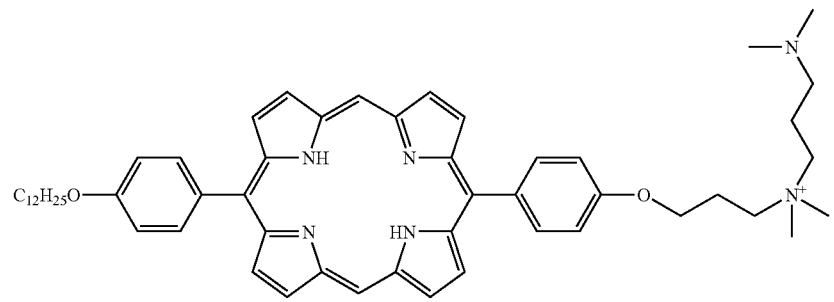

Preferably, this compound is provided as a chloride or dichloride salt.

(g) 3-[({3-[(3-{4-[15-(4-Dodecyloxy-phenyl)-porphyrin-5-yl]-phenoxy}-propyl)-dimethyl-ammonio]-propyl}-dimethyl-ammonio)-propyl]-trimethyl-ammonium trichloride ("Compound 25");

Preferably, this compound is provided as a trichloride salt.

(h) 5,15-bis-[3-(3-Trimethylammonio-propyloxy)-phenyl]-10-undecyl-porphyrin dichloride ("Compound 28");

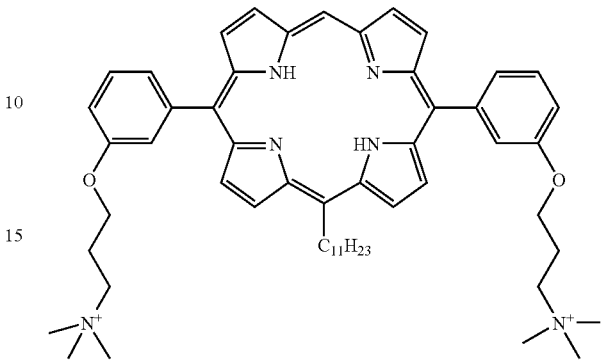

Preferably, this compound is provided as a dichloride salt.

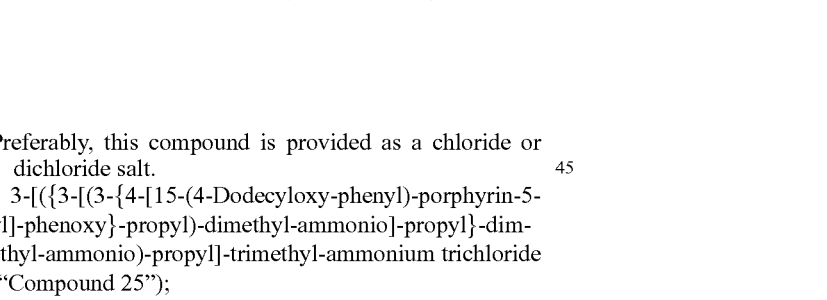

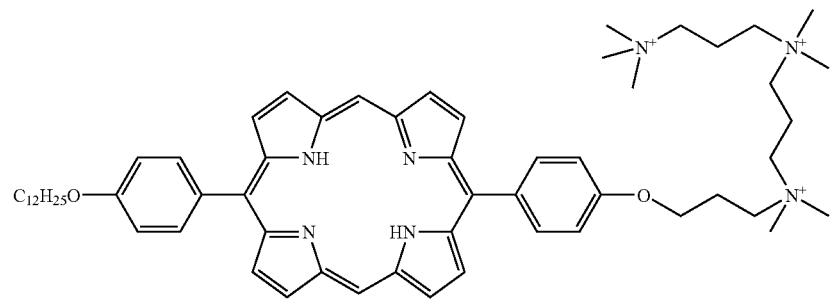

(i) 5-{4-[3-Dimethyl-(3-trimethylammonio-propyl)-ammonio-propyloxy]-phenyl}-15-(4-dodecyloxy-phenyl)-porphyrin dichloride ("Compound 31"); and

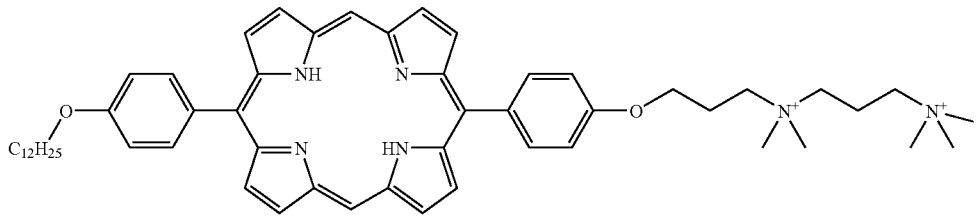

Preferably, this compound is provided as a dichloride salt.

(j) 5-[4-(3-Dimethyldecyl-ammoniopropyloxy)-phenyl]-15-{4-[3-dimethyl-(3-dimethylaminopropyl)-ammoniopropyloxy]-phenyl}-porphyrin dichloride ("Compound 32").

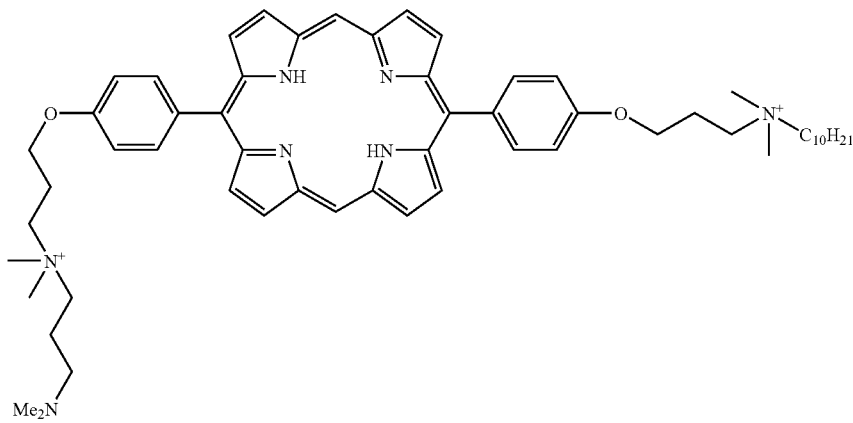

Preferably, this compound is provided as a dichloride salt.

It will be appreciated that the above compounds may alternatively be in a metallated form, i.e. they may comprise a chelated metallic element or metalloid element within the porphyrin ring.

The medicament as prepared according to the first or second aspects of the invention may be formulated at various concentrations, depending on the efficacy/toxicity of the compound being used and the indication for which it is being used. Preferably, the medicament comprises the compound at a concentration of between 0.1 µM and 1 mM, more preferably between 1 µM and 100 µM, between 5 µM and 50 µM, between 10 µM and 50 µM, between 20 µM and 40 µM and most preferably about 30 µM. For in vitro applications, formulations may comprise a lower concentration of a compound, for example between 0.0025 µM and 1 µM.

It will be appreciated by persons skilled in the art that the compound used in the first or second aspects of the invention will generally be administered in admixture with a suitable pharmaceutical excipient diluent or carrier selected with regard to the intended route of administration and standard pharmaceutical practice (for example, see Remington: The Science and Practice of Pharmacy, 19$^{th}$ edition, 1995, Ed. Alfonso Gennaro, Mack Publishing Company, Pennsylvania, USA). Suitable routes of administration are discussed below, and include topical, intravenous, oral, pulmonary, nasal, aural, ocular, bladder and CNS delivery.

For example, for application topically, e.g to the skin or a wound site, the compounds can be administered in the form of a lotion, solution, cream, gel, ointment or dusting powder (for example, see Remington, supra, pages 1586 to 1597). Thus, the compounds can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, e-lauryl sulphate, an alcohol (e.g. ethanol, cetearyl alcohol, 2-octyldodecanol, benzyl alcohol) and water.

In a preferred embodiment, the medicament (e.g. lotion, solution, cream, gel or ointment) is water-based.

Formulations suitable for topical administration in the mouth further include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

The medicament as prepared according to the first or second aspects of the invention may also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromnethane, dichlorotetra-fluoroethane, a hydrofluoroalkane such as 1,1,1,2-tetrafluoroethane (HFA 134A$^3$ or 1,1,1,2,3,3,3-heptafluoropropane (HFA 227EA$^3$) carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains at least 1 mg of a compound for delivery to the patient. It will be appreciated that the overall dose with an aerosol will vary from patient to patient and from indication to indication, and may be administered in a single dose or, more usually, in divided doses throughout the day.

Alternatively, other conventional administration routes known in the art may also be employed; for example the medicament as prepared according to the first or second aspects of the invention may be delivered orally, buccally or sublingually in the form of tablets, capsules, ovules, elixirs, solutions or suspensions, which may contain flavouring or colouring agents, for immediate-, delayed- or controlled-release applications. The medicament may also be administered intra-ocularly (see below), intra-aurally or via intracavernosal injection.

The medicament may also be administered parenterally, for example, intravenously, intra-arterially, intraperitoneally, intrathecally, intraventricularly, intrasternally, intracranially, intramuscularly or subcutaneously (including via an array of fine needles or using needle-free Powderject® technology), or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders granules and tablets of the kind previously described.

The medicament may also be administered by the ocular route, particularly for treating diseases of the eye. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For veterinary use, a compound is administered as a suitably acceptable formulation in accordance with normal veterinary practice and the veterinary surgeon will determine the dosing regimen and route of administration which will be most appropriate for a particular animal.

In a preferred embodiment of the first and second aspects of the invention, the medicament is for oral or parenteral administration. Thus, the medicaments are preferably for treating systemic microbial infections.

The medicaments may be stored in any suitable container or vessel known in the art. It will be appreciated by persons skilled in the art that the container or vessel should preferably be airtight and/or sterilised. Advantageously, the container or vessel is made of a plastics material, such as polyethylene.

It will be appreciated that the medicaments as prepared according to the first or second aspects of the invention may be used for killing a number of types of microorganism, including bacteria, mycoplasmas, yeasts, fungi and/or viruses. It will be further appreciated that the medicaments may be used to prevent and/or treat infection with such microorganisms, i.e. the medicaments are suitable for prophylactic and/or therapeutic treatment. For example, the medicament may be used to prevent or reduce the spread or transfer of a pathogen to other subjects, e.g. patients, healthcare workers, etc.

Preferably, the medicaments as prepared according to the first or second aspects of the invention are for use in the curative and/or prophylactic treatment of bacterial infections such as Gram positive cocci (e.g. *Streptococcus*), Gram negative cocci (e.g. *Neisseria*), Gram positive bacilli (e.g. *Corynebacterium* species), Gram negative bacilli (e.g. *Escherichia coli*), acid-fast bacilli (e.g. a typical *Mycobacterium*) and including infections causing abscesses, cysts, blood infection (bacteraemia), dermatological infections, wound infections, arthritis, urinary tract infections, pancreatitis, pelvic inflammatory disease, peritonitis, prostatitis, infections of the vagina, oral cavity (including dental infections), eye and/or ear, ulcers and other localised infections; actinomyces infections; fungal infections such as *Candida albicans, Aspergillus* and *Blastomyces*; viral infections such as HIV, encephalitis, gastro-enteritis, haemorrhagic fever, hantavirus, viral hepatitis, herpesvirus (e.g. cytomegalovirus, Epstein-Barr, herpesvirus simiae, herpes simplex and varicella-zoster); protozoal infections such as amoebiasis, babesiosis, coccidiosis, cryptosporidiosis, giardiasis, Leishmaniasis, Trichomoniasis, toxoplasmosis and malaria; helminthic infections such as caused by nematodes, cestodes and trematodes, e.g. ascariasis, hookworm, lymphatic filariasis, onchocerciasis, schistosomiasis and toxocariasis; prion diseases; and inflammatory diseases such as soft-tissue rheumatism, osteoarthritis, rheumatoid arthritis and spondyloarthropathies.

More preferably, the medicaments are for use in the curative and/or prophylactic treatment of infections by Gram positive bacteria and/or Gram negative bacteria. Most preferably, the compounds of the invention are for use in the curative and/or prophylactic treatment of infections by Gram positive bacteria.

The medicaments are preferably used to kill microorganisms, e.g. bacteria, mycoplasmas, yeasts, fungi and viruses. The medicaments are particularly suitable for killing bacteria which have developed resistance to conventional antibiotic treatments, such as methicillin-resistant *Staphylococcus aureus* (MRSA).

It will be appreciated by persons skilled in the art that the medicaments are suitable to treat all microbial infections, regardless of whether the site of infection is light accessible or not. Hence, such medicaments may have utility to treat infections which are not able to be treated by conventional photodynamic therapy agents. Preferably, the microbial infection is on a light-inaccessible surface or in a light-inaccessible area.

Dosages of the compound in the medicaments as prepared according to the first or second aspects of the invention will depend on several factors; including the particular compound used, the formulation, route of administration and the indication for which the compound is used. Typically, however, dosages will range from 0.01 to 20 mg of compound per kilogram of body weight, preferably from 0.1 to 15 mg/kg, for example from 1 to 10 mg/kg of body weight.

In a preferred embodiment, the medicaments as prepared according to the first or second aspects of the invention are used in combination with conventional antimicrobial agents. For example the compounds may be used in combination with one or more of the following conventional antibiotics: antibacterial agents, for example natural and synthetic penicillins and cephalosporins, sulphonamides, erythromycin, kanomycin, tetracycline, chloramphenicol, rifampicin and including gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mezlocillin, pivampicillin, talampicillin hydrochloride, carfecillin sodium, piperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, latamoxef disodium, aztreonam, chlortetracycline hydrochloride, clomocycline sodium, demeclocydine hydrochloride, doxycycline, lymecycline, minocycline, oxytetracycline, amikacin, framycetin sulphate, neomycin sulphate, netilmicin, tobramycin, colistin, sodium fusidate, polymyxin B sulphate, spectinomycin, vancomycin, calcium sulphaloxate, sulfametopyrazine, sulphadiazine, sulphadimidine, sulphaguanidine, sulphaurea, capreomycin, metronidazole, tinidazole, cinoxacin, ciprofloxacin, nitrofurantoin, hexamine, streptomycin, carbenicillin, colistimethate, polymyxin B, furazolidone, nalidixic acid, trimethoprim-sulfamethox-azole, clindamycin, lincomycin, cycloserine, isoniazid, ethambutol, ethionamide, pyrazinamide and the like; anti-fungal agents, for example miconazole, ketoconazole, itraconazole, fluconazole, amphotericin, flucytosine, griseofulvin, natamycin, nystatin, and the like; and anti-viral agents such as acyclovir, AZT, ddI, amantadine hydrochloride, inosine pranobex, vidarabine, and the like.

In a further preferred embodiment, the medicaments comprise and/or are co-administered with penetration enhancing agents, such as poly-(ethyleneimine), or antibiotic agents which exhibit such penetration-enhancing capability (e.g. polymyxin or colistin).

The medicaments as prepared according to the first or second aspects of the invention are particularly suited for use in the curative or prophylactic treatment of one or more of the following indications:

Impetigo

Impetigo is a highly communicable infection. It is the most common infection in children.

Impetigo have two classic forms nonbullous and bullous. The nonbullous impetigo, also named impetigo contagiosa accounts for approximately 70% of cases. Lesions normally resolve in 2 to 3 weeks without treatment. Impetigo also may complicate other skin diseases such as scabies, varicella, atopic dermatitis, and Darier's disease.

(a) Nonbullous Impetigo

Type of bacteria

Nonbullous is an infection caused principally by Group A beta-haemolytic streptococci (*Strieptococcus pyogenes*), *Staphylococcus aureus*, or a combination of these two organisms (see Andrews' diseases of the skin: clinical dermatology 9th ed. (2000) edited by Odom RB editor Saunders p.312-4). Non-Group A (Group B, C, and G) streptococci may be responsible for rare cases of impetigo, and Group B streptococci are associated with impetigo in the newborn.

Type of Wounds

Nonbullous is a superficial, intraepidermal, unilocular vesiculopustular infection.

Lesions of nonbullous impetigo commonly begin on the skin of the face or extremities following trauma. As a rule, intact skin is resistant to impetiginazation.

The clinical presentation of impetigo evolves in an orderly fashion from a small vesicle or pustule, which progresses into honey-coloured crusted plaque. Lesions usually are less than 2 cm in diameter. Lesions tend to dry, leaving fine crusts without cicatrisation. Lesions are usually minimally symptomatic. Rarely, erythema associated with mild pain or slight pruritus may be present. The infection spreads to contiguous and distal areas through the inoculation of other wound from scratching.

Site of Bacteria

Nonbullous impetigo is a superficial streptococcal or staphylococcal infection which is localised to the subcorneal (just beneath the stratum corneum) layer of the skin (see FIG. 1). More particularly, infection in impetigo is confined histopathogically to highly differentiated, upper epidermal keratinoc)tes. Once the bacteria invade a break in the skin, they begin to multiply.

The histopathology is that of an extremely superficial inflammation about the funnel-shaped upper portion of the pilosebaceous follicles. A subcorneal vesicopustule is formed, containing a few scattered cocci, together with debris of polymorphonuclear leukocytes and epidermal cells. In the dermis, there is a mild inflammatory reaction—vascular dilatation, oedema, and infiltration of polymorphonuclear leukocytes (Andrews' diseases of the skin, supra., p.312-4).

(b) Bullous Impetigo

Type of Bacteria

Bullous impetigo is caused primarily by strains of *Staphylococcus aureus* which produce exfoliative toxins (Sadick et al., 1997, *Dermatologic Clinics* 15(2): 341-9).

Type of Wounds

Bullous impetigo is histologically characterised by subcorneal cleavage and infiltrate with polymorphonuclear leucocytes migrating through the epidermis and accumulating between granular and stratum corneum skin layers. Small or large superficial fragile bullae are present on the trunk and extremities.

Flaccid bullae and moist erosions with surrounding erythema are characteristic of this subcorneal infections. Often, only the remnants of ruptured bullae are seen at the time of presentation. The separation of the epidermis is due to an exotoxin produced by *Staphylococcus aureus*.

Sites of Bacteria

Bullous impetigo is a superficial staphylococcal infection that occurs in and just beneath the stratum corneum (see FIG. 1). Bullous impetigo is considered due to exfoliative toxin produced by some *Staphylococcus aureus* attached to stratum comeum cells.

Atopic Dermatitis (AD)

Atopic dermatitis, also named atopic eczema, is a chronic inflammation of the skin resulting in an itchy rash, especially in the flexures i.e. behind the knees, in front of the elbows, wrists, neck, and eyelids. Infection of the rash is common, and causes further inflammation and itch.

Eczema typically manifests in those aged 1-6 months. Approximately 60% of patients have their first outbreak by 1 year and 90% by 5 years. Onset of atopic dermatitis in adolescence or later is uncommon and should prompt consideration of another diagnosis. Disease manifestations vary with age.

Type of Bacteria

Bacteria and their superantigens contribute to the pathogenesis of AD.

*Staphylococcus aureus* colonises the skin of 90% of AD patients (chronic eczematous lesions) and only 5% of non-atopic patients. The colonisation density of *Staphylococcus aureus* can reach up to $10^7$ colony forming units $cm^{-2}$ without clinical signs of infection in patients with AD. In addition, the apparently normal non-lesional skin of atopic patients contains increased numbers of *Staphylococcus aureus*.

The reason for the overgrowth of *Staphylococcus aureus* in atopic dermatitis, though much less severely or not at all in diseases such as psoriasis, is not known. Protein A elicits a much less vigorous response in atopics than in normals or psoriatics, but this may be the result rather than a cause of colonisation. Attention has recently turned to the skin lipids and there is some evidence that fatty acids which may control staphylococcal colonisation are deficient in atopics.

Superantigens are a unique group of proteins produced by bacteria and viruses that bypass certain elements of the conventional, antigen-mediated immune sequence. Whereas conventional antigens activate approximately 0.01% to 0.1% of the body's T cells, a superantigen has the ability to stimulate 5% to 30% of the T-cell population. *S. aureus* may exacerbate or maintain skin inflammation in AD by secreting a group of exotoxins that act as superantigens. AD patients possess an altered skin barrier secondary to an insufficiency of ceramides within the stratum corneum. It has been proposed that penetration of the skin by these exotoxins may cause activation of T cells, macrophages, LCs, and mast cells, thereby leading to the release of cytokines and mast cell mediators.

It is conceivable that these events may provide the basis for inflammation in chronic AD. Speculation remains whether *S. aureus* colonisation and local superantigen secretion is a primary or secondary phenomenon in AD (Andrews' diseases of skin, Chap. 5, Atopic Dermatitis, Eczema. and non-infectious inmunodeficiency disorders, p.69-76).

Cutaneous viral, fungal, and bacterial infections occur more commonly in AD patients. Viral infections are consistent with a T cell defect and include herpes simplex (local or generalised, i.e. eczema herpeticum), molluscum contagiosum, and human papilloma virus. Superficial fungal infections with *Trichophyton rubrum* and *Pityrosporon ovale* also occur frequently. Bacterial infections, specifically those with *S. aureus*, are extremely common. Superinfection results in honey-coloured crusting, extensive serous weeping or folliculitis.

Type of Wounds

Acute lesions appear as erythematous papules, vesicles, and erosions; chronic disease consists of fibrotic papules and thickened, lichenified skin.

A finding of increasing numbers of pathogenic staphylococci is frequently associated with weeping, crusting, folliculitis and adenopathy. Secondary staphylococcal infection is frequent and local oedema and regional adenopathy commonly occur during atopic dermatitis. Impetigo can be a sort of secondary infection of atopic dermatitis.

The histology of atopic dermatitis ranges from acute spongiotic dermatitis to lichen simplex chronicus, depending on the morphology of the skin lesion biopsied.

Sites of Bacteria

*Staphylococcus aureus* cell walls exhibit receptors, the so-called adhesins, for epidermal and dermal fibronectin and fibrinogen. It has been demonstrated that the binding of *Staphylococcus aureus* was mediated by fibrinogen and fibronectin in AD patients. As the skin of AD patients lacks an intact *stratum corneum*, dermal fibronectin might be uncovered and increase the adherence of *Staphylococcus aureus*. Fibrillar and amorphous structures have been traced between *Staphylococcus aureus* cells and corneocytes and may results in a bacterial biofilm. It has been observed that *Staphylococcus aureus* penetrates into intracellular spaces suggesting that the skin surface lipids are deteriorated in AD patients (see Breuer K et al., 2002, *British Journal of Dermatology* 147: 55-61).

Ulcers

Skin ulcers, such as diabetic foot ulcers, pressure ulcers, and chronic venous ulcers, are open sores or lesions of the skin characterised by the wasting away of tissue and sometimes accompanied by formation of pus. Skin ulcers may have different causes, and affect different populations, but they all tend to heal very slowly, if at all, and can be quite difficult and expensive to treat.

Type of Bacteria

Superficial pressure ulcers are not associated with major infection problems. Aerobic microorganisms at low levels will contaminate pressure ulcers, but will not impede timely healing. However, deep full-thickness pressure ulcers can become secondarily infected, and osteomyelitis can occur. Those pressure ulcers with necrotic tissue contain high levels of aerobic and anaerobic microorganisms as compared to non-necrotic ulcers; foul smell is usually present when anaerobes invade the tissues. Thus, a treatment strategy is to clear necrotic tissue from the wound, producing a decrease in anaerobe presence.

The infections of pressure ulcers are typically polymicrobial and can contain *Streptococcus pyogenes*, enterococci, anaerobic streptococci, *Enterobacteriaece*, *Pseudomnonas aeruginosa*, *Bacteroides fragilis* and *Staphylococcus aureus*.

Type of Wounds

Stage I pressure ulcer: Nonblanchable erythema of intact skin, considered to be heralding lesion of skin ulceration.

Stage II pressure ulcer: Partial thickness skin loss involving the epidermis and/or dermis. The ulcer is superficial and presents clinically as an abrasion, blister, or shallow crater. Because the epidermis may be interrupted by an abrasion, blister, or shallow crater, the ulcer should be evaluated for signs of secondary infections.

Stage III: Full thickness skin loss involving dainage or necrosis of subcutaneous tissue which may extend down to, but not through, underlying fascia. The ulcer presents clinically as a deep crater with or without undermining of adjacent tissue.

Stage IV: Full thickness skin loss with extensive destruction, tissue necrosis, or damage to muscle bone, or supporting structures, such as tendons or joint capsules.

Sites of Bacteria

There are three microbiological states that are possible in a wound: contamination, colonisation and infection. Contamination is characterised as the simple presence of microorganisms in the wound but without proliferation. It is generally accepted that all wounds, regardless of aetiology, are contaminated. Colonisation is characterised as the presence and proliferation of microorganisms in the wound but without host reaction. Colonisation is a common condition in chronic wounds such as venous ulcers and pressure ulcers and does not necessarily delay the healing process. When bacteria invade healthy tissues and continue to proliferate to the extent that their presence and by-products elicit or overwhelm the host immune response, this microbial state is known as infection. The classic signs and symptoms of infection include local redness, pain and swelling, fever and changes in the amount and character of wound exudates.

Lung Infections

The medicaments of the invention are also suitable for treating a patient having an infectious disease of the lung. Lung infection can occur with a variety of bacterial genera and species, which include *Mycobacterium tuberculosis* (tuberculosis), *Pseudomonas* (primary cause of death of cystic fibrosis patients), *Streptococcus*, *Staphylococcus pneumoniae*, *Klebsiella*, *Toxoplasma*, etc. Lung infection can also occur with a variety of virus strains and opportunistic pathogens (fungi, parasites). As pathogens of the lung are increasingly resistant to classical antibiotic therapies, photodynamic therapy offers an alternative method for eliminating these harmful organisms.

The medicaments of the invention can be administered to the lung in a variety of ways. For example the compound can be administered by the respiratory tract (i.e. intra-tracheally, intra-bronchially, or intra-alveolarly) or through the body wall of the chest.

Further Indications

The medicaments of the invention are also suitable for the curative and/or prophylactic treatment of the following:

Systemic infections, bacteraemia (blood infection), periodontitis and other dental infections, treatment of tooth decay and against plaque, urinary tract infections, vaginal infections, treatment of all microorganism diseases including prions, viral infections, yeast infections, throat infections, stomach ulcers (caused by *Heliobacter pylori*), infections of burn sites and skin grafts, otitis (ear infection), bacterial conjunctivitis and other eye infections, infected bones exposed during surgical procedures, and bioterrorism attacks.

Suitable veterinary applications include the curative and/or prophylactic treatment of foot-and-mouth disease, BSE and animal parasite infestations.

Thus, further aspects of the invention provide the following:
(i) Use of a compound as described above in the preparation of a medicament for the curative and/or prophylactic treatment of a dermatological infection;
(ii) Use of a compound as described above in the preparation of a medicament for the curative and/or prophylactic treatment of an infection of the lungs;
(iii) Use of a compound as described above in the preparation of a medicament for the curative and/or prophylactic treatment of a wound infection and/or an ulcer;
(iv) A method for treating a patient in need of treatment with a antimicrobial agent comprising administering to the patient a compound as described above, wherein the method does not comprise irradiating the compound with a stimulus which activates antimicrobial activity; and
(v) A method for treating a patient in need of treatment with an antimicrobial agent comprising administering to the patient a compound as described above, wherein the method comprises a first treatment phase during which the compound is not irradiated with a stimulus which activates antimicrobial activity, followed by a second treatment phase when the compound is irradiated with a stimulus which activates antimicrobial activity (such as ultrasound and/or light). Preferably, the first treatment phase lasts at least 10 minutes, for example at least 20 minutes, 30 minutes, 40 minutes, 50 minutes, 1 hour, 2 hours, 3 hours, 5 hours, 12 hours and 24 hours.

The medicaments prepared according to the first and second aspects of the invention may also be used to kill microorganisms in vitro. For example, the medicament may also be used in the form of a sterilising solution or wash to prevent the growth of microorganisms on a surface or substrate, such as in a clinical environment (e.g. surgical theatre) or a domestic environment (e.g. a kitchen work surface, washing clothes such as bed linen).

Preferably, such a medicament comprises the antimicrobial compound in solution at a concentration of 1 to 100 µg/ml.

Preferably, the solution further comprises a surface-active agent or surfactant. Suitable surfactants include anionic surfactants (e.g. an aliphatic sulphonate), amphoteric and/or zwitterionic surfactants (e.g. derivatives of aliphatic quaternary ammonium, phosphonium and sulfonium compounds) and nonionic surfactants (e.g. aliphatic alcohols, acids, amides or alkyl phenols with alkylene oxides)

Conveniently, the surface-active agent is present at a concentration of 0.5 to 5 weight percent.

The sterilising solutions are particularly suited for use in hospital environments. For example, the sterilising solutions may be used to sterilise surgical instruments and surgical theatre surfaces, as well as the hands and gloves of theatre personnel. In addition, the sterilising solutions may be used during surgery, for example to sterilise exposed bones. In all cases, the solution is applied to the surface to be sterilised. The medicament may also be used to disinfect blood and blood products and in the diagnosis of bacterial contamination or infection.

In both in vitro and in vivo uses, the medicament prepared according to the first and second aspects of the invention is preferably exposed to the target microorganisms (or surface/area to be treated) for at least five minutes. For example, the exposure time may be at least 10 minutes, 20 minutes, 30 minutes, 40 minutes, 50 minutes, 1 hour, 2 hours, 3, hours, 5 hours, 12 hours and 24 hours.

Preferred, non-limiting embodiments of the invention will now be described by way of example, with reference to the accompanying drawings in which.

NHDF were incubated with different concentrations of Compound 10 for 5 min, 1 h and 4 h (0 µM, 0.01 µM, 0.1 µM, 1.0 µM, 10 µM). Cells were then incubated for 24 h in the dark. Toxicity was tested by standard MTT-assay. Cell viability was normalised to one, which means, the values of control cells were normalised to one. Grey dotted line: 5 min incubation; black dotted: 1 h incubation; black line: 4 h incubation; (n=3, mean±SD).

Figure 3:
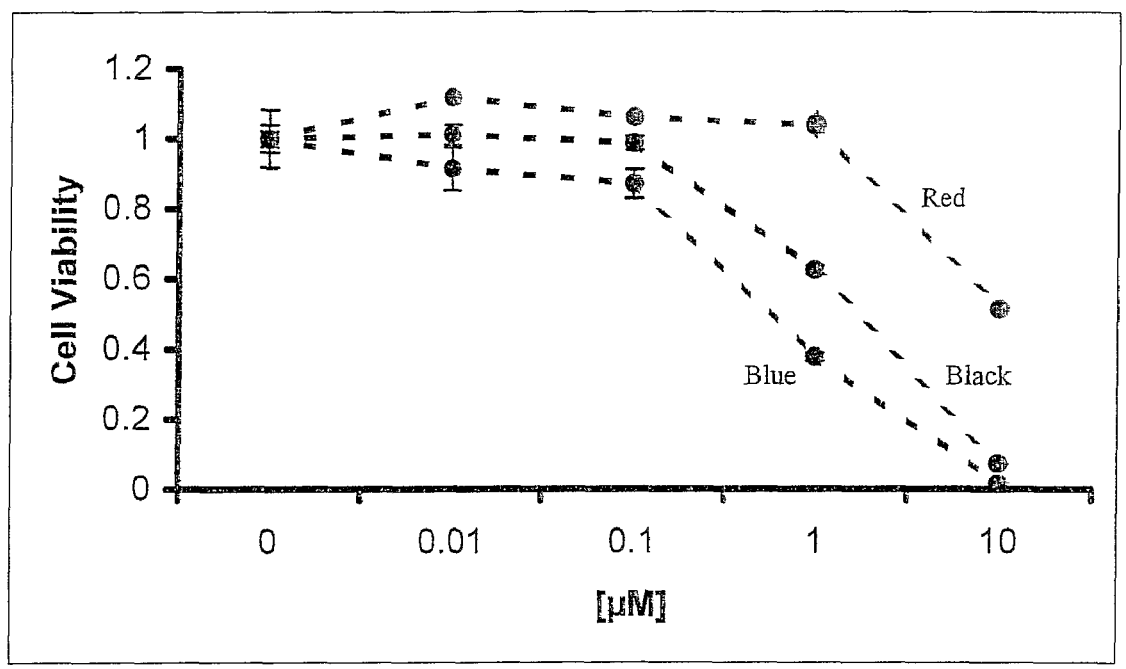

FIG. 3 shows cell toxicity of normal human epidermal keratinocytes after 5 minutes, 1 hour and 4 hours incubation with Compound 10. NHEK were incubated with different concentrations of Compound 10 for 5 min, 1 h and 4 h (0 µM, 0.01 µM, 0.1 µM, 1.0 µM, 10 µM). Cells were then incubated for 24 h in the dark. Toxicity was tested by standard MTT-assay. Cell viability was normalised to one, which means, the values of control cells were normalised to one. Red dotted line: 5 min incubation; black dotted: 1 h incubation; blue dotted: 4 h incubation only; (n=3, mean±SD).

Figure 4A:
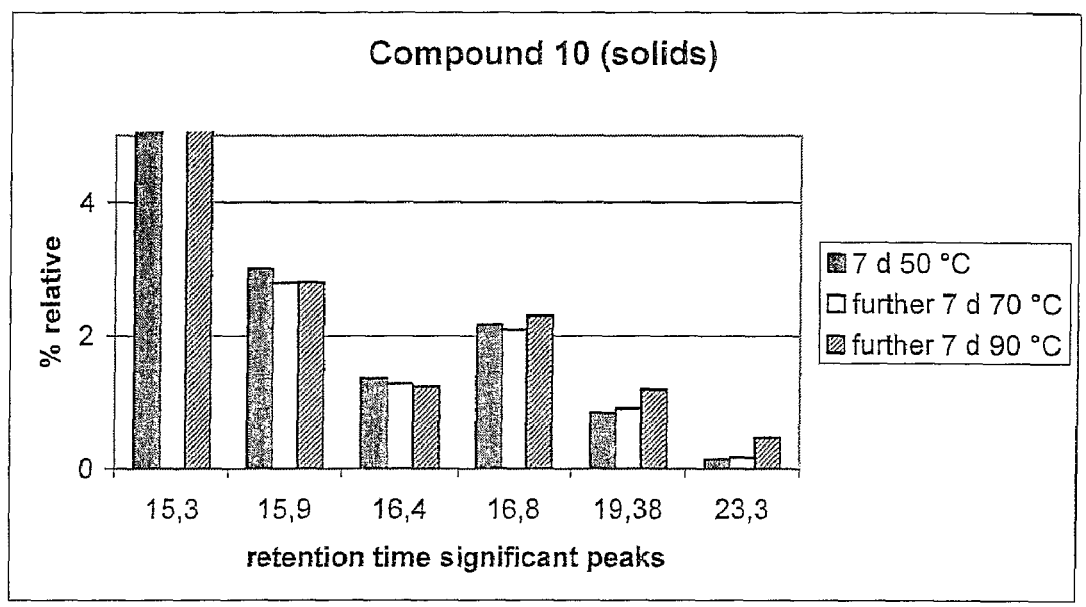
Figure 4B:
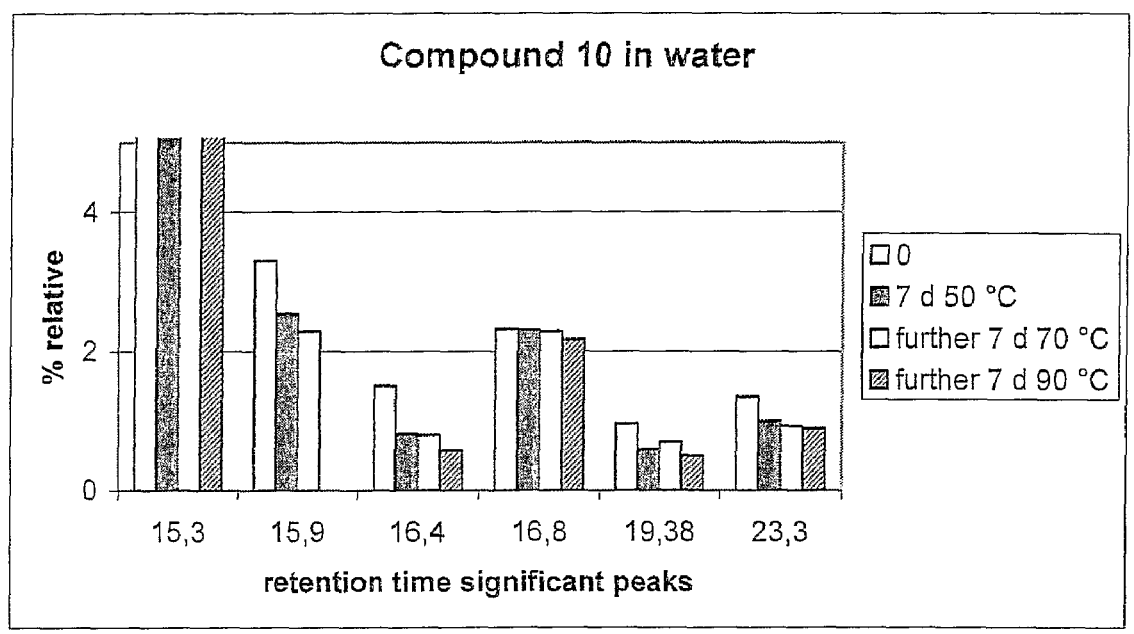
Figure 4C:
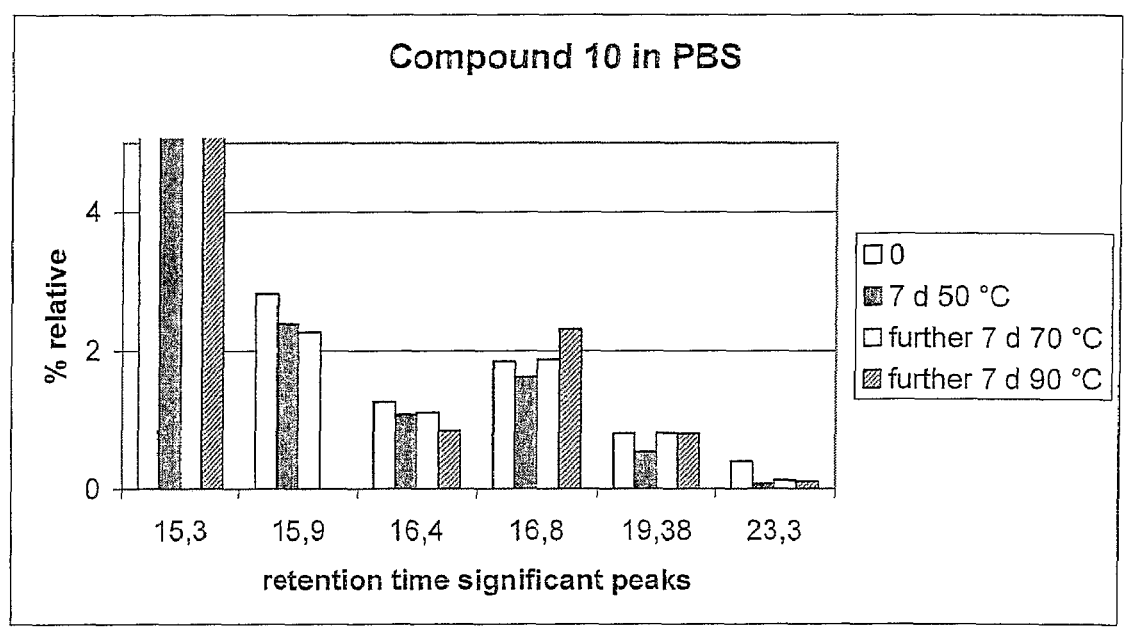

FIG. 4 shows the chemical stability of Compound 10 formulated (A) as a solid, (B) in water and (C) in PBS.

Figure 5:
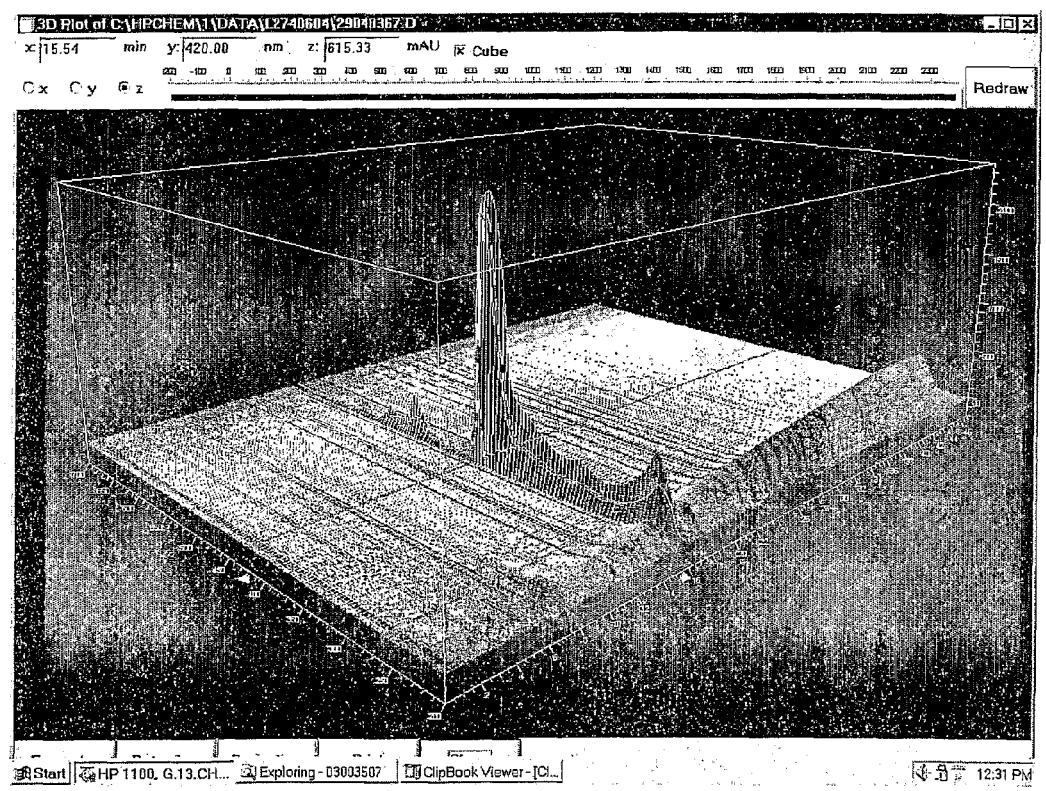
Figure 6A:
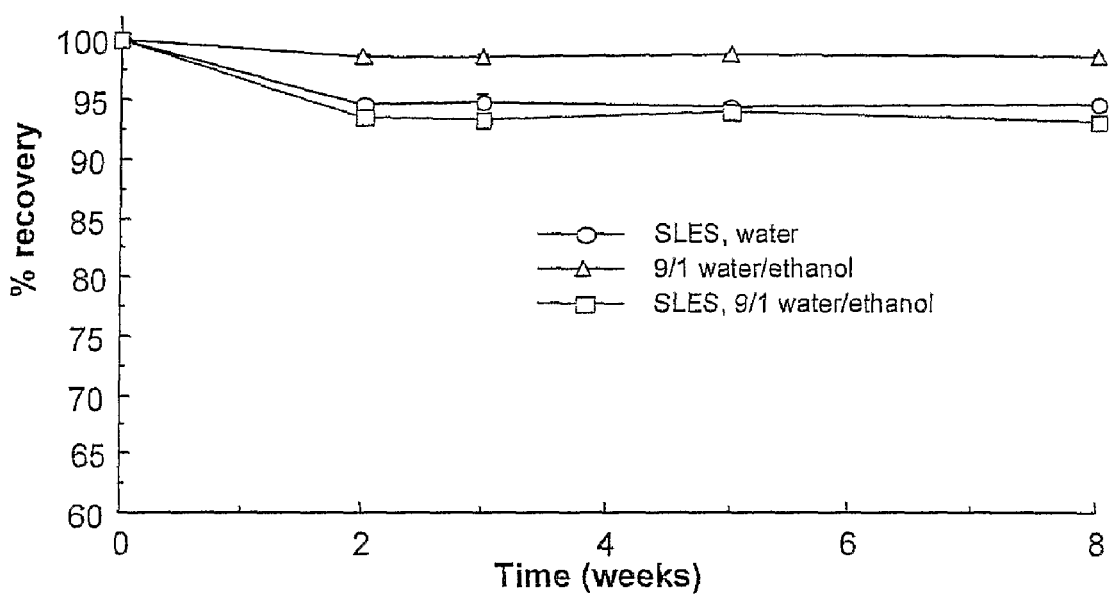
Figure 6B:
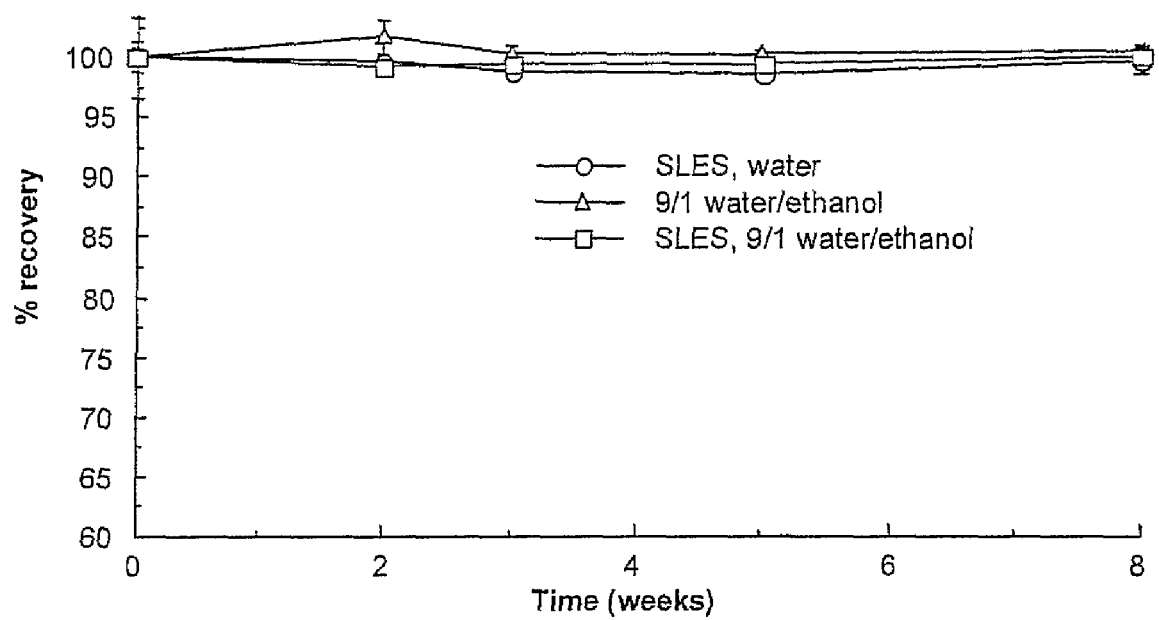
Figure 6C:
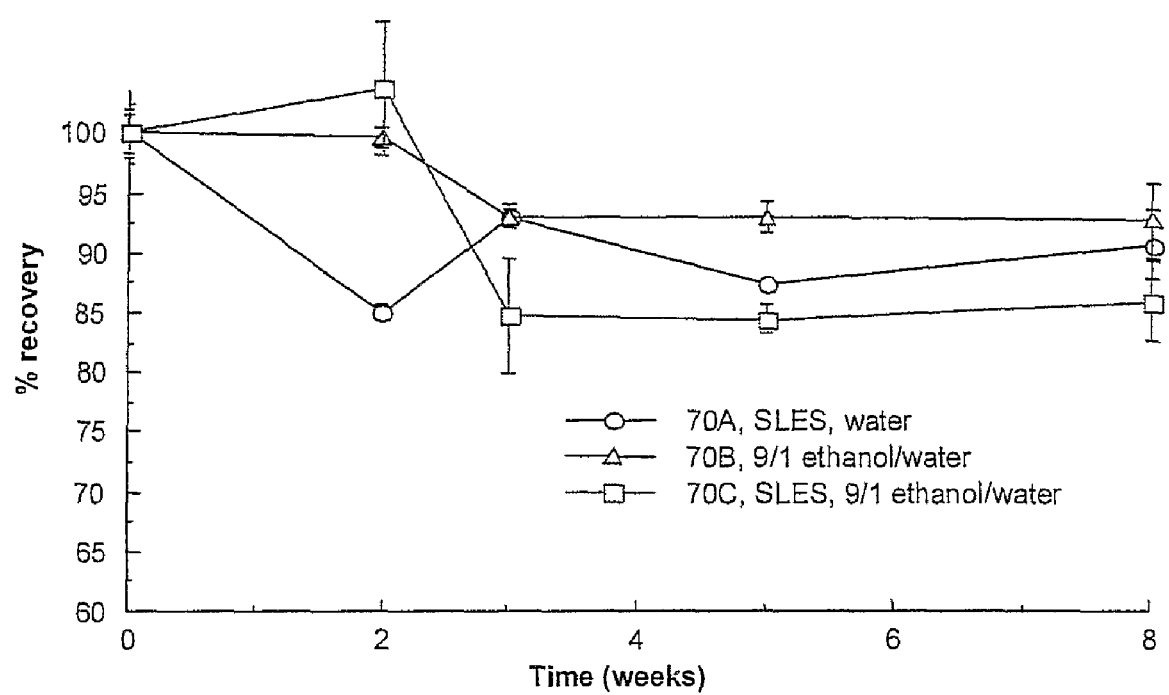
Figure 6D:
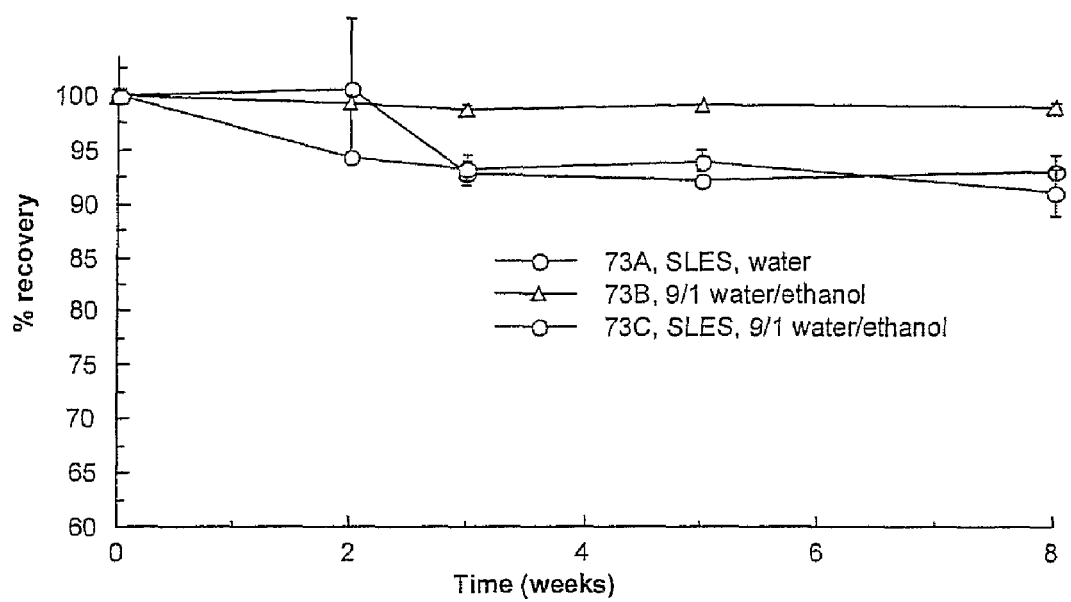

FIG. 5 shows a 3D plot of the stability (measured by HPLC) of Compound 10 after 21 days in PBS buffer.

FIG. 6 shows the stability over 8 weeks of various formulations of (A) Compound 1, (B) Compound 8, (C) Compound 12 and (D) Compound 10.

Figure 7A:
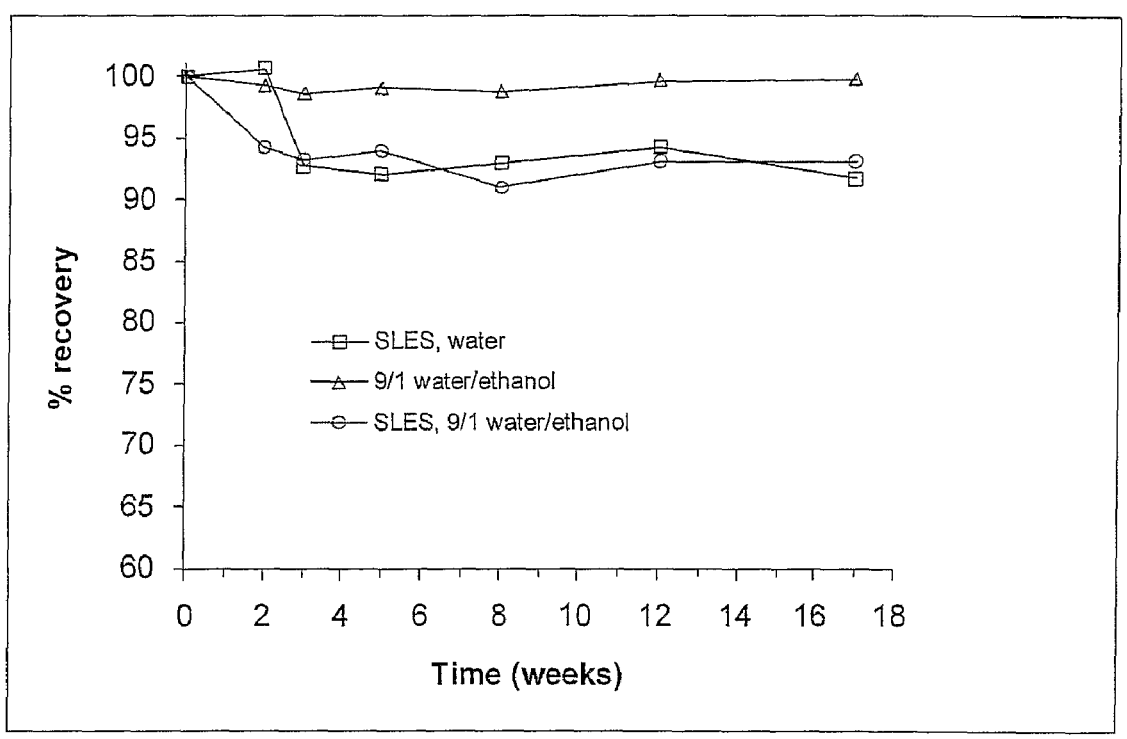
Figure 7B:
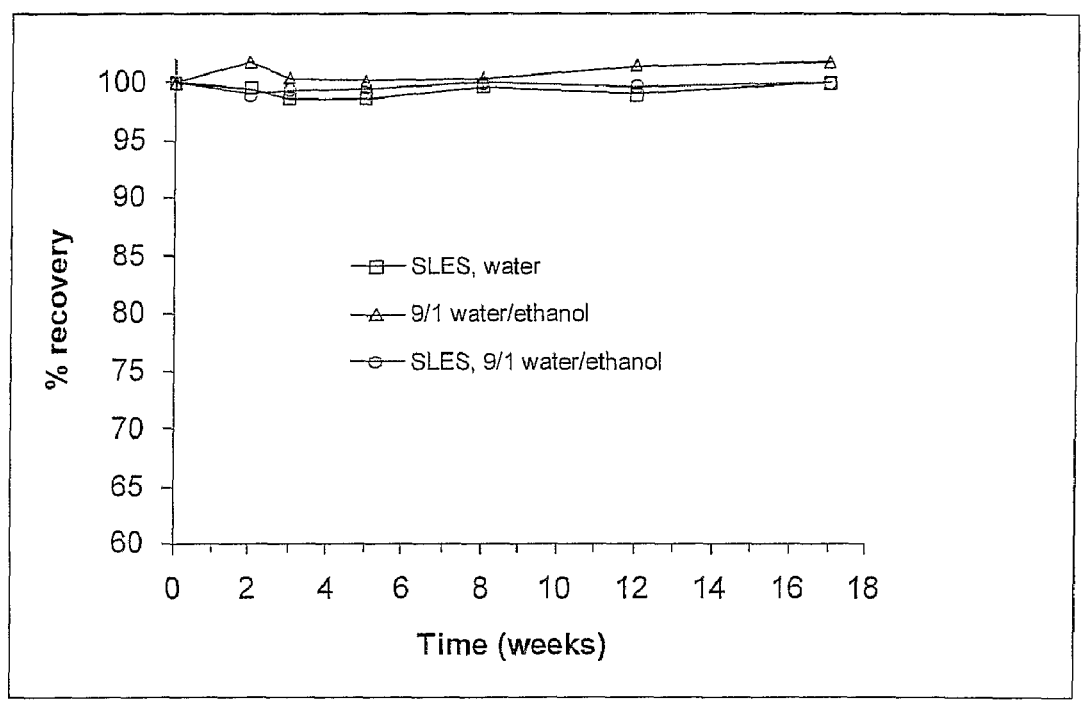

FIG. 7 shows the extended stability over 17 weeks of various formulations of (A) Compound 10 and (B) Compound 8.

EXAMPLES

Example A

Synthesis of Exemplary Compounds

Materials and Methods
NMR-Measurements

Proton NMR spectra were recorded on a Bruker B-ACS60 (300 MHz) instrument using TMS as internal standard. The chemical shifts are given in ppm and coupling constants in Hz in the indicated solvent. Some abbreviation for NMR: singlet (s), broad singlet (bs), doublet (d), triplet (t), quartet (q), quintet (quint), multiplet (m).
Chemicals All solvents and reagents were purchased from Aldrich, Fluka, Merck and Lancaster and used without further purification.

Dipyrrolmethane was prepared as described by C. Brücker et al., *J. Porphyrins Phthalocyanines,* 2 455 (1998).
Chromatography Column chromatography was carried out using silica gel (Merck Silicagel 60, Fluka 60, 0.040-0.063 mm) and Sephadex LH-20 (Pharmacia). All solvents (Synopharm) for chromatography were technical pure grade.
Abbreviations
DDQ: 2,3-dichloro-5,6-dicyano-p-benzoquinone
DMF: N,N-dimethylformamide
TFA: trifluoroacetic acid Synthesis Routes for Test Compounds The following test compounds were synthesised:

Exemplary Compounds for Use in the Invention
Compounds 6, 8 to 10, 12, 23, 25, 28, 31 and 32.
Reference Compounds (for Use as Comparative Controls)
Compounds 1, 3, 16, 19, 26, 29, 33, 36, 37, 39, 41 and 46 to 51.
Chemical Intermediates
Compounds 2, 4, 5, 7, 11, 13 to 15, 17, 18, 20 to 22, 24, 27, 30, 34, 35, 38, 40 and 42 to 45.

Compound 1

5,10,15,20-tetrakis-[4-(3-Trimethylammonio-propyloxy)-phenyl]-porphyrin tetrachloride

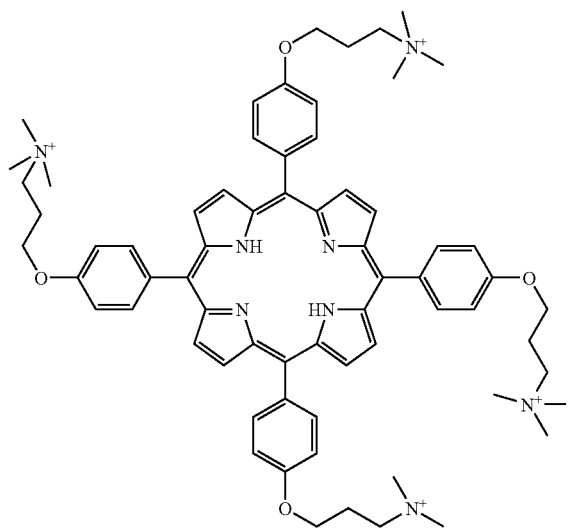

To a vigorously-stirred suspension of 5,10,15,20-tetrakis-(4-hydroxy-phenyl)-porphyrin (50 mg, 0.07 mmol) and $K_2CO_3$ (230 mg, 1.7 mmol) in DMF (20 mL), a solution of (1-bromopropyl)-trimethylammonium bromide (0.27 g, 1.05 mmol) in DMF (5 mL) is added dropwise at 50° C. during 30 mins. The mixture is stirred at 50° C. for 15 h. After removal of DMF under reduced pressure, the residue obtained is dissolved in methanol (5 mL) and filtered through a pad of silica gel (depth 2 cm) supported on a steel frit (diameter 3.5 cm). After washing with methanol (1 L), the pad is eluted with acetic acid. After evaporation of solvent from the eluate, the residue obtained is purified by chromatography on a column (2.5×40 cm) of Sephadex LH20 eluting with n-butanol:water:acetic acid (4:5:1, by vol., upper phase). The recovered material is dissolved in the minimum volume of methanol and the solution is passed through a short column (3.5×20 cm) of anion exchange resin (Amberlite IRA 400, chloride form). The recovered tetrachloride salt is dried under high vacuum and obtained as a violet solid.

$^1$H-NMR:

$\delta_H$ (300 MHz, $CD_3OD$): 2.35-2.50 (bs, 8H), 3.25-3.35 (bs, 36H), 3.65-3.75 (bs, 8H), 4.35 (m, 8H), 7.30, 8.10 (2×d, $^3J$ 8.5 Hz, 16H), 8.80-9.00 (bs, 8H).

Compound 2

5,10,15-tris-(4-Hydroxy-phenyl)-20-(4-undecyloxy-phenyl)-porphyrin

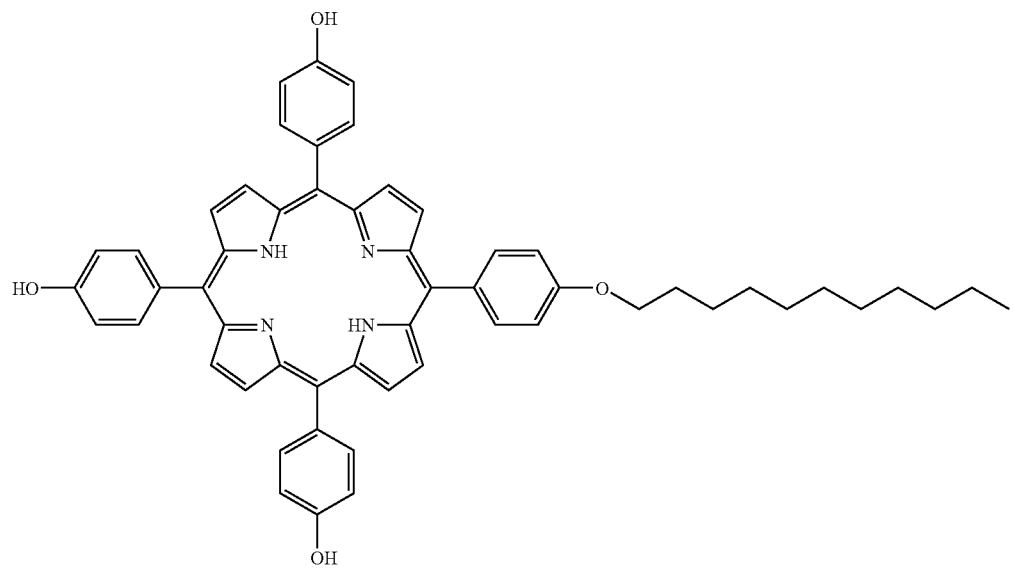

To a vigorously-stirred suspension of 5,10,15,20-tetrakis-(4-hydroxy-phenyl)-porphyrin (400 mg, 0.59 mmol) and K$_2$CO$_3$ (1.0 g, 7.1 mmol) in DMF (75 mL), a solution of 1-bromoundecane (0.1 mL, 0.45 mmol) in DMF (10 mL) is added dropwise at 50° C. during 30 mins and the mixture is stirred at the same temperature for 1.5 h. After removal by filtration of K$_2$CO$_3$ and removal under reduced pressure of DMF, the residue obtained is dissolved in dichloromethane (200 mL), washed with water (3×150 mL) and the solution dried (Na$_2$SO$_4$). The solvent is evaporated under reduced pressure and the residue obtained is dissolved in toluene:ethanol (5:1 by vol., ca. 10 mL) and purified by chromatography using a column (5×50 cm) of silica gel (Merck 60). The column is eluted with toluene followed by toluene:ethyl acetate (2:1 by vol.) and the desired material recovered by evaporation of solvent from the appropriate fractions is dried under high vacuum. The product is obtained as a violet solid.

$^1$H-NMR:

$\delta_H$ (300 Mz, d6-acetone): 0.95 (t, $^3$J 7.5 Hz, 3H), 1.25-1.55 (m, 14H), 1.58 (quint, $^3$J 7.5 Hz, 2H), 1.85 (quint, $^3$J 7.5 Hz, 2H), 4.16 (t, $^3$J 7.5 Hz, 2H), 7.20 (d, $^3$J 8.1 Hz, 2H), 7.25 (d, $^3$J 8.2 Hz, 6H), 8.00-8.15 (m, 8H), 8.80-9.10 (m, 8H).

Compound 3

5,10,15-tris-[4-(3-Trimethylammonio-propyloxy)-phenyl]-20-(4-undecyloxy-phenyl)-porphyrin trichloride To a vigorously-stirred suspension of Compound 2 (100 mg, 0.12 mmol) and K$_2$CO$_3$ (230 mg, 1.7 mmol) in DMF (30 mL), a solution of (1-bromopropyl)-trimethylammonium bromide (0.3 g, 16.6 mmol) in DMF (10 mL) is added at 50° C. and the mixture is stirred at this temperature for 12 h. After removal of the DMF under reduced pressure, the residue obtained is dissolved in methanol (5 mL) and filtered through a pad of silica gel (depth 2 cm) supported on a steel frit (diameter 3.5 cm). After washing with methanol (ca. 1 L), the pad is eluted with acetic acid:methanol:water (3:2:1, by vol.). After evaporation of the solvent from the eluate under reduced pressure, the residue obtained is purified by chromatography on a column (2.5×40 cm) of Sephadex LH-20 eluting with n-butanol:water:acetic acid (5:4:1, by vol., upper phase). After removal of the solvent from appropriate fractions of the eluate under reduced pressure, the residue obtained is dissolved in methanol (5 mL) and the solution is passed through a short column (3.5×20 cm) of anion exchange resin (Amberlite IRA 400, chloride form). The final product is obtained as the trichloride salt, after removal of solvent and drying under high vacuum, as a violet solid.

$^1$H-NMR $\delta_H$ (300 MHz, CD$_3$OD): 0.80 (t, $^3$J 7.5 Hz, 3H), 1.15-1.45 (m, 16H), 1.50-1.60 (bs, 2H), 2.25-2.45 (bs, 6H), 3.25-3.35 (bs, 27H), 3.75-3.85 (bs, 6H), 4.18 (t, $^3$J 7.5 Hz, 2H), 4.40-4.45 (bs, 6H), 7.20-7.40, 7.95-8.15 (2×m, 16H), 8.60-9.00 (bs, 8H).

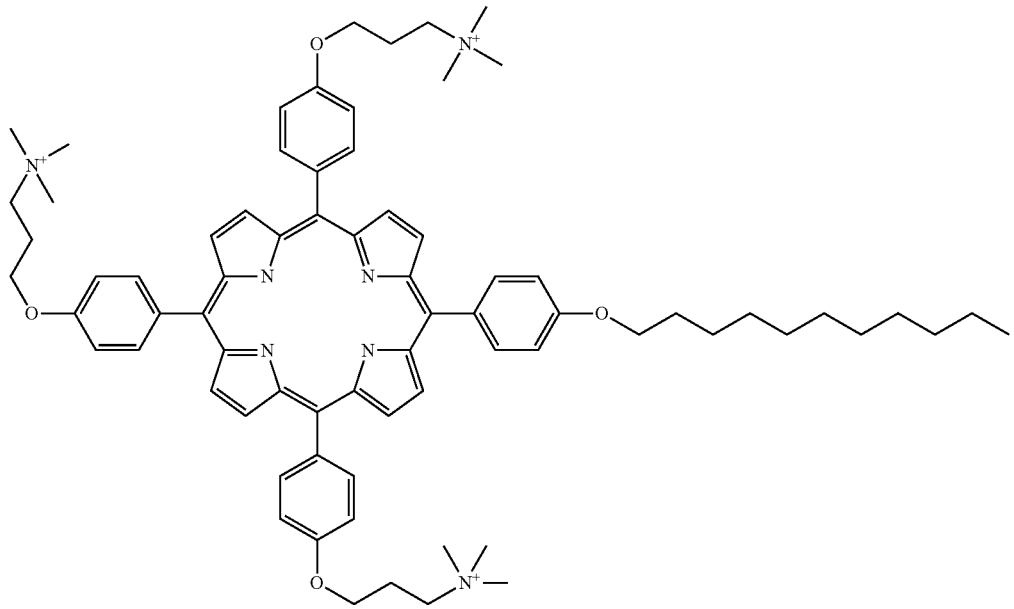

Compound 4

5-(3,5-Dimethoxy-phenyl)-15-undecyl-porphyrin

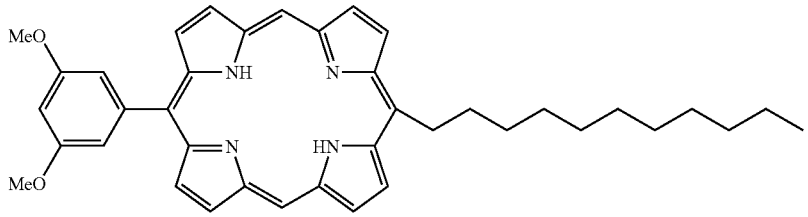

To a stirred solution of dipyrrolemethane (0.62 g, 4.2 mmol) in dichloromethane (5 mL) is added 3,5-dimethoxybenzaldehyde (0.35 g, 2.1 mmol) and dodecanal (0.464 g, 2.52 mmol) in degassed dichloromethane (1 L). TFA (0.07 mL, 3.0 mmol) is added dropwise. The solution is stirred at room temperature in the dark for 17 h under argon. After addition of DDQ (2.7 g, 12 mmol), the mixture is stirred at room temperature for a further hour. Purification of material recovered after removal of solvent under reduced pressure by chromatography on a column (400 g) of silica gel (Merck 60) with toluene for elution yields the product as a violet solid.

$^1$H-NMR:

$\delta_H$ (300 Mz, CDCl$_3$): 0.80 (t, $^3$J 7.5 Hz, 3H), 1.10-1.25 (m, 12H), 1.40 (m, 2H), 1.75 (quint, $^3$J 7.5 Hz, 2H), 2.45 (quint, $^3$J 7.5 Hz, 2H), 3.90 (s, 6H), 4.90 (t, $^3$J 7.5 Hz, 2H), 6.80 (m, 1H), 7.35 (m, 2H), 9.00, 9.25, 9.30, 9.50 (4×d, $^3$J 4.7 Hz, 4×2H), 10.15 (s, 2H).

Compound 5

5-(15-Undecyl-porphyrin-5-yl)-benzene-1,3-diol

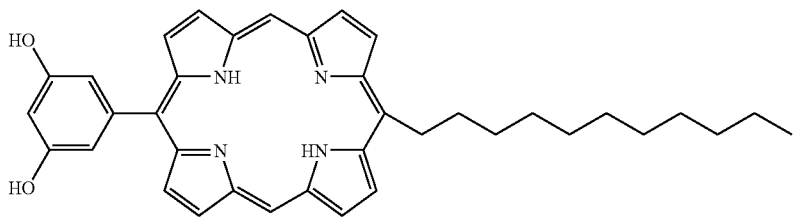

To a solution of Compound 4 (80 mg, 0.133 mmol) in anhydrous dichloromethane (80 mL) under an argon atmosphere, BBr$_3$ (5 mL, 1M in dichloromethane) is added dropwise at −70° C. and the mixture is stirred for 1 h at this temperature and then warmed to room temperature and stirred overnight. The mixture is cooled to −10° C. and hydrolysed by the addition of water (2 mL) and stirring for 1 h. NaHCO$_3$ (3 g) is added directly for neutralisation. The mixture is stirred for a further 12 h and after filtration of NaHCO$_3$ and removal of dichoromethane under vacuum the residue obtained is purified by column chromatography using silica gel eluting with dichloromethane. After evaporation of solvent from appropriate combined fractions and drying of the residue obtained under high vacuum the product is obtained as a violet solid $^1$H-NMR:

$\delta_H$ (300 Mz, d6-acetone): 0.75 (t, $^3$J 7.5 Hz, 3H), 1.05-1.25 (m, 12H), 1.30-1.40 (m, 2H), 1.45-1.50 (m, 2H), 2.40 (quint, $^3$J 7.5 Hz, 2H), 4.90 (t, $^3$J 7.5 Hz, 2H), 6.65 (m, 1H), 7.18 (m, 2H), 8.60-8.65, 9.00-9.05, 9.35-9.40, 9.55-9.60 (4×m, 8H), 10.25 (s, 2H).

Compound 6

5-[3,5-bis-(3-Trimethylammonio-propyloxy)-phenyl]-15-undecyl-porphyrin dichloride

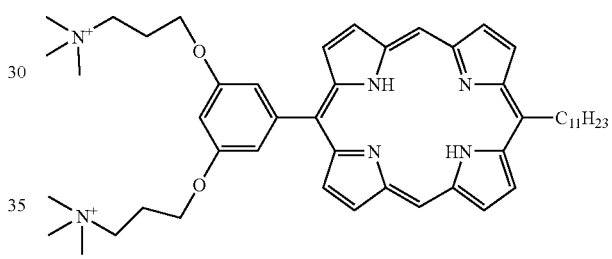

To a vigorously-stirred suspension of Compound 5 (80 mg, 0.14 mmol) and K$_2$CO$_3$ (230 mg, 1.7 mmol) in DMF (30 mL) is added (1-bromopropyl)-trimethylammonium bromide (0.3 g, 16.6 mmol) at 50° C. The mixture is stirred at this temperature for 18 h. After removal of the DMF under reduced pressure, the residue obtained is dissolved in methanol (5 mL) and filtered through a pad of silica gel (depth 2 cm) supported on a steel frit (diameter 3.5 cm). After washing the pad with methanol (ca. 1 L) the crude product is eluted with acetic acid:methanol:water (3:2:1, by vol.). Appropriate fractions are collected and, after evaporation of the solvent under reduced pressure, the residue obtained is purified by chromatography on a column (2.5×40 cm) of Sephadex LH-20 eluting with n-butanol:water:acetic acid (5:4:1, by vol., upper phase). After removal of the solvent from appropriate fractions under reduced pressure, the residue obtained is dissolved in methanol (5 mL) and the solution is passed through a short column (3.5×20 cm) of anion exchange resin (Amberlite IRA 400, chloride form). After collection of the eluate, solvent is removed under reduced pressure and the residue obtained is dried under high vacuum to yield the dichloride salt as a violet solid.

¹H-NMR:

$\delta_H$ (300 Mz, CD$_3$OD): 0.75 (t, $^3$J 7.5 Hz, 3H), 1.05-1.20 (m, 14H), 1.45-1.50 (m, 2H), 2.05-2.15 (m, 4H), 2.15-2.20 (m, 2H), 2.95 (s, 18H), 3.35-3.45 (m, 4H), 3.95 (t, $^3$J 7.5 Hz, 4H), 4.55 (t, $^3$J 7.5 Hz, 2H), 6.85 (m, 1H), 7.35 (m, 2H), 8.85-8.90, 9.15-9.20, (3×m, 8H), 10.10 (s, 2H).

Compound 7

5,15-bis-[4-(3-Bromo-propyloxy)-phenyl]-porphyrin

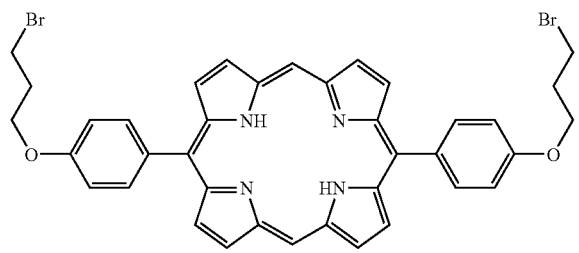

To a stirred solution of dipyrrolemethane (0.61 g, 4.1 mmol) and 4-(3-bromopropyloxy)-benzaldehyde (1.03 g, 4.2 mmol) in degassed dichloromethane (1 L), TFA (0.07 mL, 1.5 mmol) is added dropwise. The solution is stirred at room temperature in the dark under argon for 17 h. After addition of DDQ (2.76 g, 0.012 mol), the mixture is stirred at room temperature for a further hour. Filtration through silica gel (Fluka 60, 100 g) using dichloromethane for elution gives raw product which, after treatment with dichloromethane:n-hexane, yields pure product as a violet solid.

¹H-NMR:

$\delta_H$ (300 Mz, C$_6$D$_6$): −3.15 (2H, s), 2.00 (quint, $^3$J 7.5 Hz, 4H), 3.30 (t, $^3$J 7.5 Hz, 4H), 3.90 (t, $^3$J 7.5 Hz, 4H), 7.15-7.18, 7.95-8.15 (2×m, 2×4H), 9.15-9.20,(m, 8H), 10.05 (s, 2H).

Compound 8

5,15-bis-(4-{3-[(3-Dimethylamino-propyl)-dimethylammonio]-propyloxy}-phenyl)-porphyrin dichloride

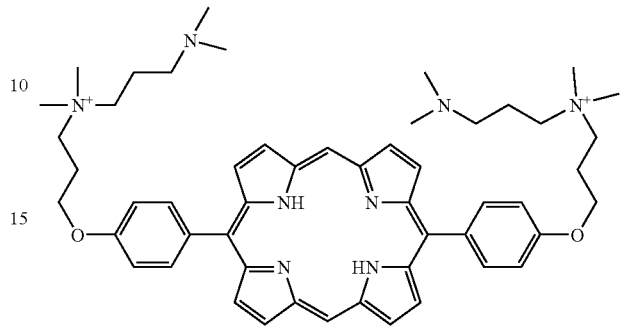

Compound 7 (200 mg, 0.27 mmol) is dissolved in absolute DMF (40 mL) with N,N,N',N'-tetramethyl-1,3-propanediamine (5 mL, 13.9 mmol) and the solution is stirred at 50° C. under argon overnight. After evaporation of the solvent under reduced pressure, the residue obtained is dissolved in methanol (5 mL) and the solution is filtered through a pad of silica gel (depth 2 cm) supported on a steel frit (diameter 3.5 cm). The pad is eluted with methanol (ca. 1 L) followed by acetic acid:methanol:water (3:2:1, by vol.). After evaporation of the solvent from appropriate fractions, the raw product obtained is dissolved in methanol (5 mL) and further purified by chromatography on a column (2.5×40 cm) of Sephadex LH-20 using n-butanol:water:acetic acid (4:5:1, by vol., upper phase) as the developing phase. The first fraction eluted is the desired product. After removal of solvent under reduced pressure the residue obtained is dissolved in methanol (5 mL) and passed through a short column (3.5×20 cm) of anion exchange resin (Amberlite IRA 400, chloride form). After removal of solvent under reduced pressure from the eluate, the residue is treated with diethylether and dried under high vacuum to give the product as a violet solid.

¹H-NMR:

$\delta_H$ (300 MHz, CD$_3$OD): 2.20-2.35 (m, 4H), 2.40-2.50 (m, 4H), 2.80 (s, 12H), 3.05 (4H, t, $^3$J 7.8, 2H), 3.25 (s, 12H), 3.45-3.55 (bs, 4H), 3.65-3.75 (m, 4H), 4.30 (t, $^3$J 4.2 Hz, 4H), 7.40, 8.10 (2×d, $^3$J 7.5 Hz, 2×4H), 8.95, 9.45 (2×d, $^3$J 4.2 Hz, 8H), 10.40 (s, 2H).

Compound 9

5,15-bis-[4-(3-Triethylammonio-propyloxy)-phenyl]-porphyrin dichloride

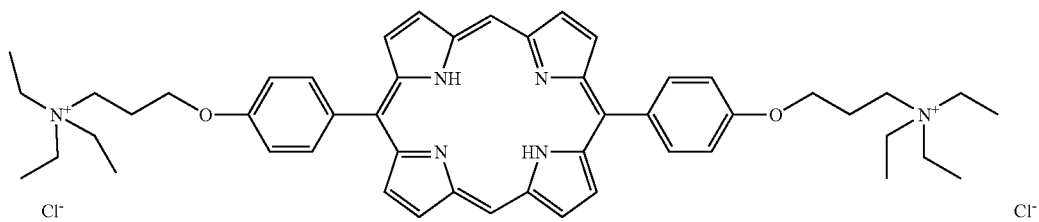

To a solution of Compound 7 (50 mg, 0.068 mmol) in absolute DMF (20 mL) is added triethylamine (4.7 mL, 0.034 mol, 500 eq.). The mixture is stirred at 60° C. for 24 h. The solvent is removed under reduced pressure and the residue obtained is dissolved in methanol (5 mL) and filtered through a pad of silica gel (depth 2 cm) supported on a steel frit (diameter 3.5 cm). After washing with methanol (ca. 1 L) the pad is eluted with acetic acid:methanol:water (3:2:1, by vol.). After evaporation of the solvent from the eluted fraction, the raw product obtained is dissolved in methanol (5 mL) and purified by chromatography on a column (2.5×40 cm) of Sephadex LH-20 eluting with n-butanol:water:acetic acid (4:5:1, by vol., upper phase). The solvents are removed under reduced pressure from appropriate fractions, the residue obtained is dissolved in methanol (5 mL) and the solution is passed through a short column (3.5×20 cm) of anion exchange resin (Amberlite IRA 400, chloride form) to yield the product as a violet solid after evaporation of solvent.

$^1$H-NMR:

$\delta_H$ (300 Mz, CD$_3$OD): 1.25 (m, 18H), 2.13 (m, 4H), the signals for—CH$_2$NCH$_2$ (16H) are in the area 3.00-3.40 as a part of the multiplet covered by the solvent signals, 4.15 (t, 4H, $^3$J=7.5 Hz), 7.36 (d, 4H, $^3$J=7.5 Hz ), 8.15 (d, 4H, $^3$J=7.5 Hz), 9.05 (d, 4H, $^3$J=7.5 Hz), 9.54 (d, 4H, $^3$J=7.5 Hz), 10.45 (s, 2H)

Compound 10

5,15-bis-[4-(3-Trimethylammonio-propyloxy)-phenyl]-porphyrin dichloride

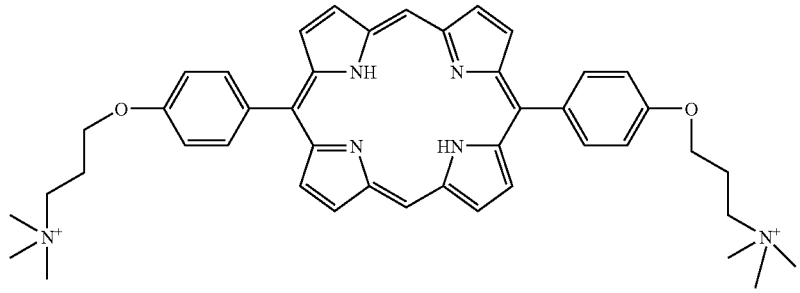

A solution of Compound 7 (300 mg, 0.41 mmol) in absolute DMF (50 mL) is transferred into a 100 mL autoclave. After addition of trimethylamine (4.5 g ), the mixture is stirred at 50° C. for 16 h. After evaporation of the solvent, the residue obtained is dissolved in methanol (5 mL) and the solution is filtered through a pad of silica gel (depth 2 cm) supported on a steel frit (diameter 3.5 cm). After washing with methanol (ca. 1 L) the pad is eluted with acetic acid:methanol:water (3:2:1, by vol.). After evaporation of the solvent from appropriate fractions, the residue obtained is dissolved in methanol (5 mL) and purified by chromatography on a column (2.5×40 cm) of Sephadex LH-20, eluting with n-butanol:water:acetic acid (4:5:1, by vol., upper phase). Two fractions are obtained, the first-eluting of which is the desired product. The solvent is removed under reduced pressure and the residue obtained is redissolved in methanol (5 mL) and the solution is passed through a short column (3.5×20 cm) of anion exchange resin (Amberlite IRA 400, chloride form). After evaporation of the solvent under reduced pressure, the residue is treated with methanol:diethylether and dried under high vacuum to give the product as a violet solid.

$^1$H-NMR:

$\delta_H$ (300 Mz, CD$_3$OD): 2.40-2.60 (m, 4H), 3.30-3.25 (bs, 18H), 3.75-3.80 (m, 4H), 4.40(t, $^3$J 7.5 Hz, 4H), 7.40, 8.20 (2×d, $^3$J 8.5 Hz, 8H), 9.05, 9.50 (2×d, $^3$J 4.5 Hz, 8H), 10.45 (s, 2H).

Alternative Synthesis Route for Compound 10

Compound 42 (100 mg, 0.2 mMol; see below) is dissolved and potassium carbonate (230 mg 1.7 mMol) is suspended in DMF (30 mL) and to the vigorously-stirred mixture is added a solution of (1-bromopropyl)-trimethylammonium bromide (350 mg, 1.3 mMol) in DMF (5 mL) dropwise at 50° C. during 30 mins. The mixture is heated for 15 h. DMF is removed by rotary evaporation and the residue obtained is dissolved in methanol and the solution is filtered through a pad of silica gel (depth 2 cm) supported on a steel frit (diameter 3.5 cm). After washing with methanol (ca. 1 L) the pad is eluted with acetic acid:methanol:water (3:2:1, by vol.). After evaporation of the solvent from appropriate fractions, the residue obtained is dissolved in methanol (5 mL) and purified by chromatography on a column (2.5×40 cm) of Sephadex LH-20, eluting with n-butanol:water:acetic acid (4:5:1, by vol., upper phase). Two fractions are obtained, the first-eluting of which is the desired product. The solvent is removed under reduced pressure and the residue obtained is redissolved in methanol (5 mL) and the solution is passed through a short column (3.5×20 cm) of anion exchange resin (Amberlite IRA 400, chloride form). After evaporation of the solvent under reduced pressure, the residue is treated with methanol:diethylether and dried under high vacuum to give the product as a violet solid.

Compound 11

5,15-bis-[3-(3-Bromo-propyloxy)-phenyl]-porphyrin

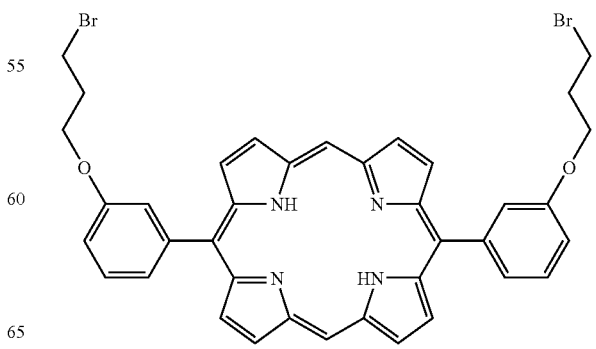

To a stirred solution of dipyrrolemethane (1.22 g, 8.2 mmol) and 3-(3-bromo-propyloxy)-benzaldehyde (2.06 g, 8.2 mmol) in degassed dichloromethane (2 L), TFA (0.14 mL, 3 mmol) is added dropwise. The solution is stirred at room temperature in the dark for 17 h under argon. After addition of DDQ (5.4 g, 0.024 mol), the mixture is stirred at room temperature for a further 1 h. After removal of solvents under reduced pressure, the residue obtained is dissolved in dichloromethane (5 mL) and passed through a column (300 g) of silica (Fluka 60) using dichloromethane as eluent to give raw product which is treated with dichloromethane:methanol to yield pure material as a violet solid.

¹H-NMR:

$\delta_H$ (300 Mz, CDCl$_3$): −3.20 (2H, s), 2.40 (quint, $^3$J 7.5 Hz, 4H), 3.65 (t, $^3$J 7.5 Hz, 4H), 4.25 (t, $^3$J 7.5 Hz, 4H), 7.20-7.25, 7.60-7.65, 7.75-7.80 (3×m, 8H), 9.05, 9.25, (2×d, $^3$J 4.2 Hz, 8H), 10.25 (s, 2H).

Compound 12

5,15-bis-[3-(3-Trimethylammonio-propyloxy)-phenyl]-porphyrin dichloride

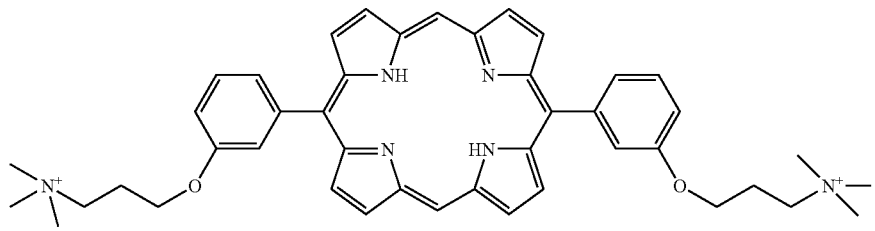

A solution of Compound 11 (400 mg, 0.543 mmol) in DMF (50 mL) is transferred into a 100 mL autoclave. After addition of trimethylamine (6.3 g), the mixture is stirred at 50° C. for 8 h. After evaporation of the solvent under reduced pressure, the residue obtained is dissolved in methanol (5 mL) and the solution is filtered through a pad of silica gel (depth 2 cm) supported on a steel frit (diameter 3.5 cm). After washing the pad with methanol (ca. 1 L), elution with acetic acid:methanol:water (3:2:1, by vol.) affords fractions which, after evaporation of the solvent under reduced pressure, gives a solid residue. This is dissolved in methanol (5 mL) and purified by chromatography on a column (2.5×40 cm) of Sephadex LH-20 eluting with n-butanol:water:acetic acid (4:5:1, by vol., upper phase). Two fractions are eluted from the column, the first of which is the desired product. After removal of the solvent under reduced pressure, the residue obtained is dissolved in methanol (5 mL). The solution is passed through a short column (3.5×20 cm) of anion exchange resin (Amberlite IRA 400, chloride form), the solvent is removed under reduced pressure and the raw product is treated with methanol:diethylether to give a violet solid which is dried under high vacuum.

¹H-NMR:

$\delta_H$ (300 Mz, CD$_3$OD): 2.30-2.35 (m, 4H), 3.15 (s, 18H), 3.95-4.05 (m, 4H), 4.20-4.25 (m, 4H), 7.40-7.45, 7.65-7.70, 7.80-7.85 (3×m, 8H), 9.00-9.05, 9.40-9.45,(2×m, 8H), 10.40 (m, 2H).

Compound 13

5,15-bis-(4-Hydroxy-phenyl)-10,20-bis-(4-undecyloxy-phenyl)-porphyrin

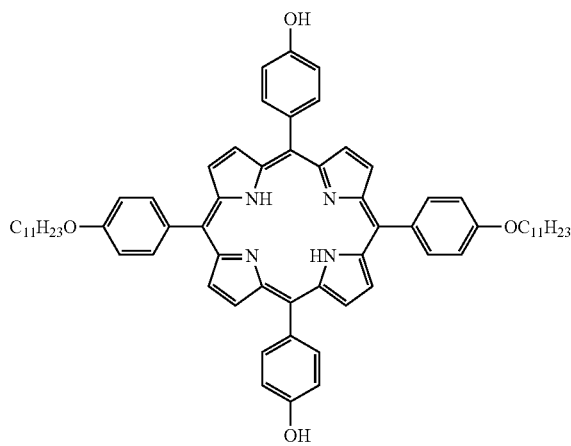

The third fraction eluted from the column during the chromatographic separation described for the synthesis of Compound 2 is characterised as 5,15-bis-(4-hydroxy-phenyl)-10,20-bis-(4-undecyloxy-phenyl)-porphyrin

¹H-NMR:

$\delta_H$ (300 Mz, CDCl$_3$): −2.88 (2H, s), 0.85 (t, $^3$J 7.5Hz, 6H), 1.20-1.40 (m, 28H), 1.55 (br m, 4H), 1.80 (quint, $^3$J 7.5Hz, 4H), 4.15 (t, $^3$J 7.5 Hz, 4H), 6.65, 7.15 (d, $^3$J 8.1Hz, 8H), 7.80, 8.00 (d, $^3$J 8.1Hz, 8H), 8.75-8.80 (m, 8H).

trans-Regioisomer geometry is assigned by ¹H-³C-2D-NMR in d-acetic acid.

Compound 14

5,10-bis-(4-Hydroxy-phenyl)-15,20-bis-(4-undecyloxy-phenyl)-porphyrin

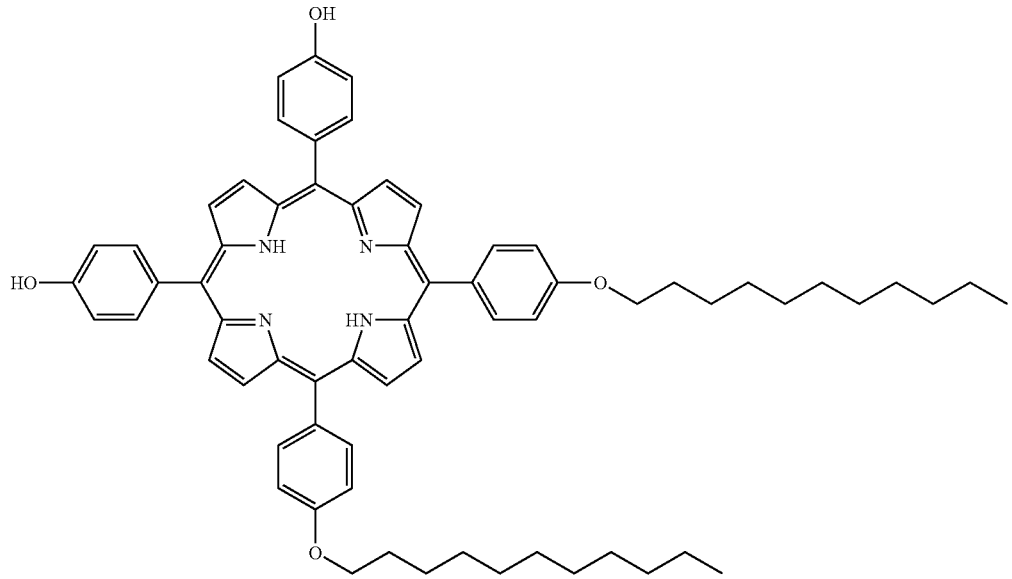

The fourth fraction eluted from the column during the chromatographic separation described for the synthesis of Compound 2 is characterised as 5,10-bis-(4-hydroxyphenyl)-15,20-bis-(4-undecyloxy-phenyl)-porphyrin.

$^1$H-NMR:

$\delta_H$ (300 MHz, CDCl$_3$): −2.80 (2H, s), 0.90 (t, $^3$J 7.5Hz, 6H), 1.20-1.60 (m, 28H), 1.65 (quint, $^3$J 7.5 Hz, 4H), 2.00 (quint, $^3$J 7.5 Hz, 4H), 4.22 (t, $^3$J 7.5 Hz, 4H), 7.15 (d, $^3$J 8.1 Hz, 4H), 7.25 (d, $^3$J 8.2 Hz, 4H), 8.10 (d, $^3$J 8.2 Hz, 4H ), 8.15 (d, $^3$J 8.2 Hz, 4H), 8.80-8.90 (m, 8H).

cis-Regioisomer geometry is assigned by $^1$H-$^{13}$C-2D-NMR in d-acetic acid.

Compound 15

5,10,15-tris-[4-(3-Bromo-propyloxy)-phenyl]-20-(4-undecyloxy-phenyl)-porphyrin

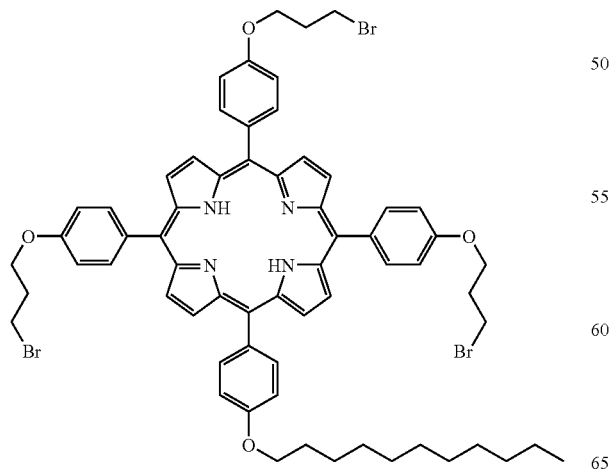

Under an argon atmosphere, Compound 2 (200 mg, 0.24 mmol) is dissolved in absolute DMF (40 mL) in the presence of K$_2$CO$_3$ (500 mg) and 1,3-dibromopropane (1.02 mL, 10 mmol). The mixture is heated overnight at 80° C. Work-up is as the procedure given for Compound 2 described above. The product is purified by column chromatography on silica gel (Merck 60) eluting with hexane:ethyl acetate (5:1, by vol.).

$^1$H-NMR:

$\delta_H$ (300 Mz, CDCl$_3$): −2.75 (2H, s), 0.85 (t, $^3$J 7.5 Hz, 3H), 1.20-1.45 (m, 14H), 1.50 (quint, $^3$J 7.5 Hz, 2H), 1.90 (quint, $^3$J 7.5 Hz, 2H), 2.40 (quint, $^3$J 7.4 Hz, 6H), 3.65 (t, $^3$J 7.4 Hz, 6H), 4.16 (t, $^3$J 7.5 Hz, 2H), 4.25 (t, $^3$J 7.5 Hz, 6H), 7.18-7.20 (m, 8H), 8.00-8.05 (m, 8H), 8.75-8.8 (m, 8H).

Compound 16

5,10,15-tris-[4-(3-Triethylammonio-propyloxy)-phenyl]-20-(4-undecyloxy-phenyl)-porphyrin trichloride

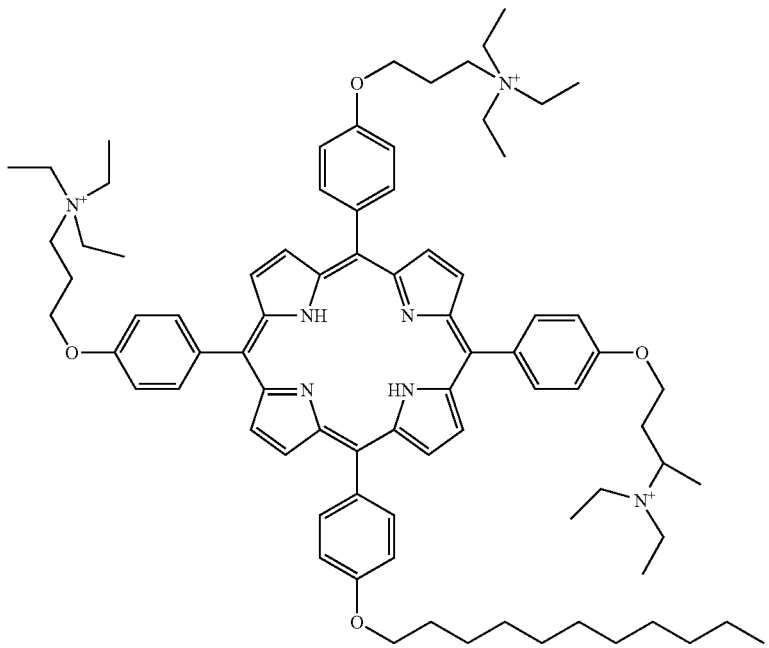

Compound 15 (200 mg, 0.17 mmol) is dissolved in absolute DMF (40 mL) with triethylamine (5 mL, 34.5 mmol, 208 eq.). The mixture is heated to 50° C. for 48 h. After removal of DMF under vacuum, the residue obtained is dissolved in methanol and purified by column chromatography using silica gel (Merck, 60) eluting with methanol:water:acetic acid (2:1:3, by vol.) and then acetic acid:pyridine (1:1, by vol.). Removal of solvent from appropriate fractions under vacuum affords raw product which is dissolved in methanol:aqueous NaCl (1M) (5 mL. 1:1, by vol.). The mixture is stirred for 30 mins and filtered through a pad of silica gel (depth 2 cm) supported on a steel frit (diameter 3.5 cm). After washing the pad with methanol (200 mL) it is eluted with methanol:water:acetic acid (2:1:3, by vol.). After evaporation of solvent from appropriate combined fractions, the residue obtained is dissolved in methanol (2 mL) and dichloromethane (5 mL) is added dropwise. The precipitated white gel is collected by filtration and the solvent is removed under high vacuum.

¹H-NMR:

$\delta_H$ (300 MHz, CD$_3$OD): 0.90 (t, $^3$J 7.5 Hz, 3H), 1.20-1.45 (m, 43H), 1.45-1.65 (bs, 2H), 2.25-2.40 (bs, 6H), 3.35-3.45 (bs. 24H), 3.50-3.60 (bs, 6H), 4.25 (t, $^3$J 7.5 Hz, 2H), 4.40-4.45 (bs, 6H), 7.25-7.40, 8.10-8.20 (m, 16H), 8.80-9.10 (bs, 8H).

Compound 17

5-[4-(3-Hydroxy-phenyl)]-15-(3-undecyloxy-phenyl)-porphyrin

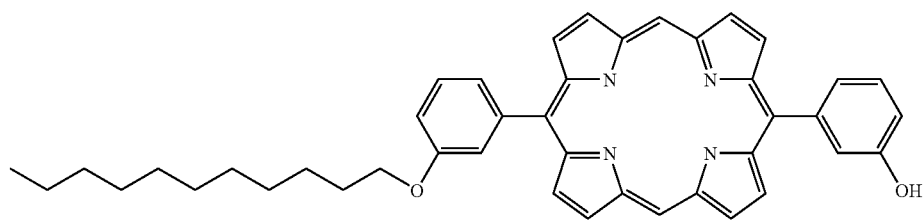

5-15-bis-(3-Hydroxy-phenyl)-porphyrin (Wiehe, A., Simonenko, E. J., Senge, M. O. and Roeder, B. *Journal of Porphyrins and Phthalocyanines* 5, 758-761 (2001)) (86 mg, 0.17 mmol) is dissolved and $K_2CO_3$ (250 mg, 7.1 mmol) is suspended in DMP (40 mL). To the vigorously-stirred mixture a solution of 1-bromoundecane (0.04 mL, 0.17 mmol) in DMF (5 mL) is added dropwise at 50° C. during 30 mins and the mixture is heated at that temperature for 1 h. After removal by filtration of $K_2CO_3$, DMF is removed under high vacuum. The residue obtained is purified by column chromatography using silica gel (Merck 60) eluting with n-hexane:ethyl acetate (10:1, by vol.). The 2nd fraction is collected and dried under high vacuum to give the product.

¹H-NMR:
$\delta_H$ (300 Mz. CDCl₃): -3.15 (2H, s), 0.75 (t, ³J 7.5 Hz. 3H), 1.10-1.30 (m, 14H), 1.35 (m, 2H), 1.80 (quint, ³J 7.5 Hz, 2H), 4.05 (t, ³J 7.5 Hz, 2H), 6.85-6.90, 7.20-7.25, 7.35-7.45, 7.50-7.65, 7.75-7.80 (5×m, 8H), 8.85, 8.95, 9.10, 9.20 (4×d, ³J 4.9 Hz, 4×2H), 10.15 (s, 2H).

Compound 18

5,10,15-tris-(3-Hydroxy-phenyl)-20-(3-dodecyloxy-phenyl)-porphyrin

3-Hydroxybenzaldehyde (1.8 g, 14.8 mmol, 3 eqv.) and 3-dodecyloxybenzaldehyde (1.35 g, 4.9 mmol, 1 eqv.) are dissolved in a mixture of acetic acid (145 mL) and nitrobenzene (98 mL, 960 mmol) and heated to 120° C. Pyrrole (1.35 mL, 19.6 mmol, 4 eqv.) is added in one portion and the mixture is stirred at 120° C. for 1 h. After cooling to room temperature, solvents are removed in, vacuo at 50° C. The product is isolated by chromatography on a column (500 g) of silica using toluene as eluent. The desired product is obtained as the fifth fraction from the column and is re-chromatographed using a smaller (200 g) silica column eluted with toluene. The product is obtained as a violet solid after evaporation of the solvent.

¹H-NMR:
$\delta_H$ (300 MHz, CDCl₃): 0.64 (t, 3H, ³J 6.8 Hz), 0.94-1.15 (m, 16H), 1.25 (bs, 2H), 1.62 (bs, 2H), 3.90 (bs, 2H), 6.33-6.95 (m, 8H), 7.08-7.60 (m, 8H), 8.20-8.47 (m, 4H), 8.51-8.70 (m, 4H)

Compound 19

5-{3-[bis-(2-Diethylamino-ethyl)-aminopropyloxy]-phenyl}-15-(3-undecyloxy-phenyl)-porphyrin

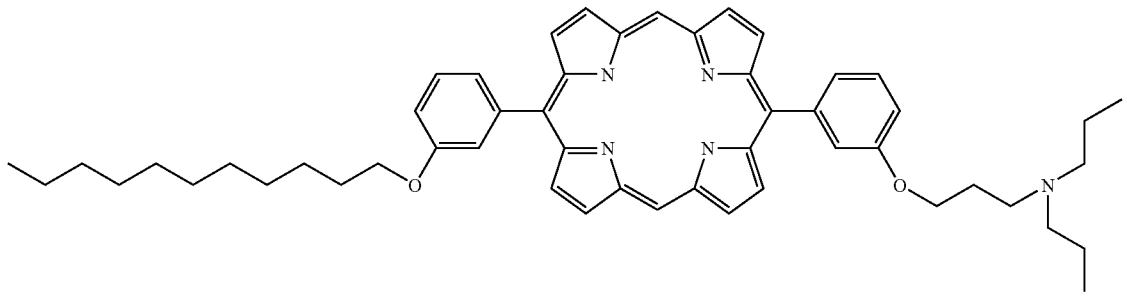

Compound 17 (50 mg, 0.065 mmol) is dissolved with N,N,N',N'-tetraethyldiethylenetriamine (1 mL, 39 mmol) in THF(10 mL) and the mixture is stirred at room temperature for 4 days. After evaporation of the solvent, the residue is dissolved in diethyl ether (20 mL) and the solution is washed with water (5×30 mL). The organic phase is dried (Na₂SO₄) and concentrated under high vacuum. The mixture is purified by column chromatography (silica gel, Merck 60) eluting with n-hexane:ethyl acetate (5:1, by vol.) followed by n-hexane:ethyl acetate:triethyl amine (10:10:1, by vol.). After collection of appropriate fractions and removal of solvent under reduced pressure, pure product is obtained by treatment of the residue with diethyl ether:methanol.

¹H-NMR:
$\delta_H$ (300Mz, CDCl₃): 0.80 (t, ³J 7.5 Hz, 3H), 0.9 (t, ³J 7.5 Hz, 12H), 1.20-1.40 (m, 14H), 1.45 (quint, ³J 7.5 Hz, 2H), 1.80 (quint, ³J 7.5 Hz, 2H), 1.95 (quint, ³J 7.5 Hz, 2H), 2.40-2.60 (m, 16H), 2.65 (t, ³J 7.5 Hz, 2H), 4.10 (t, ³J 7.5 Hz, 2H), 4.20 (t, 3J 7.5 Hz, 2H), 7.30-7.40, 7.55-7.65, 7.75-7.80 (3×m, 8H), 9.10-9.15, 9.20-9.25 (2×m, 2×4H), 10.15 (s, 2H).

Compound 20

5-[4-(3-Bromo-propyloxy)-phenyl]-15-(4-dodecyloxy-phen3l)-porphyrin

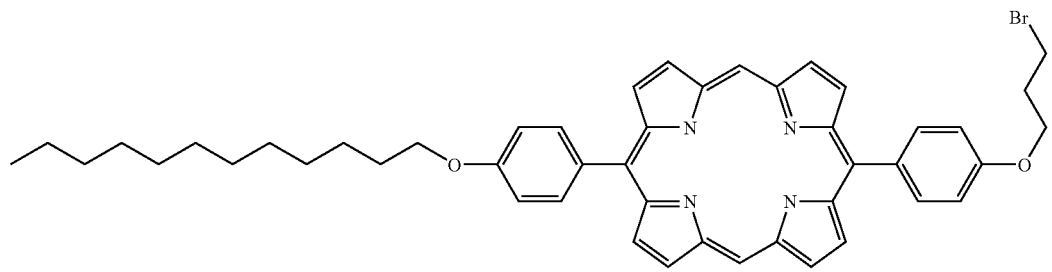

To a stirred solution of dipyrrolemethane (0.31 g, 2.1 mmol), 4-(3-bromo-proyloxy)-benzaldehyde (0.27 g, 1.1 mmol) and 4-dodecyloxy-benzaldehyde (0.32 g, 1.1 mmol) in degassed dichloromethane (500 mL). TFA (0.035 mL, 1.5 mmol) is added dropwise. The solution is stirred at room temperature in the dark for 17 h under argon. After addition of DDQ (1.38 g, 6 mmol), the mixture is stirred at room temperature for a further hour. Purification by column chromatography using silica gel (Merck 60, 400 g) with toluene as eluent affords the product ($2^{nd}$ fraction) together with Compound 7 ($3^{rd}$ fraction).

$^1$H-NMR:

$\delta_H$ (300 Mz, CDCl$_3$): −3.15 (2H, s), 0.90 (t, $^3$J 7.5 Hz, 3H), 1.20-1.40 (m, 16H), 1.55 (quint, $^3$J 7.5 Hz, 2H), 1.90 (quint, 3J 7.5 Hz, 2H), 2.40 (quint, $^1$J 7.5 Hz, 2H), 3.75 (t, $^1$J 7.5 Hz, 2H), 4.20 (t, $^1$J 7.5 Hz, 2H), 4.35 (t, $^3$J 7.5 Hz, 2H), 7.20-7.30, 8.10-8.15 (2×m, 8H), 9.10-9.15, 9.25-9.30 (2×m, 2×4H), 10.20 (s, 2H).

Compound 21

5,10,15,20-tetrakis-(3-Hydroxy-phenyl)-porphyrin

3-Hydroxybenzaldehyde (0.910 g, 7.45 mmol) is dissolved in propionic acid (50 mL) and heated to 140° C. Pyrrole (0.52 mL, 7.45 mmol) is added in one portion and the mixture heated at reflux for 2 h. Stirring is continued for an additional 12 h at room temperature. Propionic acid is removed in vacuo and the residue dissolved in acetone and purified by chromatography on a column (250 g) of silica which is eluted with toluene containing a continuously increasing proportion of ethyl acetate. The product is eluted with toluene:ethyl acetate (6:1 by vol.). Solvent is removed in vacuo to afford the product as a violet solid.

$^1$H-NMR:

$\delta_H$ (300 MHz, d6-acetone): 7.18 (d, 4H, $^3$J=8.25 Hz), 7.49 (t, 4H, $^3$J=8.25 Hz), 7.56-7.62 (m, 8H), 8.81 (m, 8H)

Compound 22

5,10,15-tris-[4-(3-Bromo-propyloxy)-phenyl]-20-(4-dodecyloxy-phenyl)-porphyrin

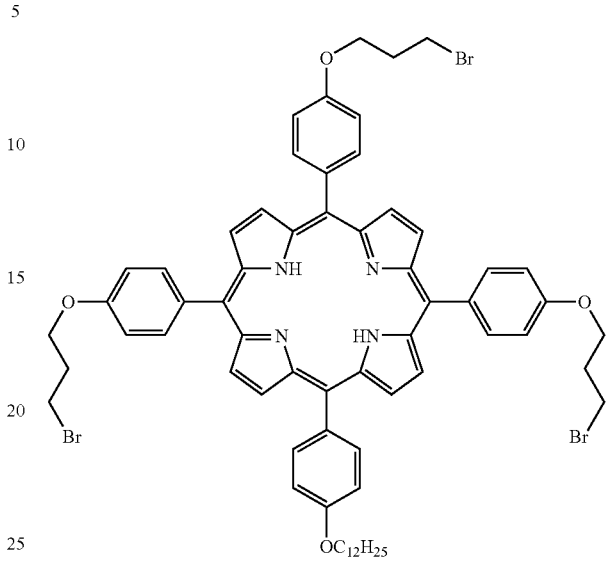

To a stirred solution of pyrrole (0.7 ml, 10 mmol), 4-(3-bromoproyloxy)-benzaldehyde (1.8 g, 7.5 mmol) and 4-(n-dodecyloxy)-benzaldehyde (0.725 g, 2.5 mmol) in degassed dichloromethane (1 L) is added TFA (0.085 ml, 10 mmol) dropwise. The reaction solution is stirred under argon at room temperature in the dark for 17 h. After addition of DDQ (6.9 g, 30 mmol), the reaction mixture is stirred at room temperature for a further 1 h. The solvents are removed under reduced pressure and the residue re-dissolved in toluene. Chromatographic purification on a column (3.5×30 cm) of silica gel (Merck 60) using toluene:n-hexane (1:4 by vol.) as eluent gives crude product which is purified by treatment with methanol:dichloromethane, giving a violet solid.

$^1$H-NMR:

$\delta_H$ (300 MHz, CDCl$_3$): 0.90 (t, $^3$J 7.5 Hz, 3H), 1.20-1.45 (m, 16H), 1.60 (quint, $^3$J 7.5 Hz, 2H), 1.90 (quint, $^3$J 7.5 Hz, 2H), 2.50 (quint, $^3$J 7.4 Hz, 6H), 3.75 (t, $^3$J 7.4 Hz, 6H), 4.20 (t, $^3$J 7.5 Hz, 2H), 4.35 (t, $^3$J 7.5 Hz, 6H), 7.25-7.30 (m, 8H), 8.15-8.30 (m, 8H), 8.80-8.85 (m, 8H).

Compound 23

5-{4-[3-Dimethyl-(3-dimethylaminopropyl)-ammonio-propyloxy]phenyl}-15-(4-dodecyloxy-phenyl)-porphyrin chloride

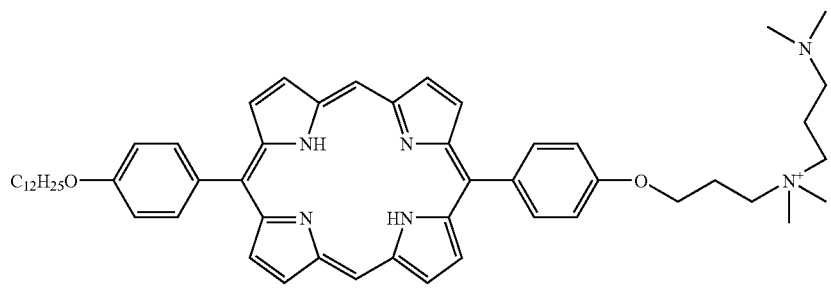

Compound 20 (30 mg, 0.038 mmol) is dissolved with N,N,N',N'-tetramethyl-1,3-propanediamine (156 mg, 1.2 mmol) in THF:DMF(1:1 by vol., 20 mL) and stirred at 50° C. for 18 h. After evaporation of the solvent under reduced pressure, the residue is dissolved in dichloromethane and purified by column chromatography (silica gel Merck 60) eluting with acetic acid:methanol:water (3:2:1, by vol.). After combining appropriate fractions and removal of solvent under reduced pressure, the residue is treatment with dichloromethane:hexane to afford the product as a violet solid.

$^1$H-NMR:

$\delta_H$ (300 Mz, CDCl$_3$+1% acetic acid ): 0.85 (m, 3H), 1.20-1.40 (m, 18H), 1.55-1.60 (m, 2H), 1.60-1.65 (m, 4H), 2.10-2.20 (bs, 8H), 3.15-3.25 (m, 8H), 3.75 (bs, 2H), 4.20 (bs 2H), 4.35 (bs, 2H), 7.15-7.20, 8.10-8.15 (2×m, 8H), 8.95-9.00, 9.10-9.15, 9.25-9.30 (3×bs, 8H), 10.20 (s, 2H).

Compound 24

5,15-bis-(3-Methoxy-phenyl)-10-undecyl-porphyrin

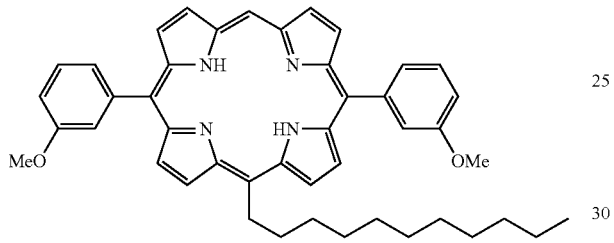

Into a 50 mL flask containing lithium (500 mg, 71 mmol) is added freshly distilled diethyl ether (15 mL) under an argon atmosphere. The suspension is refluxed for 1 hour, cooled to 15° C. and treated with a solution of n-undecylbromide (6.58 g, 71 mmol) in ether (6 mL) added dropwise via syringe. The mixture is cooled to 7-10° C. and, after 5 min, when the suspension becomes slightly cloudy and bright spots appear on the lithium metal, the remainder of the n-undecylbromide solution is added at an even rate over a period of 30 min while the internal temperature is maintained at below 10° C. Upon completion of addition, the mixture is stirred further for 1 h at 10° C. The suspension is filtered under argon to remove excess lithium and lithium bromide.

5,15-bis-(3-Methoxy-phenyl)-porphyrin (100 mg, 0.19 mmol) is dissolved in anhydrous TBF (30 mL) at −50° C. under an argon atmosphere. The organolithium reagent described above (5 mL) is added dropwise to the mixture. After 5 min the cooling bath is removed and the mixture is warmed to room temperature. After stirring at room temperature for 15 min the reaction is quenched b) slow addition of water (2 mL). After 15 min the mixture is oxidized by the addition of DDQ (4 mL. 0.4 mmol, 0.1 M in THF) and stirred for a further 15 min. The mixture is filtered through alumina (neutral, Brockman grade +) and purified by column chromatography on silica gel eluting with hexane:dichloromethane (4:1 by vol.). The first fraction is collected and treated with methanol:dichloromethane to give a solid product.

$^1$H-NMR:

$\delta_H$ (300 Mz, CDCl$_3$): −3.05 (bs, 2H, s), 0.80 (t, $^3$J 7.5 Hz, 3H), 1.10-1.20 (m, 12H), 1.25 (m, 2H), 1.70 (quint, $^3$J 7.5 Hz, 2H), 2.40 (quint, $^3$J 7.5 Hz, 2H), 3.85 (s, 6H), 4.95 (t, $^3$J 7.5 Hz, 2H), 7.20-7.23, 7.50-7.60, 7.65-7.75 (3×m, 8H), 8.85-8.90, 9.10-9.15, 9.35-9.40 (3×m, 8H), 9.95 (s, 1H).

Compound 25

3-[({3-[(3-{4-[15-(4-Dodecyloxy-phenyl)-porphyrin-5-yl]-phenoxy}-propyl)-dimethyl-ammonio]-propyl}-dimethyl-ammonio)-propyl]-trimethyl-ammonium trichloride

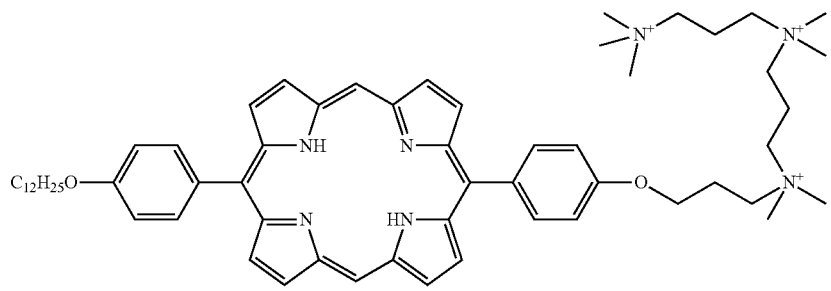

Compound 23 (20 mg, 0.022 mmol) and (1-bromopropyl)-trimethyl-ammonium bromide (26 mg, 0.1 mmol) are dissolved in DMP(15 ml) and stirred overnight at 50° C. After evaporation of the solvent under reduced pressure, the residue is dissolved in methanol (5 ml) and applied to a pad (3 cm deep) of silica gel which is washed with methanol (500 ml) followed by acetic acid:methanol:water (3:2:1 by vol.). After evaporation of the solvent the residue is purified by column chromatography (silica gel Merck 60) using at first acetic acid:methanol:water (3:2:1 by vol.) and then pyridine:acetic acid (1:1 by vol.). The second fraction eluted is collected and dried under vacuum. The residue is dissolved in methanol (2 ml) and purified by chromatography on a column (2.5×40 cm) of Sephadex LH-20 which is eluted with n-butanol:acetic acid:water (5:1:4 by vol., upper phase). After removal of solvent under reduced pressure, the residue is dried under vacuum at 80° C. NMR spectroscopy indicates lo the product is contaminated with a small proportion of elimination products.

Compound 26

5,10,15-tris-[4-(3-Diethylamino-propyloxy)-phenyl]-20-(4-dodecyloxy-phenyl)-porphyrin

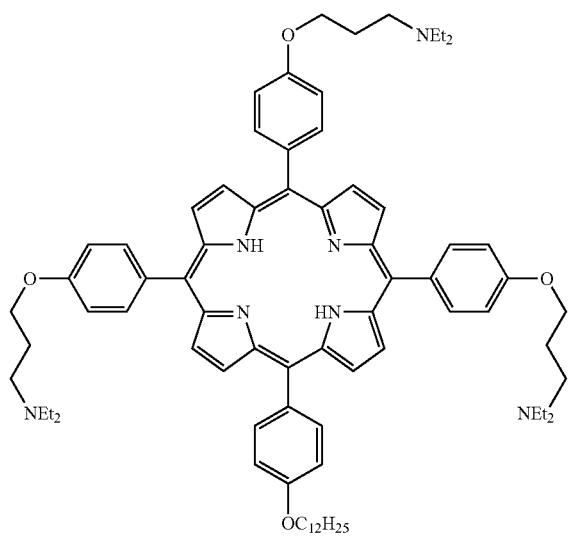

Compound 22 (50 mg, 0.06 mmol) and freshly distilled diethylamine (5 ml) are dissolved in absolute DMF (30 ml) under argon. The reaction mixture is stirred at room temperature for 20 h and poured into ethyl acetate (50 ml). The mixture is washed with water (4×50 ml) and, after drying the combined organic phases (Na$_2$SO$_4$), evaporation of solvent affords a residue which is purified by chromatography on a column (2.5×25 30 cm) of silica (Merck 60) which is eluted with ethyl acetate:n-hexane:triethyl amine (10:10:1, by vol.). Fractions are combined as appropriate, the solvent evaporated under reduced pressure and the residue dried under high vacuum. Treatment with dichloromethane:n-hexane affords pure product.

$^1$H-NMR:

$\delta_H$ (300 MHz, CDCl$_3$): 0.85 (t, $^3$J 7.5 Hz, 3H), 1.05 (m, 18H), 1.20-1.45 (m, 18H), 1.55 (quint, $^3$J 7.5 Hz, 2H), 2.15 (quint, $^3$J 7.5 Hz, 6H), 2.75 (quint, $^3$J 7.4 Hz, 6H), 3.15-3.25 (m, 12H), 4.15 (t, $^3$J 7.5 Hz, 2H), 4.25 (t, $^3$J 7.5 Hz, 6H), 7.15-7.20 (m, 8H), 8.00-8.05 (m, 8H), 7.95-8.0 (m, 8H).

Compound 27

5,15-bis-(3-Hydroxy-phenyl)-10-undecyl-porphyrin

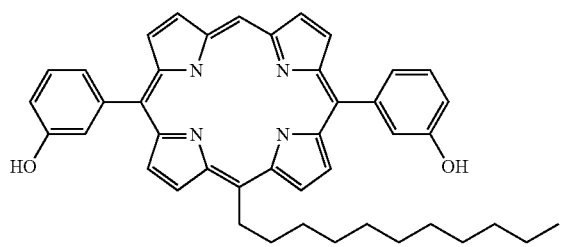

To a solution of Compound 24 (95 mg, 0.14 mmol) in anhydrous dichloromethane (80 mL) under an argon atmosphere BBr$_3$, (6 mL, 1M in dichloromethane) is added dropwise at −70° C. and the mixture is stirred for 1 h. The mixture is warmed to room temperature and stirred overnight then cooled to −10° C. and hydrolysed by addition of 2 mL water during 1 h. NaHCO$_3$ (3 g) is added directly to neutralisation. The mixture is stirred for a further 12 h. After removal of NaHCO$_3$ by filtration and of dichloromethane under vacuum, the residue obtained is purified by column chromatography using silica gel eluting with dichloromethane. After removal of solvent from appropriate combined fractions and drying under high vacuum the product is obtained as a violet solid.

$^1$H-NMR:

$\delta_H$ (300 Mz. CDCl$_3$): −3.05 (bs, 2H, s), 0.85 (t, $^3$J 7.5 Hz, 3H), 1.20-1.40 (m, 12H), 1.50 (m, 2H), 1.80 (quint, $^3$J 7.5 Hz, 2H), 2.55 (quint, $^3$J 7.5 Hz, 2H), 5.00 (t, $^3$J 7.5 Hz, 2H), 7.15-7.25, 7.50-7.60, 7.80-7.90 (3×m, 8H), 8.95-9.00, 9.20-9.25, 9.50-9.60 (3×m, 8H), 10.15 (s, 1H).

Compound 28

5,15-bis-[3-(3-Trimethylammmonio-propyloxy)-phenyl]-10-undecyl-porphyrin dichloride

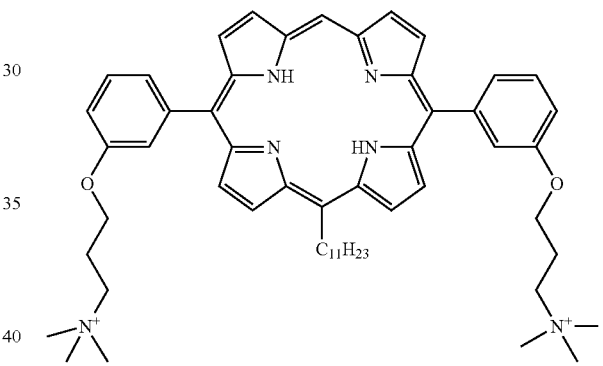

To a solution of Compound 27 (50 mg, 0.08 mmol) in DMF (20 mL) under an argon atmosphere K$_2$CO$_3$ (100 mg, 0.72 mmol) and (3-bromopropyl)-trimethylammonium bromide (300 mg, 1.2 mmol) are added and the mixture is stirred at 50° C. for 18 h. After removal of solvent under high vacuum the residue obtained is dissolved in methanol (5 mL) and filtered through a pad of silica gel (depth 2 cm) supported on a steel frit (diameter 3.5 cm). After washing the pad with methanol (500 mL) it is eluted with acetic acid:methanol:water (3:2:1, v:v). After drying of appropriate combined fractions under high vacuum the residue is dissolved in methanol and purified by column chromatography on Sephadex LH-20 eluting with n-butanol:acetic acid:water (5:1:4, by vol., upper phase). After evaporation of solvent the residue obtained from the first fraction eluted is dissolved in methanol and passed through a short column of anion exchange resin (Amberlite IRA 400, chloride form) to give, after evaporation of solvent the pure product.

$^1$H-NMR:

$\delta_H$ (300 Mz, CD$_3$OD): 0.85 (t, $^3$J 7.5 Hz, 3H), 1.20-1.40 (m, 12H), 1.50 (m, 2H), 1.80 (m, 2H), 2.40 (bs, 4H), 2.55 (m, 2H), 3.20 (bs, 18H), 3.65 (bs, 4H), 4.35 (bs, 4H), 5.10 (m, 2H), 7.50-7.55, 7.70-7.85 (2×m, 8H), 8.95-9.00, 9.25-9.24, 9.50-9.70 (3×bs, 8H), 10.15 (bs, 1H).

Compound 29

5,10-bis-[4-(3-Trimethylammonio-propyloxy)-phenyl]-15,20-bis-(4-undecyloxy-phenyl)-porphyrin dichloride

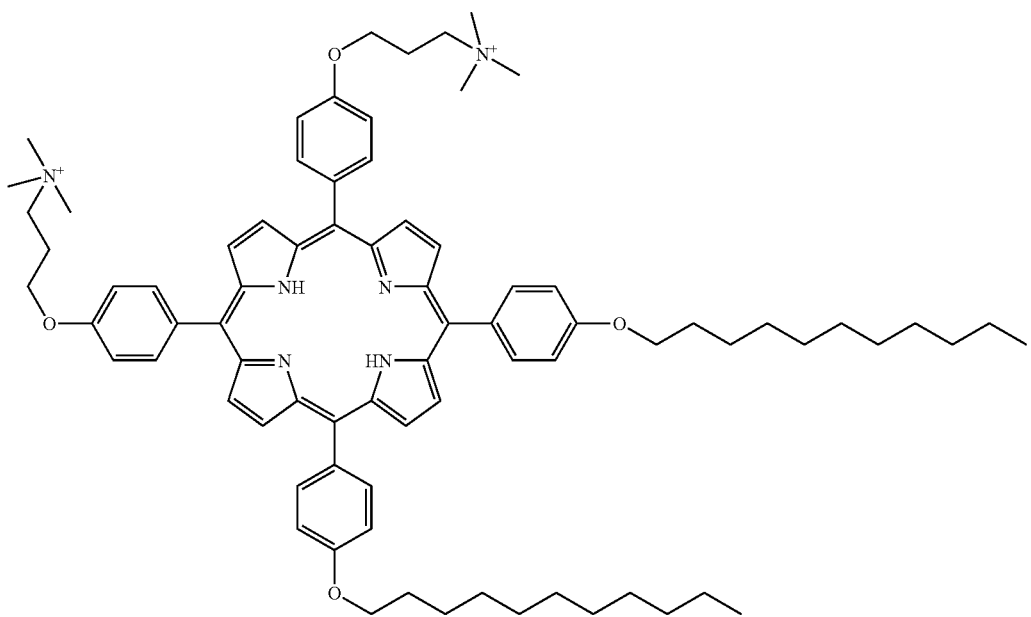

Compound 14 (50 mg, 0.05 mmol) is dissolved and $K_2CO_3$ (150 mg, 1.1 mmol) is suspended in DMF (30 mL). To the vigorously-stirred mixture a solution of (1-bromopropyl)-trimethylammonium bromide (0.3 g, 16.6 mmol) in DMF (10 mL) is added dropwise at 50° C. and the mixture is heated for 18 h. After removal of DM under high vacuum, the residue obtained is dissolved in methanol (5 mL) and filtered through a pad of silica gel (depth 2 cm) supported on a steel frit (diameter 3.5 cm). After washing the pad with methanol (ca. 500 mL) it is eluted with acetic acid:methanol:water (3:2:1, by vol.). After evaporation of solvent from appropriate combined fractions the residue obtained is purified by chromatography on a column (2.5×40 cm) of Sephadex LH-20 eluting with n-butanol:water:acetic acid (5:4:1, by vol., upper phase) for further separation from the excess ammonium salt and other by-products. After removal of solvent under reduced pressure the residue obtained is dissolved in methanol and passed through a short column (3.5×20 cm) of anion exchange resin (Amberlite IRA 400, chloride form). After evaporation of solvent under reduced pressure, the product is dried under high vacuum.

$^1$H-NMR:

$\delta_H$ (300 MHz, CD$_3$OD): 0.80 (t, $^3$J 7.5 Hz, 6H), 1.15-1.35 (m, 28H), 1.35-1.45 (bs, 4H), 1.70-1.80 (bs, 4H), 2.30-2.40 (bs, 4H), 3.15-3.30 (bs, 18H), 3.65-3.75 (bs, 4H), 4.00-4.05 (m, 4H), 4.30-4.40 (bs, 4H), 7.00-7.15, 7.20-7.30, 7.80-95, 7.95-8.15 (4×m, 4×4H), 8.60-9.00 (bs, 8H).

Compound 30

5,10,15-tris-(3-Hydroxy-phenyl)-20-(3-undecyloxy-phenyl)-porphyrin

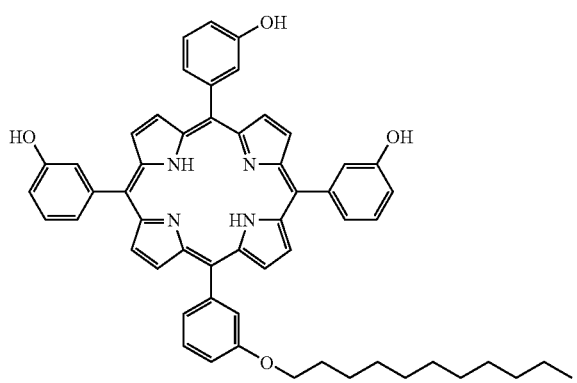

Pyrrole (1.31 g, 19.6 mmol) is added in one portion to a mixture of 3-hydroxybenzaldehyde (1.8 g, 14.8 mmol) and 3-undecyloxybenzaldehyde (1.36 g, 4.9 mmol) in acetic acid (145 mL) and nitrobenzene (118 g, 960 mmol) preheated to 130° C. and the mixture is stirred for 1 hour at 120° C. The mixture is cooled and solvent removed under high vacuum. The residue is dissolved in dichloromethane (5 mL) and purified by column chromatography using silica gel (Merck 60) eluting with hexane:toluene (4:1, by vol.). The product is obtained after removal of solvent from the eluate under reduced pressure and drying the obtained residue under vacuum.

¹H-NMR:

$\delta_H$ (300 Mz, CDCl$_3$): 0.75-0.80 (m, 3H), 1.05-1.35 (m, 14H), 1.40-1.50 (m, 2H), 1.75-1.85 (m, 2H), 3.90-4.10 (m, 2H), 6.90-7.70 (m, 16H), 8.45-8.80 (m, 8H).

Compound 31

5-{4-[3-Dimethyl-(3-Trimethylammonio-propyl)-ammonio-propyloxy]-phenyl}-15-(4-dodecyloxy-phenyl)-porphyrin dichloride

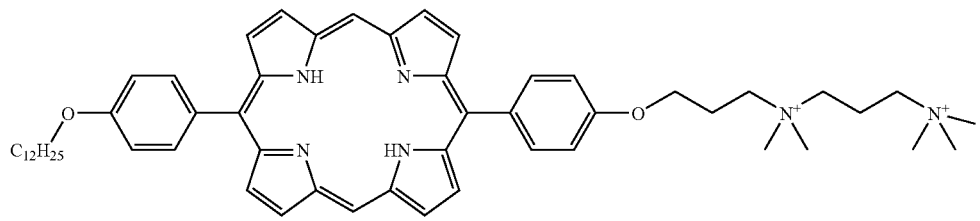

Compound 23 (50 mg, 0.055 mmol) is dissolved with methyl iodide (5 mL, 80 mmol) in absolute DMF(30 mL) and the mixture is stirred at 40° C. for 3 h. After evaporation of solvent the residue obtained is dissolved in methanol (5 mL) and filtered through a pad of silica gel (depth 2 cm) supported on a steel frit (diameter 3.5 cm). After washing the pad with methanol (ca. 1 L) it is eluted with dichloromethane:methanol (2:3 by vol., 500 mL) and then acetic acid:water:methanol (3:1:2, by vol.). After removal of solvent from appropriate pooled fractions the residue obtained is dissolved in acetic acid and purified by column chromatography on Sephadex LH-20 eluting with acetic acid. After evaporation of solvent from appropriate pooled fractions and drying the residue obtained under high vacuum, the residue is dissolved in methanol and passed through a small column (3.5×20 cm) of anion exchange resin (Amberlite IRA 400, chloride form). After evaporation of solvent from the eluate, the product is dried under high vacuum.

Compound 32

5-[4-(3-Dimethyldecyl-ammoniopropyloxy)-phenyl]-15-{4-[3-dimethyl-(3-dimethylaminopropyl)-ammoniopropyloxy]-phenyl}-porphyrin dichloride

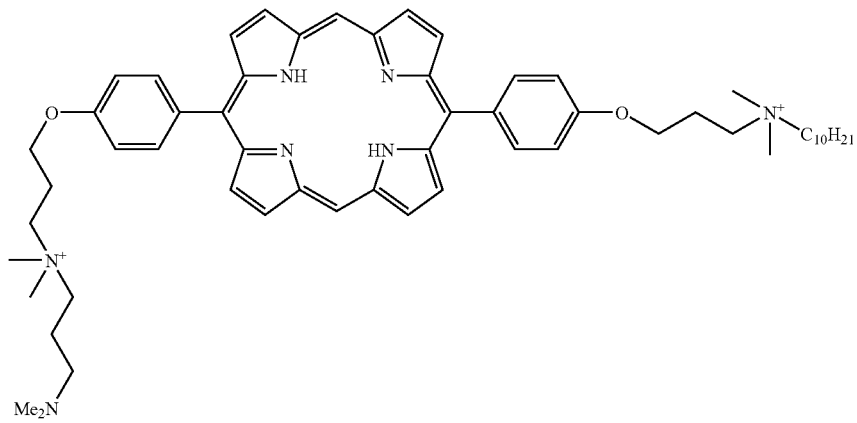

Compound 23 (50 mg, 0.068 mmol) is dissolved with N,N,N',N'-tetramethyl-1,3-propanediamine (354 mg, 1.36 mmol) and N,N-dimethyldecylamine (1 g, 2.72 mmol) in DMF:TBF(30 mL, 1:1, by vol.) and the mixture is stirred at 50° C. overnight. After evaporation of the solvent under reduced pressure the residue obtained is dissolved in methanol (10 mL) and filtered through a pad of silica gel (depth 2 cm) supported on a steel frit (diameter 3.5 cm). After washing the pad with methanol (ca. 500 mL) it is eluted with acetic acid:methanol:water (3:2:1, by vol.). The first two fractions eluted are combined and after evaporation of the solvent under reduced pressure the residue obtained is dissolved in methanol and purified by chromatography on a column (2.5× 40 cm) of Sephadex LH-20 eluting with n-butanol:water: acetic acid (4:5:1, by vol.). After removal of solvent under reduced pressure from the second fraction eluted, the residue is dissolved in methanol (5 mL) and passed through a short column (3.5×20 cm) of anion exchange resin (Amberlite IRA 400, chloride form). The eluate is evaporated to dryness and the residue obtained is dried under high vacuum to afford the product.

¹H-NMR:
$\delta_H$ (300 Mz, CD$_3$OD): 0.80 (m, 3H), 1.05-1.25 (m, 10H), 1.25-1.40 (bs, 2H), 1.80-1.90 (bs, 4H), 2.15-2.30 (bs, 2H), 2.80-3.60 (m, 20H), 3.80-3.95 (bs, 4H), 7.05-7.15, 7.85-8.00 (2×m, 2×4H), 8.75-8.90, 9.20-9.35 (2×bs,2×4H), 10.15 (bs, 2H).

Compound 33

5,10,15-tris[3-(3-Trimethyl-ammoniopropyloxy)-phenyl]-20-(3-undecyloxy-phenyl)-porphyrin trichloride

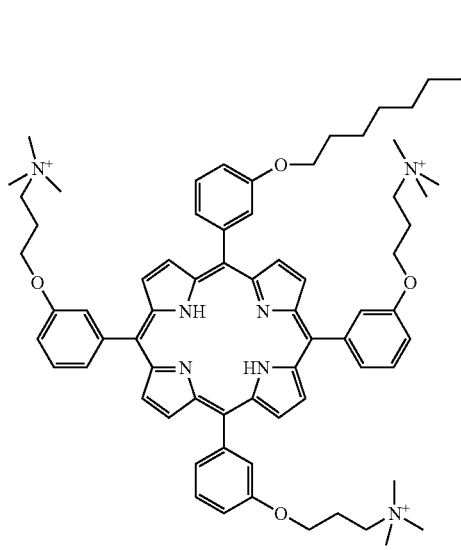

Compound 30 (100 mg, 0.12 mmol) is dissolved and K$_2$CO$_3$ (230 mg, 1.7 mmol) is suspended in DMF (30 mL). To the vigorously-stirred mixture a solution of (1-bromopropyl)-trimethylammonium bromide (0.3 g, 16.6 mmol) in DMF (10 mL) is added dropwise at 50° C. during 30 mins and the mixture is heated for 18 h. After removal of DWF under reduced pressure, the residue obtained is dissolved in methanol (5 mL) and filtered through a pad of silica gel (depth 2 cm) supported on a steel frit (diameter 3.5 cm). After washing the pad with methanol (ca. 500 mL) it is eluted with acetic acid: methanol:water (3:2:1, by vol.). After evaporation of solvent from appropriate combined fractions under reduced pressure. The residue is purified by chromatography on a column (2.5× 40 cm) of Sephadex LH-20 eluting with n-butanol:water: acetic acid (5:4:1, by vol., upper phase). After removal of solvent under reduced pressure from the eluate, the residue obtained is dissolved in methanol and the solution is passed through a short column (3.5×20 cm) of anion exchange resin (Amberlite IRA 400, chloride form). Evaporation of solvent from the eluate gives the product which is dried under high vacuum.

¹H-NMR:
$\delta_H$ (300 MHz, CD$_3$OD): 0.75-0.80 (m, 3H), 1.00-1.40 (m, 18H), 1.60-1.80 (bs, 2H), 2.25-2.40 (bs, 6H), 3.29 (bs, 27H), 3.40-3.60 (m, 6H), 3.90-4.00 (m, 2H), 4.05-4.25 (m, 6H), 7.10-7.20, 7.25-7.40, 7.60-7.80, 7.80-7.90 (4×m, 16H), 8.70-9.00 (bs, 8H).

Compound 34

5,15-bis-(3-Hydroxy-phenyl)-porphyrin

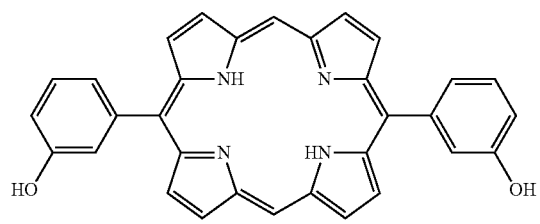

This is prepared as described by Wiehe, A., Simonenko, E. J., Senge, M. O. and Roeder, B. *Journal of Pophyrins and Phthalocyanines* 5, 758-761 (2001).

Compound 35

5,10,15-tris-(4-Hydroxy-phenyl)-20-(4-tetradecyloxy-phenyl)-porphyrin 5,10,15,20-tetrakis-(4-Hydroxy-phenyl)-porphyrin (170 mg, 0.25 mmol) is dissolved and K$_2$CO$_3$ (0.65 g, mmol) is suspended in DMF (30 mL). To the vigorously stirred reaction mixture a solution of 1-bromotetradecane (0.1 mL, 0.45 mmol) in DMF (10 mL) is added dropwise at 50° C. during 30 mins and the mixture is heated for 1.5 h. After evaporation of solvent, the residue is dissolved in toluene:ethanol (1:1 by vol., ca. 5 mL) and purified by chromatography using a column (5×25 cm) of silica gel (Merck 60) which is washed with toluene. After the elution of the first 3 fractions, elution is continued using toluene:ethyl acetate (2:1 by vol.). The fifth compound eluted is collected, the solvent evaporated and the residue dried under high vacuum to afford product as a violet solid.

¹H-NMR:

$\delta_H$ (300 MHz, d6-acetone): 0.85 (t, $^3J$ 7.5 Hz, 3H), 1.15-1.55 (m, 20H), 1.45 (quint, $^3J$ 7.5 Hz, 2H), 1.75 (quint, $^3J$ 7.5 Hz, 2H), 4.10 (t, $^3J$ 7.5 Hz, 2H), 7.20 (d, $^3J$ 8.5 Hz, 2H), 7.25 (d, $^3J$ 8.5 Hz, 6H), 8.00-8.15 (m, 8H), 8.80-9.10 (m, 8H).

Compound 36

5,10,15-tris-[4-(3-Trimethyl-ammoniopropyloxy)-phenyl]-20-(4-tetradecyloxy-phenyl)-porphyrin trichloride The n-tetradecyloxy-analogue of Compound 2, prepared similarly as described above for Compound 2 but using 1-bromotetradecane in place of 1-bromoundecane, (50 mg, 0.057 mmol) and (1-bromopropyl)-trimethylammonium bromide (210 mg, 0.8 mmol) are dissolved and $K_2CO_3$ (230 mg, 1.7 mmol) is suspended in DMF (20 mL). The vigorously stirred mixture is stirred at this temperature for 18 h. After removal of DMF under reduced pressure the residue obtained is dissolved in methanol (5 mL) and filtered through a pad of silica gel (depth 2 cm) is supported on a steel frit (diameter 3.5 cm). After washing the pad with methanol (ca. 500 mL) it is eluted with acetic acid:methanol:water (3:2:1, by vol.). After evaporation of the solvent from appropriately combined fractions, the residue obtained is purified by chromatography on a column (2.5×40 cm) of Sephadex LH-20 eluting with n-butanol:water:acetic acid (4:5:1, by vol., upper phase) for separation from the excess of ammonium salt and other contaminating materials. After elution and removal of the solvent from appropriate fractions, the residue obtained is dissolved in methanol (5 mL) and passed through a short column (3.5×20 cm) of anion exchange resin (Amberlite IRA 400, chloride form). Solvent is removed under reduced pressure and the residue obtained is dried under high vacuum to afford the product as a violet solid.

¹H-NMR:

$\delta_H$ (300 MHz, $CD_3OD$): 0.75 (t, $^3J$ 7.5 Hz, 3H), 0.95-1.25 (m, 22H), 1.50-1.65 (bs, 2H), 2.20-2.40 (bs, 6H), 3.05-3.15 (bs, 27H), 3.45-3.60 (bs, 6H), 3.60-3.80 (bs, 2H), 4.05-4.25 (bs, 6H), 6.80-7.25, 7.65-8.05, (2×m, 16H), 8.45-8.95 (bs, 8H).

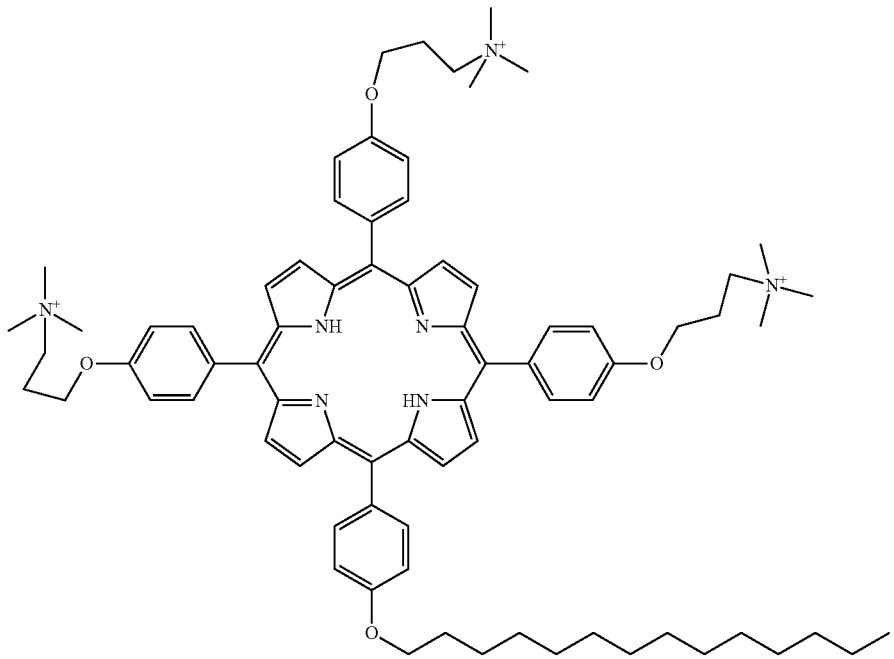

Compound 37

5-(4-{3-[2,4,6-tris-(Dimethylaminomethyl)-phenyloxy]-propyloxy}-phenyl)-15-(4-dodecyloxy-phenyl)-porphyrin

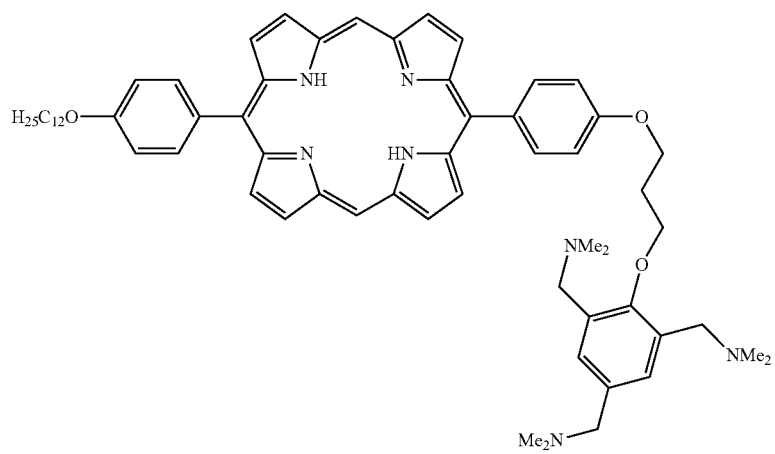

Compound 20 (50 mg, 0.063 mmol) is dissolved in DMF (20 mL) in the presence of 2,4,6-tris-(dimethylaminomethyl)-phenol (1 mL, 3.7 mmol) and stirred at 50° C. overnight. After evaporation of the solvent, the residue is solidified by treatment of the residue with dichloromethane:methanol to remove the excess of amine. After filtration, the porphyrins are re-dissolved in dichloromethane and purified by chromatography on a column of silica gel (Merck 60) which is washed with dichloromethane. Evaporation of solvent under reduced pressure and treatment of the residue with dichloromethane:methanol gives the product as a violet solid.

$^1$H-NMR:

$\delta_H$ (300 Mz, CDCl$_3$): −3.15 (2H, s), 0.85 (t, $^3$J 4.5 Hz, 3H), 1.20-1.40 (m, 18H), 1.55 (quint, $^3$J 4.5 Hz, 2H), 1.90 (quint, $^3$J 4.5 Hz, 2H), 2.20 (s, 18H), 2.55 (t, $^3$J 5.2 Hz, 2H), 3.45 (s, 6H), 4.15 (t, $^3$J 5.5 Hz, 2H), 4.20 (t, $^3$J 5.5 Hz, 2H), 4.35 (t, $^3$J 7.5 Hz, 2H), 6.85 (2×s, 2H), 7.20-7.30, 8.10-8.15 (2×m, 8H), 9.00-9.05, 9.25-9.30 (2×m, 2×4H), 10.20 (s, 2H).

Compound 38

5,10,15-tris-(4-Hydroxy-phenyl)-20-(4-decyloxy-phenyl)-porphyrin

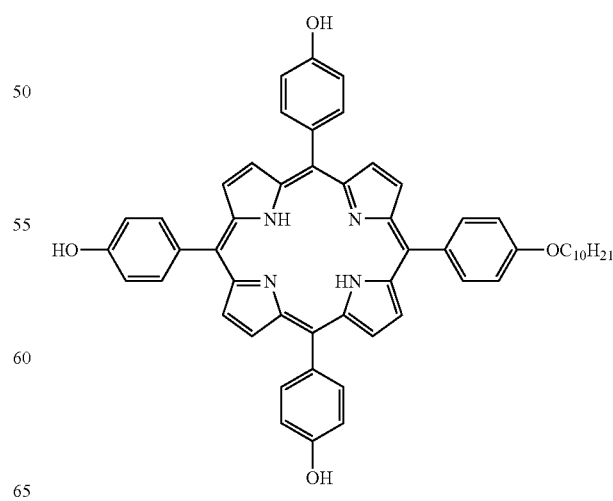

5,10,15,20-tetrakis-(4-Hydroxy-phenyl)-porphyrin (100 mg, 0.15 mmol) is dissolved and K$_2$CO$_3$ (230 mg) is suspended in DMF (30 mL). To the vigorously stirred reaction mixture a solution of 1-bromodecane (0.016 mL, 0.11 mmol) in DMF (10 mL) is added dropwise at 70° C. during 30 mins and the mixture is stirred for 1.5 h. After evaporation of solvent, the residue is dissolved in toluene:ethanol (1:1 by vol., ca. 3 mL) and purified by chromatography on a column (150 g) of silica gel (Merck 60) using toluene as eluent. After elution of the first 3 fractions, the column is eluted with toluene:ethyl acetate (2:1 by vol.) and the 5th fraction eluted is collected, the solvent removed and the residue dried under high vacuum to give the product as a violet solid.

¹H-NMR:

$\delta_H$ (300 Mz, d6-acetone): 0.95 (t, ³J 7.5 Hz, 3H), 1.25-1.55 (m, 12H), 1.55 (quint, ³J7.5 Hz, 2H), 1.85 (quint, ³J 7.5 Hz, 2H), 4.15 (t, ³J 7.5 Hz, 2H), 7.20 (d, ³J 8.5 Hz, 2H), 7.25 (d, ³J 8.5 Hz, 6H), 8.00-8.15 (m, 8H), 8.80-9.10 (m, 8H).

Compound 39

5,10,15-tris-[4-(3-Trimethylammonio-propyloxy)-phenyl]-20-(4-decyloxy-phenyl)-porphyrin trichloride Compound 38 (50 mg, 0.061 mmol) and (1-bromopropyl)-trimethylammonium bromide (210 mg, 0.8 mmol) are dissolved and K₂CO₃ (230 mg, 1.7 mmol) is suspended in DMF (20 mL). The vigorously stirred reaction mixture is heated at 50° C. for 18 h. After evaporation of solvent, the raw product is dissolved in methanol and purified by chromatography on a column (2.5×40 cm) of Sephadex, eluting with n-butanol:water:acetic acid (4:5:1, by vol., upper phase). After removal of the solvent, the residue is dissolved in methanol and passed through a column (3.5×20 cm) of Amberlite IRA-400 (chloride form). After evaporation of solvent, the product is dried under high vacuum and yields a violet solid.

¹H-NMR:

$\delta_H$ (300 MHz, CD₃OD): 0.90 (t, ³J 7.5 Hz, 3H), 1.20-1.40 (m, 12H), 1.45-1.60 (bs, 2H), 1.80-1.90 (bs, 2H), 2.45-2.55 (bs, 6H), 3.25-3.35 (bs, 27H), 3.75-3.85 (bs, 6H), 4.05-4.25 (m, 2H), 4.35-4.40 (bs, 6H), 7.10-7.40, 7.95-8.15 (2×m, 16H), 8.60-9.00 (bs, 8H).

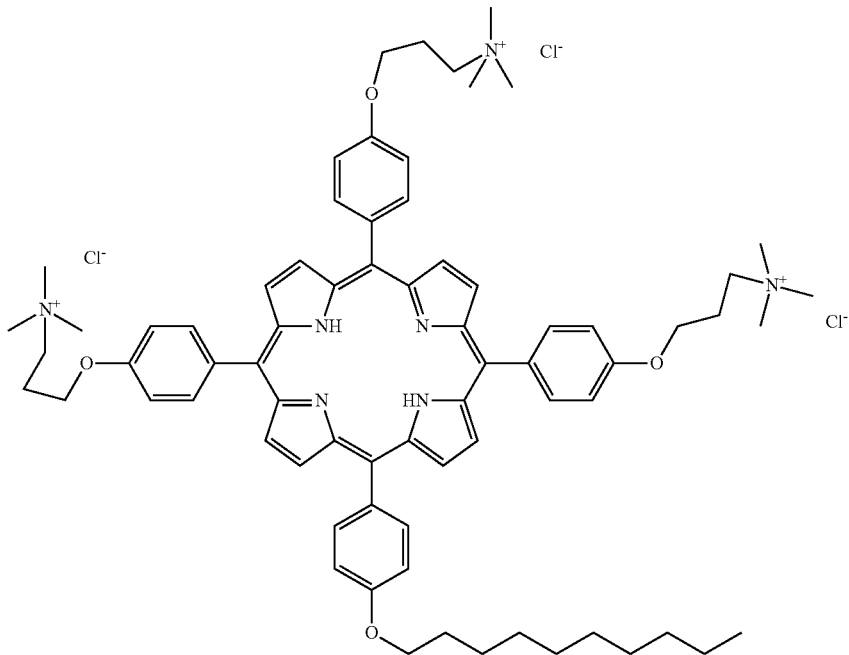

Compound 40

5,10,15-tris-(4-Hydroxy-phenyl)-20-(4-tridecyloxy-phenyl)-porphyrin

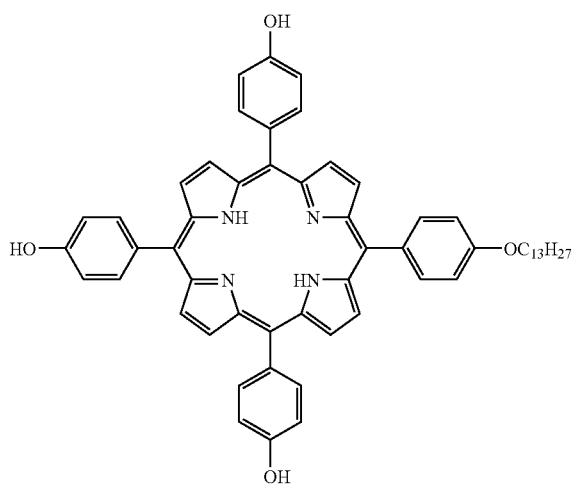

5,10,15,20-tetrakis-(4-Hydroxy-phenyl)-porphyrin (400 mg, 0.59 mmol) is dissolved and $K_2CO_3$ (1.0 g, 7.1 mmol) is suspended in DMF (75 mL). To the vigorously stirred reaction mixture a solution of 1-bromotridecane (0.1 mL, 0.45 mmol) in DMF (10 mL) is added dropwise at 50° C. during 30 mins and the mixture is then heated for 1.5 h. The reaction mixture is cooled to room temperature and poured into water (150 mL). The porphyrins are extracted with ethyl acetate (100 mL) and the extract washed with brine (3×50 mL) and dried ($Na_2SO_4$). After evaporation of solvent, the residue is dissolved in toluene:ethanol (1:1, by vol., ca. 10 mL) and purified by chromatography using a column (200 g) of silica gel (Merck 60) with toluene as the eluent. After the elution of the first three compounds, the eluent is changed to toluene:ethyl acetate (2:1, by vol.). The fifth compound eluted is collected and dried under high vacuum to yield product as a violet solid.

$^1$H-NMR:

$\delta_H$ (300 Mz, d6-acetone): 0.85 (t, $^3$J 7.5 Hz, 3H), 1.20-1.60 (m, 18H), 1.50 (quint, $^3$J 7.5 Hz, 2H), 1.80 (quint, $^3$J 7.5 Hz, 2H), 4.14 (t, $^3$J 7.5 Hz, 2H), 7.20 (d, $^3$J 8.5 Hz, 2H), 7.25 (d, $^3$J 8.5 Hz, 6H), 8.00-8.15 (m, 8H), 8.80-9.10 (m, 8H).

Compound 41

5-(4-Tridecyloxy-phenyl)-10,15,20-tris-[4-(3-trimethylammonio-propyloxy)-phenyl]-porphyrin trichloride

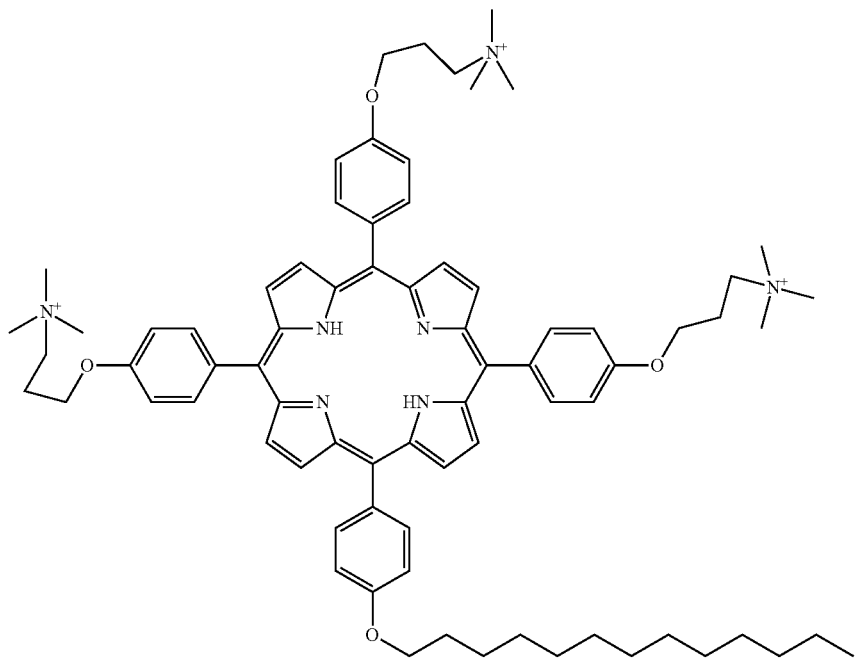

Compound 40 (50 mg, 0.057 mmol) and (1-bromopropyl)-trimethylammonium bromide (210 mg, 0.8 mmol) are dissolved and $K_2CO_3$ (230 mg, 1.7 mmol) is suspended in DMF (20 mL). The vigorously stirred reaction mixture is heated at 50° C. for 18 h. After removal of DMF, the residue is dissolved in methanol (5 mL) and applied to a pad (2 cm thick) of silica gel which is washed with methanol (ca. 1000 mL) and then eluted with acetic acid:methanol:water (3:2:1 by vol.). After evaporation of the solvent the residue is dissolved in methanol and further purified by chromatography on a column (2.5×40 cm) of Sephadex LH-20 which is eluted with n-butanol:water:acetic acid (4:5:1 by vol., upper phase). After removal of solvent, the residue is dissolved in methanol and passed through a short column (3.5×20 cm) of anion exchange resin (Amberlite IRC 400, chloride form). After evaporation of solvent, the product is dried under high vacuum to afford a violet solid.

$^1$H-NMR:

$\delta_H$ (300 MHz, $CD_3OD$): 0.90 (t, $^3J$ 7.5 Hz, 3H), 1.20-1.40 (m, 18H), 1.45-1.60 (m, 2H), 1.80-1.90 (bs, 2H), 2.40-2.55 (bs, 6H), 3.25-3.35 (bs, 27H), 3.75-3.85 (bs, 6H), 4.05-4.25 (m, 2H), 4.35-4.40 (bs, 6H), 7.10-7.40, 7.90-8.15 (2×m, 16H), 8.60-9.00 (bs, 8H).

Compound 42

5,15-bis-(4-Hydroxy-phenyl)-porphyrin

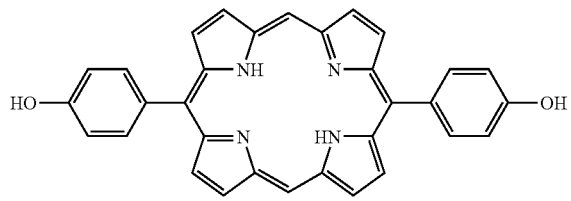

This is prepared as described by Mehta, Goverdhan; Muthusamy, Sengodagounder; Maiya, Bhaskar G.; Arounaguiri, S., *J. Chem.Soc.Perkin Trans.*1; 2177-2182 (1999).

Compound 43

5,10,15-tris-(4-Hydroxy-phenyl)-20-(4-octyloxy-phenyl)-porphyrin

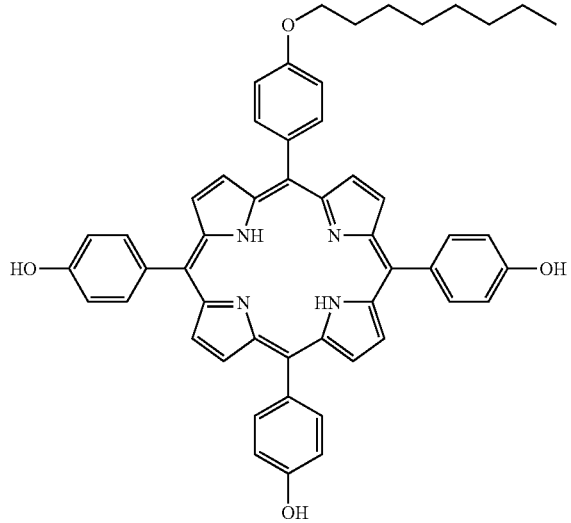

5,10,15,20-tetrakis-(4-Hydroxy-phenyl)-porphyrin (200 mg, 0.294 mmol) is dissolved and potassium carbonate (487 mg, 3.53 mmol, 12 eqv.) in suspended under argon in absolute DMF (50 mL) and the mixture is heated to 55° C. A solution of octal bromide (35.8 µl, 0.206 mmol, 0.7 eqv.) in absolute DMF (10 mL) is added dropwise during 30 min. and the mixture is stirred at 55° C. for 2 h. The solvent is removed in vacuo at 50° C., water (80 mL) is added and the mixture is extracted with ethyl acetate (3×40 mL). The combined organic fraction is dried ($Na_2SO_4$) and the solvent evaporated. The residue is purified by chromatography on a column (300 g) of silica gel. Tetra-alkylated and tri-alkylated compounds are eluted with toluene:ethyl acetate (30:1 by vol.). The third fraction (di-substituted compound, trans-isomer) is eluted with toluene:ethylacetate (15:1 by vol.). The fourth fraction (di-substituted compound, cis-isomer) is eluted with toluene:ethyl acetate (10:1 by vol.) and the desired product (mono-alkylated compound) is eluted with toluene:ethylacetate (5:1 by vol.). The solvent is removed under reduced pressure and the residue dried under high vacuum to give the product as a violet solid.

$^1$H-NMR:

$\delta_H$ (300 MHz, d6-acetone): 0.75 (t, 3H, $^3J$=6.8 Hz), 1.13-1.25 (m, 8H), 1.43 (quint, 2H, $^3J$=7.5 Hz), 1.73 (quint, 2H, $^3J$=7.5 Hz), 3.50 (t, 2H, $^3J$=8 Hz), 7.11 (d, 2H, $^3J$=7.5 Hz), 7.16 (d, 6H, $^3J$=7.5 Hz), 7.90-7.94 (m, 8H), 8.80-8.90 (m, 8H)

Compound 44

5-(4-Dodecyloxy-phenyl)-10,15,20-tris-(4-hydroxy-phenyl)-porphyrin

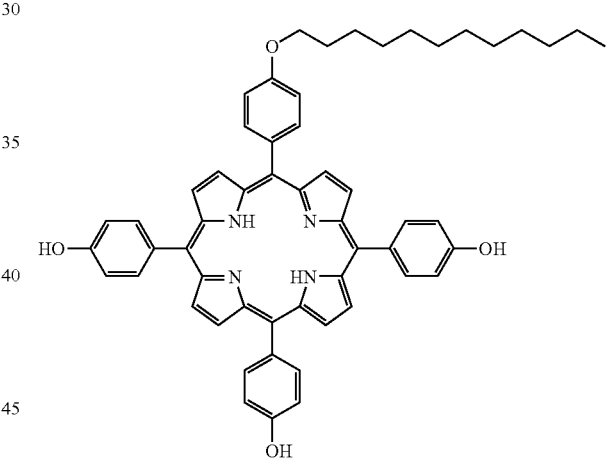

5,10,15,20-tetrakis-(4-Hydroxy-phenyl)-porphyrin (200 mg, 0.294 mmol) is dissolved and potassium carbonate (487 mg, 3.53 mmol, 12 eqv.) in suspended under argon in absolute DMF (50 mL) and the mixture is heated to 55° C. A solution of dodecyl bromide (49.4 µl, 0.206 mmol, 0.7 eqv.) in absolute DMF (10 mL) is added dropwise during 30 min. The mixture is stirred at 55° C. for 2 h. The solvent is removed in vacuo at 50° C., water (80 mL) is added and the mixture extracted with ethyl acetate (3×40 mL). The combined organic fractions are dried ($Na_2SO_4$) and the solvent evaporated. The product is isolated by chromatography on a column (300 g) of silica. Tetra-alkylated and tri-alkylated compounds are eluted with toluene:ethyl acetate (30:1 by vol.), di-substituted compound (trans-isomer) with toluene:ethyl acetate (15:1 by vol.), di-substituted compound (cis-isomer) with toluene:ethyl acetate (10:1 by vol.) and the desired product (mono-alkylated compound) with toluene:ethyl acetate (5:1 by vol). Solvent is removed in vacuo and the residue dried at high vacuum to give product as a violet solid.

¹H-NMR:

δ$_H$ (300 MHz, d6-acetone): 0.75 (t, 3H, $^3$J=6.8 Hz), 1.13-1.25 (m, 16H), 1.41 (quint, 2H, $^3$J=7.5 Hz), 1.63 (quint, 2H, $^3$J=7.5 Hz), 3.89 (t, 2H, $^3$J=6 Hz), 7.11 (d, 2H, $^3$J=7.5 Hz), 7.16 (d, 6H, $^3$J=7.5 Hz), 7.9-7.94 (m, 8H), 8.78-8.83 (m, 8H)

Compound 45

5,10,15-tris-(4-Hydroxy-phenyl)-20-(4-nonyloxy-phenyl)-porphyrin

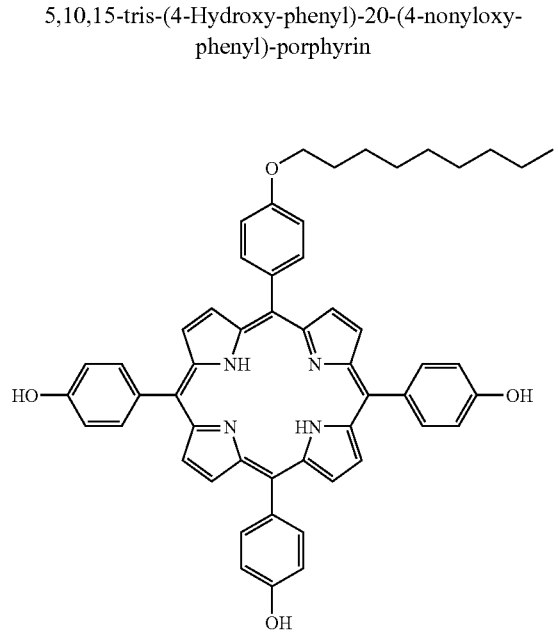

5,10,15,20-tetrakis-(4-Hydroxy-phenyl)-porphyrin (200 mg, 0.294 mmol) is dissolved and potassium carbonate (487 mg, 3.53 mmol, 12 eqv.) is suspended under argon in absolute DMF (50 mL) and the mixture heated to 55° C. A solution of nonyl bromide (49.4 µl, 0.206 mmol, 0.7 eqv.) in absolute DMF (10 mL) is added dropwise during 30 min. The mixture is stirred at 55° C. for 2 h. The solvent is removed in vacuo at 50° C., water (80 mL) is added and the mixture extracted with ethyl acetate (3×40 mL). The combined organic extracts are dried (Na$_2$SO$_4$) and solvent removed under reduced pressure. The product is isolated by chromatography on a column (300 g) of silica. Tetra-alkylated and tri-alkylated compounds are eluted with toluene:ethyl acetate (30:1 by vol.), di-substituted compound (trans-isomer) with toluene:ethyl acetate (15:1 by vol.). di-substituted compound (cis-isomer) with toluene:ethyl acetate (10:1 by vol.) and the desired product (mono-alkylated compound) is eluted with toluene:ethyl acetate (5:1 by vol.). The solvent is removed under reduced pressure and the residue dried at high vacuum to afford the product as a violet solid.

¹H-NMR:

δ$_H$ (300 MHz, d6-acetone): 0.87 (t, 3H, $^3$J=7.5 Hz), 1.14-1.26 (m, 10H), 1.41 (quint, 2H), 1.70 (quint, 2H, $^3$J=7.5 Hz), 3.92 (t, 2H, $^3$J=7.5 Hz), 7.02 (d, 2H, $^3$J=8.25 Hz,), 7.15 (d, 6H, $^3$J=7.5 Hz,), 7.85 (d, 2H, $^3$J=8.25 Hz), 7.91 (d, 2H, $^3$J=7.5 Hz), 8.76-8,84 (m, 8H)

Compound 46

5-(4-Octyloxy-phenyl)-10,15,20-tris-[4-(3-trimethylammonio-propyloxy)-phenyl]-porphyrin trichloride

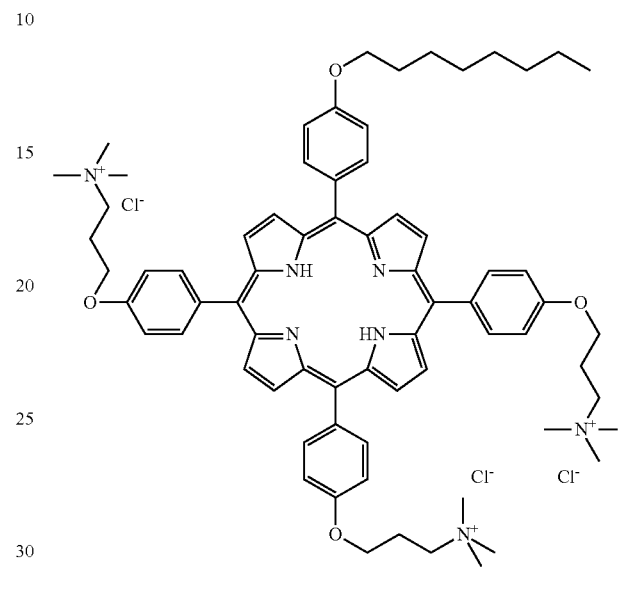

Compound 43 (50 mg, 0.063 mmol) and (3-bromopropyl)-trimethylammonium bromide (164 mg, 0.63 mmol, 10 eqv.) are dissolved and potassium carbonate (130 mg, 0.95 mmol, 15 eqv.) is suspended under argon in absolute DMF (30 mL) and the mixture is stirred at 55° C. for 12 h. The solvent is removed in vacuo at 50° C. and the residue applied to a pad (2 cm deep) of silica. The unreacted ammonium salts are washed off with methanol (1000 mL) and the product is eluted with acetic acid:methanol:water (3:2:1 by vol.). The solvent is removed under reduced pressure and the residue further purified by chromatography on a column (100 g) of Sephadex LH-20 using n-butanol:water:acetic acid (4:5:1 by vol., upper phase) as the eluent. The solvents are removed under reduced pressure and the residue dissolved in methanol and passed through a small column of anion exchange resin (Amberlite IRA 400, chloride form) using methanol as eluent. After evaporation of solvent, the crude product is dissolved in the minimum amount of methanol and diethylether (50 mL) added. The solution is centrifuged for 15 min. The supernatant liquid is evaporated to dryness and the residue dried at high vacuum to give the product as a violet solid.

¹H-NMR:

δ$_H$ (300 MHz, CD$_3$OD): 0.90 (t, 3H, $^3$J=7.5 Hz), 1.25-1.41 (m, 8H), 1.45 (bs, 2H), 1.87 (bs, 2H), 2.38 (bs, 6H), 3.29 (bs, 27H), 3.67 (t, 6H, $^3$J=7.5 Hz), 4.01 (t, 2H, $^3$J=7.5 Hz), 4.30 (t, 6H, $^3$J=7.5 Hz), 7.11 (d, 2H, $^3$J=7.5 Hz), 7.38 (d, 6H, $^3$J=7.5 Hz), 7.95 (d, 2H, $^3$J=7.5 Hz), 8.11 (d, 6H, $^3$J=7.5 Hz), 8.93 (bs, 8H)

Compound 47

5-(4-Dodecyloxy-phenyl)-10,15,20-tris-[4-(3-trimethylammonio-propyloxy)-phenyl]-porphyrin trichloride

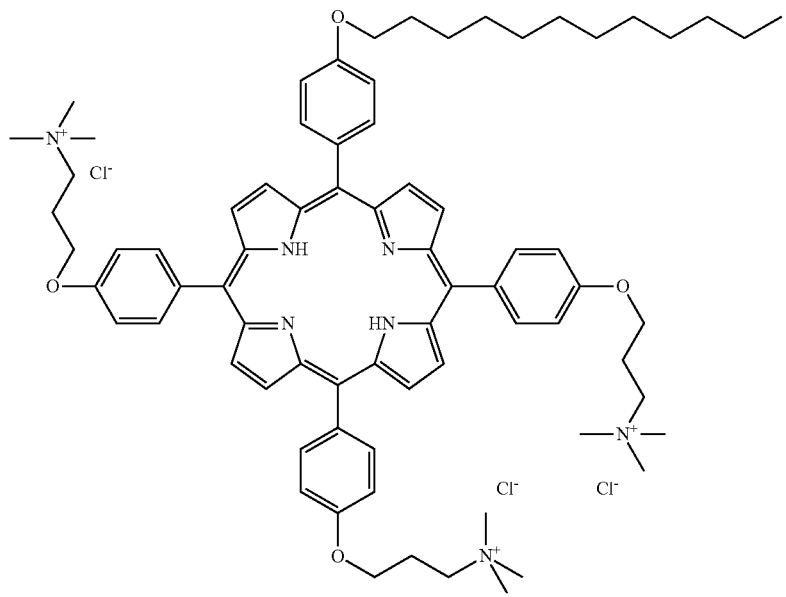

Compound 44 (50 mg, 0.059 mmol) and (3-bromopropyl)-trimethylammonium bromide (154 mg, 0.59 mmol, 10 eqv.) are dissolved and potassium carbonate (122 mg, 0.885 mmol, 15 eqv.) is suspended under argon in absolute DMF (30 mL) and the mixture is stirred at 55° C. for 12 h. The solvent is removed in vacuo at 50° C. and the residue re-dissolved in a little methanol and applied to a pad of silica (2 cm deep).

The unreacted ammonium salts are washed off with methanol (1000 mL). The product is eluted with acetic acid:methanol:water (3:2:1 by vol.). The solvents are removed under reduced pressure and the crude product further purified by chromatography on a column (100 g) of Sephadex LH-20 using n-butanol:water:acetic acid (4:5:1 by vol., upper phase) as eluent. The solvents are removed under reduced pressure, the residue re-dissolved in a little methanol and the solution passed through a short column of anion exchange resin (Amberlite IRC 400, chloride form) using methanol as eluent. After removal of solvent the crude product is re-dissolved in the minimum amount of methanol and diethyl ether (50 mL) added. The solution is centrifuged for 15 min. The supernatant liquid is evaporated to dryness and the product dried at high vacuum to give a violet solid.

$^1$H-NMR:

$\delta_H$ (300 MHz, CD$_3$OD): 0.88 (t, 3H, $^3J$=7.5 Hz), 1.25-1.37 (m, 16H), 1.48 (bs, 2H), 1.93 (bs, 2H), 2.42 (bs, 6H), 3,28 (bs, 27H), 3.68-3.75 (m, 6H), 4.05 (t, 2H), 4.33 (t, 6H), 7.17 (d, 2H, $^3J$=7.5 Hz), 7.33 (d, 6H, $^3J$=7.5 Hz), 7.99 (d, 2H, $^3J$=7.5 Hz), 8.08 (d, 6H, $^3J$=7.5 Hz), 8.85 (bs, 8H)

Compound 48

5-(4-Nonyloxy-phenyl)-10,15,20-tris-[4-(3-trimethylammonio-propyloxy)-phenyl]-porphyrin trichloride

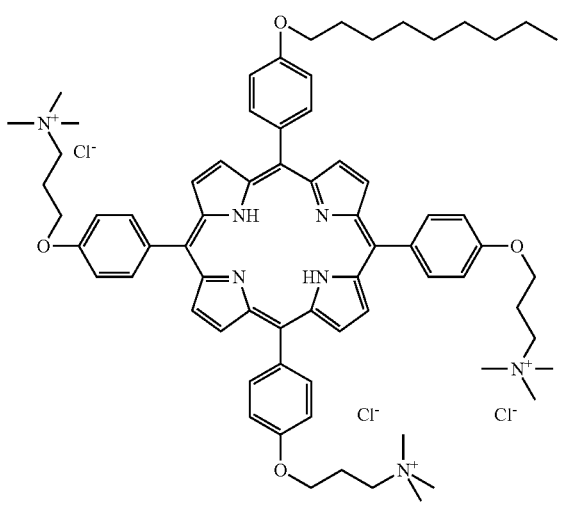

Compound 45 (50 mg, 0.062 mmol) and (3-bromopropyl)-trimethylammonium bromide (162 mg, 0.62 mmol, 10 eqv.) are dissolved and potassium carbonate (128 mg, 0.93 mmol, 15 eqv.) is suspended under argon in absolute DMF (30 mL) and the mixture is stirred at 55° C. for 12 h. The solvent is removed in vacuo at 50° C. and the residue re-dissolved in a little methanol and applied to a pad of silica (2 cm deep). The unreacted ammonium salts are washed off with methanol (1000 mL). The product is eluted with acetic acid:methanol:water (3:2:1 by vol.). The solvents are removed under reduced pressure and the product further purified by chromatography on a column (100 g) of Sephadex LH-20 eluting with n-butanol:water:acetic acid (4:5:1 by vol., upper phase). The solvents are removed under reduced pressure, the residue re-dissolved in a little methanol and the solution is passed through a short column of anion exchange resin (Amberlite IRC 400, chloride form) using methanol as eluent. After removal of solvent, the product is dried at high vacuum to give a violet solid.

¹H-NMR:

$\delta_H$ (300 MHz, CD$_3$OD): 0.89 (t, 3H, $^3J$=7.5 Hz), 1.18-1.34 (m, 10H), 1.41 (bs, 2H), 1.73 (quint. 2H, $^3J$=7.5 Hz), 2.30-2.44 (m, 6H), 3,31 (bs, 27H), 3.65-3.73 (m, 6H), 3.93 (t, 2H, $^3J$=7.5 Hz), 4.25-4.42 (m, 6H), 7.08 (d, 2H, $^3J$=7.5 Hz), 7.30 (d, 6H, $^3J$=7.5 Hz), 7.93 (d, 2H, $^3J$=7.5 Hz), 8.05 (d, 6H, $^3J$=7.5 Hz), 8.94 (bs, 8H)

Compound 49

5-(4-Octyloxy-phenyl)-10,15,20-tris-[4-(5-trimethylammonio-pentyloxy)-phenyl]-porphyrin trichloride

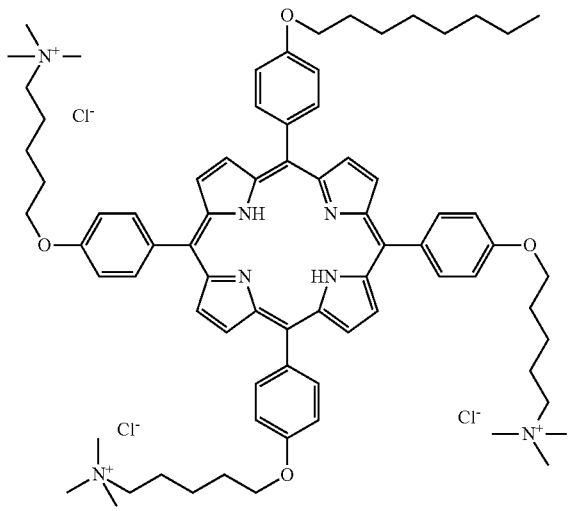

Compound 43 (23 mg, 0.03 mmol) and (5-bromopentyl)-trimethylammonium bromide (84 mg, 0.3 mmol, 10 eqv.) are dissolved and potassium carbonate (62 mg, 0.45 mmol, 15 eqv.) is suspended under argon in absolute DMF (15 mL) and the mixture is stirred at 55° C. for 12 h. The solvent is removed in vacuo at 50° C. and the residue re-dissolved in a little methanol and applied to a pad (2 cm deep) of silica. The unreacted ammonium salts are washed off with methanol (1000 mL). The product is eluted with acetic acid:methanol:water (3:2:1 by vol.). The solvents are removed under reduced pressure and the product further purified by chromatography on a column (100 g) of Sephadex LH-20 using n-butanol:water:acetic acid (4:5:1 by vol., upper phase) as eluent. The solvents are removed under reduced pressure, the residue re-dissolved in a little methanol and the solution passed though a short column of anion exchange resin (Amberlite IRC 400, chloride form) with methanol as eluent. The complete purification process is repeated if impurities remain in the product. After removal of solvent, the residue is 5 dried at high vacuum to give the product as a violet solid.

¹H-NMR:

$\delta_H$ (300MHz, CD$_3$OD): 0.78 (bs, 3H), 1.08-1.35 (m, 10H), 1.45-1.59 (m, 6H), 1.63-1.93 (m, 14H), 3.17-3.32 (m, 6H), 3.31 (bs, 33H), 3.84 (bs, 2H), 4.07 (bs, 6H), 6.93 (bs, 2H), 7.09 (d, 2H, $^3J$=7.5 Hz), 7.74 (bs, 2H), 7.88 (d, 2H, $^3J$=7.5 Hz), 8.71 (bs, 8H)

Compound 50

5,10,15-tris-[4-(5-Trimethylammonio-pentyloxy)-phenyl]-20-(4-undecyloxy-phenyl)-porphyrin trichloride

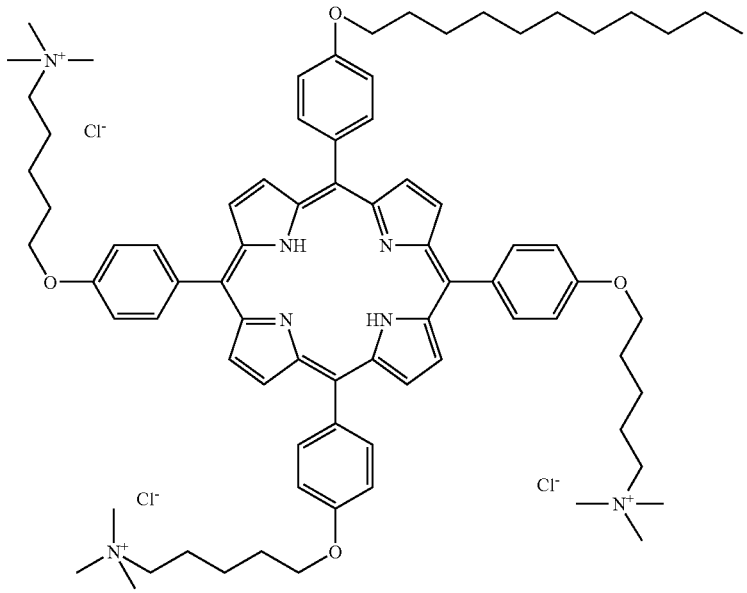

Compound 2 (50 mg, 0.06 mmol) and (5-bromopentyl)-trimethylammonium bromide (174 mg, 0.6 mmol, 10 eqv.) are dissolved and potassium carbonate (124 mg, 0.9 mmol, 15 eqv.) is suspended under argon in absolute DMF (30 mL) and the mixture is stirred at 55° C. for 12 h. The solvent is removed in vacuo at 50° C. and the residue re-dissolved in a little methanol and applied to a pad (2 cm deep) of silica. The unreacted ammonium salts are washed off with methanol (1000 mL). The product is eluted with acetic acid:methanol:water (3:2:1 by vol.). Solvents are removed under reduced pressure and the product further purified by chromatography on a column (100 g) of Sephadex LH-20 eluting with n-butanol:water:acetic acid (4:5:1 by vol., upper phase). Solvents are removed under reduced pressure, the residue re-dissolved in the minimum of methanol and the solution passed through a short column of anion exchange resin (Amberlite IRC 400) with methanol as eluent. The complete purification process is repeated if impurities remain in the product. After removal of solvent, the residue is dried at high vacuum to give the product as a violet solid.

$^1$H-NMR:

$\delta_H$ (300MHz, MeOD): 0.71-0.88 (m, 13H), 0.91-1.38 (m, 14H), 1.48-1.81 (m, 12H), signals for —CH$_2$NCH$_2$ and OCH$_2$-long alkyl chain are part of the multiplet together with the signals for solvent in the area 2.8-3.3, 3.91 (bs, 6H), 6.33 (bs, 2H), 6.86 (bs, 6H), 7.35 (bs, 2H), 7.70 (bs, 6H), 8.65 (bs, 8H)

Compound 51

5,10,15,20-tetrakis-(3-Dodecyloxy-phenyl)-porphyrin

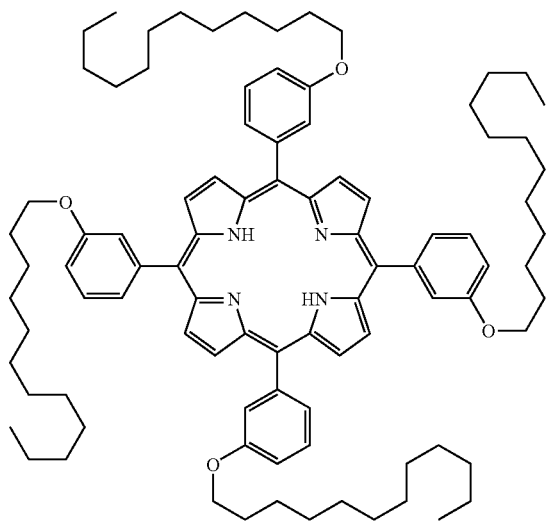

Pyrrole (0.7 mL, 10 mmol) and 3-dodecyloxybenzaldehyde (2.91 g, 10 mmol) are dissolved in degassed dichloromethane (1000 mL) and TFA (0.77 mL, 10 mmol) is added dropwise. The mixture is stirred for 17 h at room temperature in the dark. DDQ (6.81 g, 30 mmol) is added in one portion and the mixture is stirred for a further 1 h at room temperature. The mixture is filtered through a column (400 g) of silica using dichloromethane as eluent followed by dichloromethane to which triethylamine is added to adjust the pH value to 8. This purification process is repeated if impurities remain in the product until the pure product is obtained.

$^1$H-NMR:

$\delta_H$ (300 MHz, d6-acetone): 0.80 (bs, 12H), 1.03-1.45 (m, 80H), 1.78 (quint., 8H, $^3$J=7.5 Hz), 4.05 (t, 8H, $^3$J=7.5 Hz), 7.24 (d, 4H, $^3$J=7.5 Hz), 7.49-7.55 (m, 4H), 7.68-7.71 (m, 8H), 8.80 (m, 8H)

Example B

Innate Anti-Bacterial Activity of Compound 10—Determination of Minimum Inhibitory Concentration (MIC) and Minimum Bacteriocidal Concentration (MBC)

The minimum inhibitory concentration (MIC) for an antimicrobial agent against a specific microorganism is defined as the minimum concentration of an antibacterial agent where no apparent visible growth of the organism is observed (FDA definition of Minimum Inhibitory Concentration). MIC's are typically determined using concentrations derived traditionally from serial twofold dilutions (National Committee for Clinical Laboratory Standards (NCCLS) Handbook M7-A5: "Methods for Dilution Antimicrobial Susceptibility Tests for Bacteria that Grow Aerobically; Approved Standard—5$^{th}$ Edition" Volume 20 Number 2. January 2000). The MIC for Compound 10 in the absence of light was investigated, using a protocol based on the MIC protocol produced by the NCCLS (National Committee for Clinical Laboratory Standards (NCCLS) Handbook M7-A5, supra).

The minimum bacteriocidal concentration (MBC) is defined as the minimal concentration of drug needed to kill most (99.9%) of the viable organisms after incubation for a fixed length of time (generally 24 hours) under a given set of conditions (National Committee for Clinical Laboratory Standards (NCCLS) Handbook M26-A; "Methods for determining Bactericidal Activity of Antimicrobial Agents; Approved Guidelines" Volume 19 number 18, September 1999).

Methodology

*Staphylococcus aureus* BAA-44, a multi-drug resistant Methicillin Resistant *Staphylococcus aureus* (MRSA) strain obtained from the ATCC catalogue, was used in this study. The following concentrations of Compound 10 were investigated: 0.764 ; 0.382: 0.191; 0.0955; 0.0478; 0.0239, 0.0119, 0.00597, 0.00298, 0.00149, 0.00075 & 0.00037 μg/mL. Stock solutions were made up in distilled water and serial dilutions undertaken of this to produce the required concentrations immediately prior to use.

At least 3 to 5 well-isolated colonies of the same morphological type were selected from an agar plate culture and the growth transferred to a tube containing 100 mL of Isosensitest Broth and the broth culture is incubated at 37° C. overnight. The culture was then be diluted to a final density of 10$^4$ cells/mL with fresh Isosensitest Broth and incubated with shaking at 37° C. until the cells entered exponential growth.

0.09 mL of the adjusted inoculum was transferred into each of 24 wells of a polystyrene 96 well microtiter plate. A control well of bacteria alone in the presence of growth medium alone was included (as a positive control).

0.09 mL of the Compound 10 stock solutions from the dilution series were pipetted into the relevant well for the microtiter plates and incubated in the dark at 37° C. and the plates examined after 24 hours incubation to determine the turbidity in each well. These data are used to determine the MIC.

After 24 hours incubation at 37° C., 25 μL samples of the fluid from the wells without visible bacterial growth (four wells up) were inoculated onto nutrient agar plates as spots and incubated at 37° C. for a further 24 hours to determine the MBC.

Results

The results demonstrated that the MIC for Compound 10 in the absence of light was 0.0955 µg/mL and that the MBC was 0.382 µg/mL (Table 1).

TABLE 1

MIC and MBC data for Compound 10

| | MIC (µg/mL) | MBC (µg/mL) |
|---|---|---|
| Series 1 | 0.0955 | 0.382* |
| Series 2 | 0.0955 | Not determined |

*growth on sub of 0.191 much reduced from initial inoculum to about $10^3$/ml

Conclusions

The results demonstrate that in the absence of light Compound 10 has low MIC and MBC values. These data indicate that Compound 10 is considerably more potent as an antibiotic than some traditional antibiotics (see Table 2):

TABLE 2

MIC and MBC values for compound 10 and conventional antibiotics

| Compound | MIC Values (µg/mL) | MBC Values (µg/mL) |
|---|---|---|
| Compound 10 | 0.0955 | 0.382 |
| Vancomycin | 1[a] | 4-16[b] |
| Zyvox ® (Linezolid) | 4[a] | 4->64[c] |

[a]Critchley I A et al. Baseline study to determine in vitro activities of daptomycin against gram-positive pathogens isolated in the United States in 2000-2001. *Antimicrobial Agents and Chemotherapy* (2003); 47(5): 1689-93
[b]Biavasco F et al. In vitro antibacterial activity of LY333328, a new semi-synthetic glycopeptide. *Antimicrobial Agents and Chemotherapy* (1997); 41(10): 2165-72
[c]Fuchs P C et al. In vitro bactericidal activity of daptomycin against staphylococci. *Journal of Antimicrobial Chemotherapy* (2002); 49: 467-70

Example C

Innate Anti-Bacterial Activity of Compound 10—Activity Over a Range of Reference Strains and Clinical Isolates The Minimum Inhibitory Concentrations (MIC's) for Compound 10, over a range of reference strains and clinical isolates, were determined using IsoSensitest® broth and Minimum Bactericidal concentrations (MBC's) determined by subculture onto Columbia blood agar.

Methodology

1. A 5 mg/ml stock solution of Compound 10 was made up in water
2. A series of dilutions were undertaken to produce a range of concentrations between 32-0.001 mg/L
3. The test microorganisms were grown up overnight in IsoSensitest® broth
4. The cultures were then diluted with fresh broth to a final concentration of $10^4$ organisms/ml and placed on a shaker for 90 minutes at 37° C.
5. 90 µl of the broth culture containing the microorganisms were transferred to each of 12 wells in a row in a microtitre tray and repeated in a control tray—four organisms per tray
6. 90 µL of the appropriate Compound 10 dilution was then added to each well containing organisms to give a final dilution series from 16 mg/L to 0.0005 mg/L
7. The solutions were mixed well and incubated in the dark for 24 hours
8. The MIC was recorded and 25 µL from wells showing no growth was subcultured onto blood agar for MBC determination
9. The MBC values were recorded after overnight incubation of the subcultures.
10. Controls of uninoculated broth and broth plus inoculum were undertaken for each organism in each tray Results The results are shown in Table 3.

TABLE 3

MIC and MBC values for compound 10 and conventional antibiotics

| Organism | Strain | Cpd 10 MIC (mg/L) | Cpd 10 MBC (mg/L) |
|---|---|---|---|
| (a) *Staphylococcus aureus* (methicillin resistant) | | | |
| | ATCC BAA-44 | | |
| | Experiment 1 | | |
| | Experiment 2 | 0.5 | 1 |
| | Experiment 3 | 2 | 2 |
| | Experiment 4 | 0.5 | 1 |
| | Experiment 5 | 0.5 | >1 |
| | Experiment 6 | 0.5 | 1 |
| | NCTC 11939 (EMRSA-1) | 0.5 | 0.5 |
| | EMRSA-15* | 1 | 1 |
| | EMRSA-16* | 0.5 | 0.5 |
| (b) *Staphylococcus aureus* (methicillin sensitive) | | | |
| | NCTC 6571 | 0.5 | 0.5 |
| | ATCC 25923 | 0.5 | 1 |
| (c) *Staphylococcus epidermidis* (methicillin resistant) | | | |
| | 38808* | 0.5 | 0.5 |
| | 33759* | 0.5 | 1 |
| | 33659* | 0.5 | 1 |
| | 36572* | 0.25 | 0.25 |
| (d) *Staphylococcus epidermidis* (methicillin sensitive) | | | |
| | 37453* | 0.5 | 0.5 |
| (e) *Enterococcus faecium* | | | |
| | NCTC 12204 | 1 | 1 |
| | E1* | 0.5 | 1 |
| | E5* | 0.5 | 1 |
| | E19* | 0.5 | 0.5 |
| | E44* | 0.5 | 0.5 |
| (f) *Enterococcus faecalis* | | | |
| | ATCC 29212 | 1 | >1 |
| | E3* | 0.5 | 1 |
| | E4* | 0.5 | 0.5 |
| | E10* | 0.5 | 1 |
| | E37* | 0.5 | 1 |

*Clinical isolates

Conclusions

The results demonstrate that Compound 10 has very low MIC and MBC values for a range of gram-positive bacterial strains. The MIC and MBC values are almost identical within the limitations of the methodology, suggesting that the mode of antimicrobial activity is bacteriocidal as opposed to bacteriostatic.

Example D

Toxicity Testing of Compound 10 Against Human Cells

Methodology

Test compounds were screened for toxicity against cultured human skin cells using normal human epidermal keratinoctes (NHEK) and normal human dermal fibroblasts (NHDF), purchased from CellSystems Biotechnologie GmbH, Germany.

The NHEK and NHDF cells were used between passages 3 and 10. The cells were seeded with 7.5 and/or $15 \times 10^4$ cells/well (microtitre plate) and were allowed to attach overnight in an incubator (37° C., 5% $CO_2$). After incubation with different concentrations of the selected photosensitisers for various times, the cells were incubated for 24 hours in the dark.

Toxicity was tested by standard MTT-assay (Mossman et al., 1983 *J. Immunological Methods* 65: 55-63). MTT is an indicator of metabolically active cells. Dependent on enzyme activity in mitochondria a colour reaction can be visualised, which can be measured by ELISA reader (540 nm). The cell viability was normalised to one, which means, the OD values of cells after incubation in the absence of a test compound were normalised to one. Each experiment was repeated three times.

Results

Figure 1:
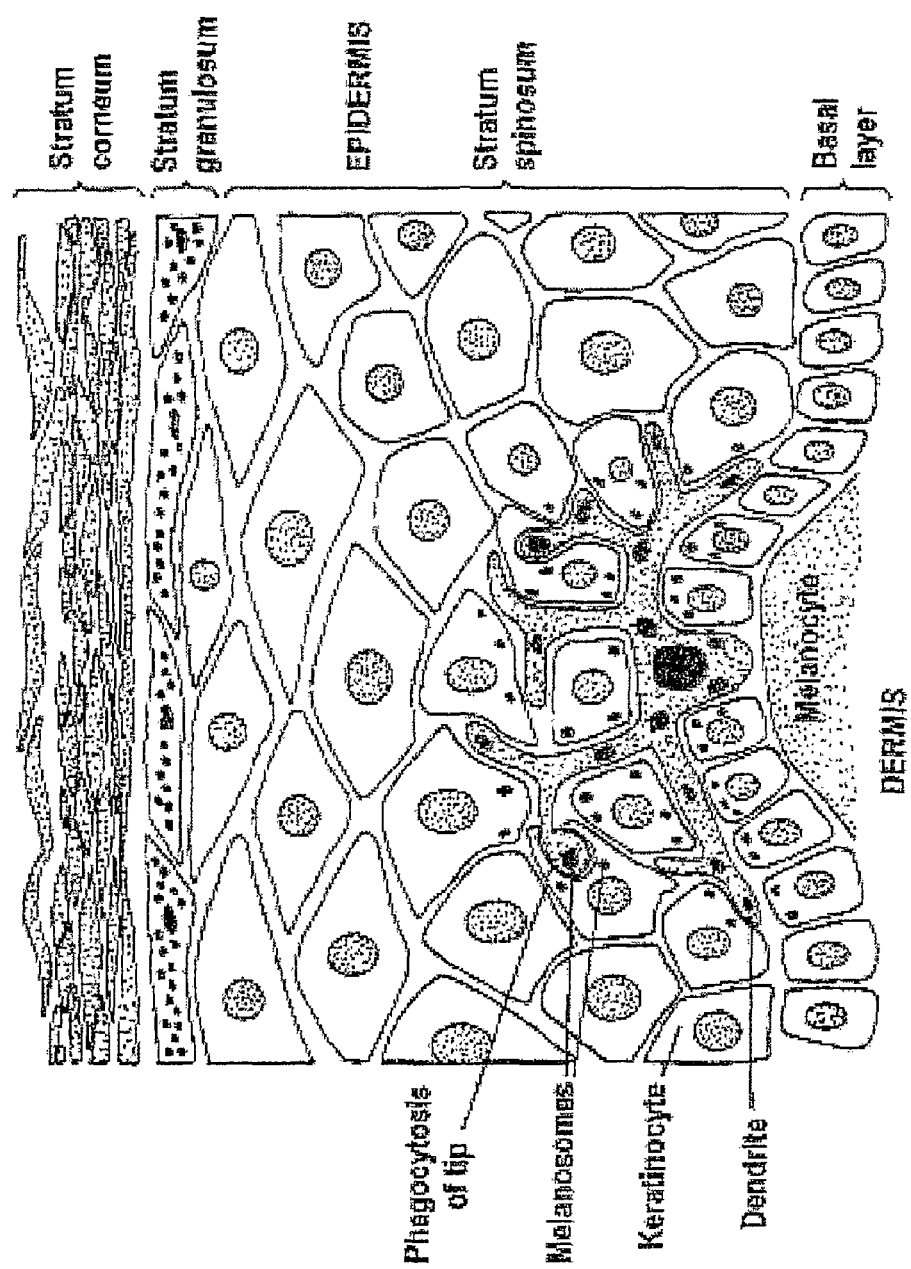
FIG. 1 shows a schematic diagram of the structure of skin.
Figure 2:
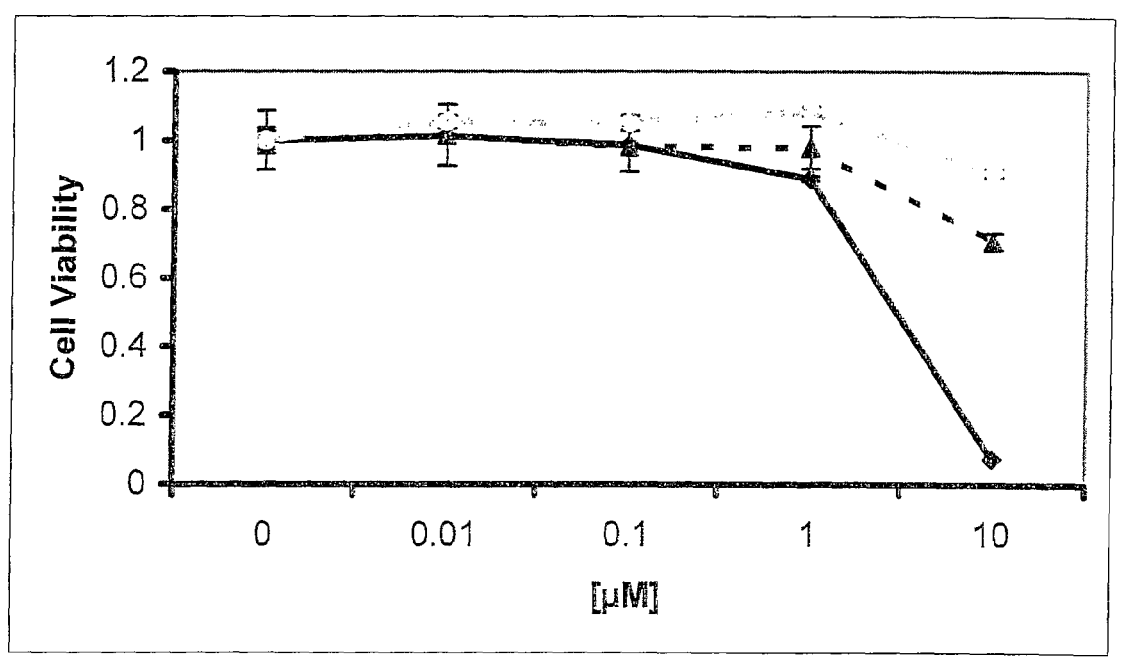
FIG. 2 shows cell toxicity of normal human dermal fibroblasts after 5 minutes, 1 hour and 4 hours incubation with Compound 10.

Results of the toxicity studies in keratinocytes and fibroblasts are shown in FIGS. 2 and 3. The data demonstrate that Compound 10 does not demonstrate an innate toxicity for either normal human epidermal keratinocytes or normal human dermal fibroblasts at doses which are known to have an anti-bacterial effect.

Example E

Binding of Exemplary Compounds with Bacterial Cells

Binding of Compounds 8, 10 and 12 with *E. coli*

*E. coli* cells were incubated for 5 min with Compound 8, 10 or 12 at various concentrations (1-7.5 µM). At the end of the incubation period, the cells were sedimented by centrifugation to remove the fraction of unbound test compound and the cell pellet was resuspended in 2 ml of 2% SDS to obtain cell lysates. After overnight incubation with SDS, the amount of cell-bound test compound was estimated by spectrofluorimetric analysis of the cell lysates. The concentration of the compounds in the cell lysates was calculated by measuring the intensities at the maximum of the emission fluorescence spectrum and interpolating the data on a calibration plot. The amount of cell-bound test compound was expressed as nmoles of compound per mg of cell protein. The protein concentration was determined by the method of Lowry (Lowry et al., 1951, *J. Biol. Chem.* 193:265-275).

All experiments were run in triplicate and the results represent the average of 3 determinations with standard deviations.

The amount of porphyrin recovered from the cells is shown in Table 4.

TABLE 4

| Concentration of compound | Bound compound (nmoles/mg cell proteins) | | |
|---|---|---|---|
| (µM) | Compound 8 | Compound 12 | Compound 10 |
| (a) 0 washings | | | |
| 0.01 | 0.024 ± 0.01 | 0.041 ± 0.02 | 0.026 ± 0.005 |
| 0.1 | 0.056 ± 0.02 | 0.151 ± 0.02 | 0.274 ± 0.05 |
| 0.5 | 0.522 ± 0.2 | 0.806 ± 0.14 | 1.542 ± 0.350 |
| 1 | 3.670 ± 0.7 | 2.70 ± 0.30 | 2.70 ± 0.354 |
| (b) 3 washings | | | |
| 0.01 | 0.009 ± 0.001 | 0.021 ± 0.005 | 0.015 ± 0.0004 |
| 0.1 | 0.030 ± 0.02 | 0.089 ± 0.02 | 0.078 ± 0.02 |
| 0.5 | 0.274 ± 0.15 | 0.622 ± 0.10 | 0.334 ± 0.092 |
| 1 | 2.230 ± 0.8 | 1.930 ± 0.20 | 1.278 ± 0.102 |

The results shown in Table 3. show that the three test compounds bind to *E. coli* with similar efficiency and that about 50% of the compound that is associated to the cells at the end of the incubation period (5 min) is removed by 3 washings with PBS.

Example F

Stability Studies

Chemical Stability

The following HPLC methodology was established for the analysis of the exemplary compounds of the invention.

The method involves detection by UV at a wavelength of 420 nm, which is very specific for these compounds. In order to monitor impurities not related to the porphyrin structure (and therefore not absorbing at 420 nm) UV spectra of the whole chromatograms were also recorded between 200 nm and 700 nm by DAD (diode array detector) in certain experiments.

Column: Zorbax Phenyl, 250×4.6 mm, 5 µm
Eluent A: 1.5 g sodium dodecylsulfate+1 mL formic acid in 1000 mL water
Eluent B: 1.5 g sodium dodecylsulfate+1 mL formic acid in 200 mL water+800 mL tetrahydrofurane

| Gradient: | |
|---|---|
| Time [mm] | Eluent B [%] |
| 0 | 50 |
| 31 | 65 |
| 32 | 90 |
| 33 | 50 |
| 43 | 50 |

Flow rate: 0.4 mL/min
Detection: 420 nm
Column temperature: 25° C.
Injection volume: 10 µl
Solutions: Porphyrin derivatives were dissolved in eluent A to give a final concentration of approximately 0.3 mg/ml.
Typical retention time of the exemplary compounds was approximately 8 minutes (18 minute runtime).

Qualitative stress tests were undertaken on the exemplary compounds of is the invention. Analysis was undertaken by HPLC & LC-MS. The compounds were stress tested in solid form, in an aqueous solution and a solution made up in phosphate-buffered saline buffer. The samples were initially incubated for 7 days at 50° C. and a sample removed for testing. The samples were then incubated for a further 7 days at 70° C., samples removed as before and the samples incubated further for 7 days at 90° C. HPLC analysis of freshly prepared solutions was undertaken and compared to the samples after 7, 14 and 21 days incubation. A visual comparison of the chromatograms was then undertaken and the content of the main products and by-products as area percentage values determined (see FIG. 4).

The 3D plots of the chromatograms show no indications for additional formation of fragments (no signals at lower wavelengths)

The plot in FIG. 5 shows the sample after 21 days in PBS buffer, which showed the largest degradation effect. The results demonstrated minimal degradation on analysis of solid drug and drug in solution heated to 80° C. for a number of weeks.

Conclusions

Compounds 10 and 12 were both found to exhibit good stability and were very stable even under the stressed conditions of the test protocol. Although Compound 8 was less stable than Compounds 10 and 12, the stability demonstrated was found to be sufficient for practical use.

Stability of Exemplary Compounds in Formulations

The stability of three exemplary compounds (Compounds 8, 10 and 12) and one reference compound (Compound 1), stored at 40° C. in the dark over 8 weeks in polyethylene vials in various aqueous-based formulations, was evaluated as follows:

Sodium laureth sulphate (SLES)+water

9:1 water:ethanol

SLES+9:1 water:ethanol

UV spectra were recorded over the range 350-700 nm over a period of 7 weeks and a visual evaluation of the samples made at 8 weeks.

The results indicate that all compounds tested exhibited good stability over an eight-week period (see FIG. 6).

For Compounds 8 and 10, the stability study was extended to 17 weeks (see FIG. 7).

Example G

Acute Toxicity Testing of Compound 10

Compound 10 was tested at 3.2 mM in a topical formulation in a standard acute dermal toxicity test to determine if any clinical or histological toxicity for the compound could be detected.

The acute toxicity protocol was based on OECD Guidelines for the testing of chemicals/Section 4—Health Effects Test Number 402: Acute Dermal Toxicity.

Results And Conclusions

After clinical, macroscopic and microscopic observation, no clinical toxicology was observed. No histological toxicology of any major organ (including the skin) was observed.

In conclusion, Compound 10 does not result in any acute toxic effect: in fact, no significant clinical or pathological signs related to the substance or its vehicle application were observed.

The invention claimed is:

1. A method for killing microorganisms comprising administering to a patient an effective amount of a compound of Formula I or II

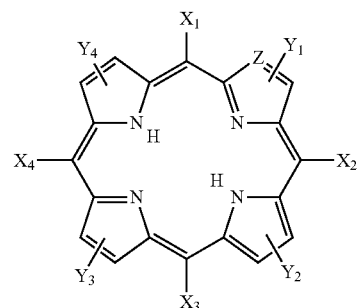

I

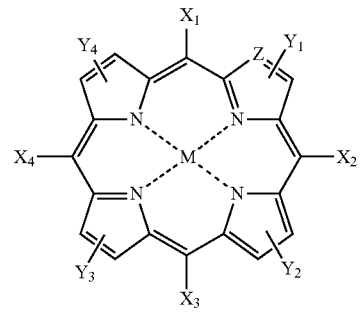

II wherein:

$X_1$, $X_2$, $X_3$ and $X_4$ independently represent a hydrogen atom, a lipophilic moiety, a phenyl group, a lower alkyl, alkaryl or aralkyl group, or a cationic group of the following formula;

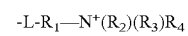

-L-$R_1$—$N^+(R_2)(R_3)R_4$ wherein:

L is a linking moiety or is absent;

$R_1$ represents lower alkylene, lower alkenylene or lower alkynylene, which is optionally substituted by one or more substituents selected from lower alkyl, lower alkylene (optionally interrupted with oxygen), fluoro, $OR_5$, $C(O)R_6$, $C(O)OR_7$, $C(O)NR_8R_9$, $NR_{10}R_{11}$ and $N^+R_{12}R_{13}R_{14}$; and $R_2$, $R_3$ and $R_4$ independently represent H, aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)NR_8 R_9$, $NR_{10}R_{11}$ and $N^+R_{12}R_{13}R_{14}$ Z is —CH or N; and $Y_1$, $Y_2$, $Y_3$ and $Y_4$ are absent or independently represent aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)NR_8R_9$, $NR_{10}R_{11}$, $N^+R_{12}R_{13}R_{14}$, or, taken in conjunction to the pyrrole ring to which they attach, forms a cyclic group; and $R_5$, $R_6$, $R_7$, $R_8$, $R_9$, $R_{10}$, $R_{11}$, $R_{12}$, $R_{13}$ and $R_{14}$ independently represent H or lower alkyl provided that at least one of $X_1$, $X_2$, $X_3$ and $X_4$ is a cationic group as defined above and at least one of $X_1$, $X_2$, $X_3$ and $X_4$ is a hydrogen atom, M is a metallic element or a metalloid element, and
wherein the compound of formula I or II is not exposed to a stimulus which activates antimicrobial activity.

2. The method of claim 1 wherein the compound of Formula I or II is not exposed to a stimulus which activates antimicrobial activity.

3. The method of claim 1, wherein the compound exhibits anti-microbial activity in the absence of irradiation with a photodynamic therapy light source or an ultrasound source.

4. The method of claim 1, wherein M is a divalent or trivalent metallic element.

5. The method of claim 1, wherein M is selected from the group consisting of Zn (II), Cu (II), La (III), Lu (III), Y (III), In (III) Cd (II), Mg (II), Al(III), Ru, Ni(II), Mn(III), Fe(III) and Pd(II).

6. The method of claim 1, wherein M is a metalloid element, for example silicon (Si) or germanium (Ge).

7. The method of claim 1, wherein $Y_1$, $Y_2$, $Y_3$ and $Y_4$ are absent.

8. The method of claim 1, wherein Z is —CH.

9. The method of claim 1, wherein $R_1$ is an unsubstituted lower alkylene, lower alkenylene or lower alkynylene group.

10. The method of claim 1, wherein $R_1$ is —$(CH_2)_m$- and m is an integer between 1 and 20.

11. The method of claim 10, wherein m is an integer between 1 and 10.

12. The method of claim 11, wherein m is 3.

13. The method of claim 1, wherein at least one of $R_2$, $R_3$, and $R_4$ are lower alkyl, lower alkenyl or lower alkynyl groups.

14. The method of claim 13, wherein at least one of $R_2$, $R_3$, and $R_4$ are unsubstituted lower alkyl groups.

15. The method of claim 13, wherein at least one of $R_2$, $R_3$ and $R_4$ is an alkyl group which is substituted with a primary, secondary or tertiary amine group or a quaternary ammonium group.

16. The method of claim 1, wherein $R_1$ is —$(CH_2)_3$—, $R_2$ and $R_3$ are $CH_3$ and $R_4$ is —$(CH_2)_3$—$N(CH_3)_2$.

17. The method of claim 1, wherein $R_1$ is —$(CH_2)_3$—, and $R_2$, $R_3$ and $R_4$ are each $CH_3$.

18. The method of claim 1, wherein $R_1$ is —$(CH_2)_3$—, and $R_2$, $R_3$ and $R_4$ are each $C_2H_5$.

19. The method of claim 1, wherein L is selected from the group consisting of phenoxy, phenylene, sulfonyl amido, aminosulfonyl, sulfonylimino, phenylsulfonyl-amido, phenylaminosulfonyl, urea, urethane and carbamate linking moieties.

20. The method of claim 19, wherein at least one of $X_1$, $X_2$, $X_3$ and $X_4$ are

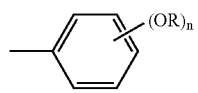

wherein R is —$R_1$—$N^+(R_2)(R_3)R_4$, as defined in claim 1 and n is an integer between 1 and 3.

21. The method of claim 19, wherein at least one of $X_1$, $X_2$, $X_3$ and $X_4$ are

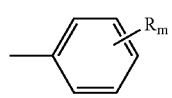

wherein R is —$R_1$—$N^+(R_2)(R_3)R_4$, as defined in claim 1 and m is an integer between 1 and 3.

22. The method of claim 19, wherein at least one of $X_1$, $X_2$, $X_3$ and $X_4$ are

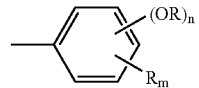

wherein each R independently is —$R_1$—$N^+(R_2)(R_3)R_4$, as defined in claim 1 and n and m are integers between 1 and 3 and wherein the sum of n and m is an integer between 1 and 3.

23. The method of claim 20 or 21, wherein n or m is 3.

24. The method of claim 20 or 21, wherein n or m is 2.

25. The method of claim 20 or 21, wherein at least one of n or m is 1.

26. The method of claim 19, wherein L is mono-substituted at the para-position.

27. The method of claim 19, wherein L is mono- or di-substituted at a meta-position(s).

28. The method of claim 19, wherein L is mono- or di-substituted at an ortho-position(s).

29. The method of claim 1, wherein two of X1-X4 are cationic groups, as defined in claim 1, located on opposite sides of the porphyrin ring, at ring positions 5 and 15 or ring positions 10 and 20.

30. The method of claim 29, wherein $X_1$ and $X_3$ are a hydrogen atom, a lipophilic moiety, a phenyl group, a lower alkyl, alkaryl or aralkyl group and $X_2$ and $X_4$ are cationic groups, or wherein $X_1$ and $X_3$ are cationic groups and $X_2$ and $X_4$ are a hydrogen atom, a lipophilic moiety, a phenyl group, a lower alkyl, alkaryl or aralkyl group.

31. The method of claim 1, wherein two of X1-X4 are cationic groups, as defined in claim 1, located, on neighbouring positions of the porphyrin ring, at ring positions 5 and 10, ring positions 10 and 15, ring positions 15 and 20, or ring positions 20 and 5.

32. The method of claim 31, wherein $X_1$ and $X_2$ are hydrogen and $X_3$ and $X_4$ are cationic groups, or $X_2$ and $X_3$ are hydrogen and $X_4$ and $X_1$ are cationic groups.

33. The method of claim 1, wherein at least one of $X_1$, $X_2$, $X_3$ and $X_4$ is a lipophilic moiety.

34. The method of claim 33, wherein the lipophilic moiety is a saturated, straight-chain alkyl group of formula —$(CH_2)_p$ $CH_3$ wherein 'p' is an integer between 1 and 22.

35. The method of claim 34, wherein p is between 1 and 18.

36. The method of claim 1, wherein none of $X_1$, $X_2$, $X_3$ and $X_4$ is a lipophilic moiety.

37. The method of claim 1, wherein none of $X_1$, $X_2$, $X_3$ and $X_4$ is a phenyl group.

38. The method of claim 1, wherein the compound is water-soluble.

39. The method of claim 1, wherein the compound is selected from the group consisting of 5,15-bis-(4-{3-[(3-Dimethylamino-propyl)-dimethyl-ammonio]-propyl-oxy}-phenyl)-porphyrin dichloride; 5,15-bis-[4-(3-Triethylammonio-propyloxy)-phenyl]-porphyrin dichloride; 5,15-bis-[3-(3-Trimethylammonio-propyloxy)-phenyl]-porphyrin dichloride; 5,15-bis-[4-(3-Trimethylammonio-propyloxy)-phenyl]-porphyrin dichloride; 5-[3,5-bis-(3-Trimethylammonio-propyloxy)-phenyl]-15-undecyl-porphyrin dichloride; 5-{4-[3-Dimethyl-(3-dimethylaminopropyl)-ammonio-propyl-oxy]-phenyl}-15-(4-dodecyloxy-phenyl) -porphyrin chloride; 3-[({3-[(3-{4-[15-(4-Dodecyloxy-phenyl)-porphyrin-5-yl]-phenoxy}-propyl)-dimethyl-ammonio]-propyl}-dimethyl-ammonio)-propyl]-trimethyl-ammonium trichloride; 5,15-bis-[3-(3-Trimethylammmonio-propyloxy)-phenyl]-10-undecyl-porphyrin dichloride; 5-{4-[3-Dimethyl-(3-trimethylammonio-propyl)-ammonio-propyloxy]-phenyl}-15-(4-dodecyloxy-phenyl)-porphyrin dichloride; and 5-[4-(3-Dimethyldecyl-ammoniopropyloxy)-phenyl]-15-{4- [3-di-methyl-(3-dimethylaminopropyl)-ammoniopropyloxy]-phenyl}-porphyrin dichloride.

40. The method of claim 39, wherein the compound is in a metallated form.

41. The method of claim 1, wherein the compound is substantially non-toxic to mammalian cells.

42. The method of claim 1, wherein the compound is administered orally.

43. The method of claim 1, wherein the compound is administered parenterally.

44. The method of claim 1, wherein the compound is administered topically.

45. The method of claim 1, wherein the microorganisms are selected from the group consisting of bacteria, mycoplasmas, yeasts, fungi and viruses.

46. The method of claim 1, wherein the microorganisms are bacteria which are resistant to one or more conventional antibiotic agents.

47. The method of claim 1, wherein the microorganisms are on a light-inaccessible surface or in a light-inaccessible area.

48. The method of claim 1, wherein the compound of Formula I or II is for use in the curative treatment of microbial infections, to reduce the onset of microbial infections, and combinations thereof.

49. The method of claim 48, wherein the microbial infection is a systemic infection.

50. The method of claim 1, wherein the compound of Formula I or II is administered to reduce the onset of a dermatological infection, to treat a dermatological infection, and combinations thereof.

51. The method of claim 1, wherein the compound of Formula I or II is administered to reduce the onset of an infection in the lungs, to treat an infection in the lungs, and combinations thereof.

52. The method of claim 1, wherein the compound of Formula I or II is administered to reduce the onset of wound infection or ulcers, to treat wound infection or ulcers, and combinations thereof.

53. A method for treating a patient in need of treatment with an antimicrobial agent comprising administering to the patient the compound of claim 1, wherein the method does not comprise irradiating the compound with a stimulus which activates antimicrobial activity.

54. The method of claim 53, wherein the compound is administered orally.

55. The method of claim 53, wherein the compound is administered parenterally.

56. The method of claim 53, wherein the compound is administered topically.

57. The method of claim 53, wherein the patient has a dermatological infection or lung infection.

58. The method of claim 53, wherein the patient has a wound infection.

59. The method of clam 35, wherein p is between 2 and 16.

60. The method of clam 35, wherein p is between 4 and 12.

* * * * *

UNITED STATES PATENT AND TRADEMARK OFFICE
CERTIFICATE OF CORRECTION

PATENT NO.        : 7,977,474 B2
APPLICATION NO.   : 11/571130
DATED             : July 12, 2011
INVENTOR(S)       : William G. Love, William Rhys-Williams and Derek Brundish Page 1 of 1

It is certified that error appears in the above-identified patent and that said Letters Patent is hereby corrected as shown below:

Claim 26, column 78, line 19, replace "para-position" with "*para*-position."

Claim 27, column 78, line 21, replace "meta-position" with "*meta*-position(s)."

Claim 28, column 78, line 23, replace "ortho-position" with "*ortho*-position(s)."

Signed and Sealed this
Twenty-fourth Day of April, 2012

David J. Kappos
*Director of the United States Patent and Trademark Office*